(12) United States Patent
Wensley et al.

(10) Patent No.: US 10,194,693 B2
(45) Date of Patent: Feb. 5, 2019

(54) AEROSOL GENERATING DEVICE

(71) Applicant: FONTEM HOLDINGS 1 B.V., Amsterdam (NL)

(72) Inventors: Martin Wensley, Campbell, CA (US); Peter Lloyd, Walnut Creek, CA (US)

(73) Assignee: FONTEM HOLDINGS 1 B.V., Amsterdam (NL)

( * ) Notice: Subject to any disclaimer, the term of this patent is extended or adjusted under 35 U.S.C. 154(b) by 716 days.

(21) Appl. No.: 14/491,592

(22) Filed: Sep. 19, 2014

(65) Prior Publication Data

US 2015/0196060 A1    Jul. 16, 2015

Related U.S. Application Data

(60) Provisional application No. 62/048,795, filed on Sep. 10, 2014, provisional application No. 61/880,525, filed on Sep. 20, 2013.

(51) Int. Cl.
| | | |
|---|---|---|
| *A61M 16/00* | (2006.01) |
| *A24F 47/00* | (2006.01) |
| *A61M 15/06* | (2006.01) |
| *A61M 11/04* | (2006.01) |
| *A61M 15/00* | (2006.01) |

(Continued)

(52) U.S. Cl.
CPC ......... *A24F 47/008* (2013.01); *A61M 11/042* (2014.02); *A61M 15/002* (2014.02); *A61M 15/06* (2013.01); *F22B 1/284* (2013.01); *F22B 1/288* (2013.01); *A61M 11/001* (2014.02); *A61M 2016/0021* (2013.01); *A61M 2016/0024* (2013.01); *A61M 2205/3306* (2013.01); *A61M 2205/3368* (2013.01); *A61M 2205/3553* (2013.01); *A61M 2205/3584* (2013.01); *A61M 2205/3592* (2013.01);

(Continued)

(58) Field of Classification Search
None
See application file for complete search history.

(56) References Cited

U.S. PATENT DOCUMENTS

| | | |
|---|---|---|
| 2,057,353 A | 10/1936 | Whittemore |
| 4,106,503 A | 8/1978 | Rosenthal et al. |

(Continued)

FOREIGN PATENT DOCUMENTS

| | | |
|---|---|---|
| CN | 1127983 A | 7/1996 |
| CN | 2648836 Y | 10/2004 |

(Continued)

OTHER PUBLICATIONS

International search report and written opinion dated May 1, 2015 for PCT Application No. US2015/012512.

(Continued)

*Primary Examiner* — Thor Campbell
(74) *Attorney, Agent, or Firm* — Perkins Coie LLP; Kenneth H. Ohriner

(57) ABSTRACT

Provided herein are methods, devices, kits, and systems for modulating aerosol particle size generated by an aerosol generating device (e.g., electronic nicotine delivery device). Also described herein are methods, devices, kits, and systems for modulating the delivery of aerosol particles generated by an aerosol generating device (e.g., an electronic nicotine delivery device) to the deep lung of a subject.

9 Claims, 5 Drawing Sheets

(51) Int. Cl.
*F22B 1/28* (2006.01)
*A61M 11/00* (2006.01)

(52) U.S. Cl.
CPC ............ A61M 2205/3653 (2013.01); A61M
2205/8206 (2013.01); A61M 2209/06
(2013.01)

(56) References Cited

U.S. PATENT DOCUMENTS

| | | | |
|---|---|---|---|
| 4,243,605 A | | 1/1981 | Eisenhardt, Jr. et al. |
| 4,446,862 A | | 5/1984 | Baum et al. |
| 4,735,217 A | * | 4/1988 | Gerth .................... A24F 47/008 128/203.17 |
| 4,922,901 A | | 5/1990 | Brooks et al. |
| 4,947,874 A | | 8/1990 | Brooks et al. |
| 4,947,875 A | | 8/1990 | Brooks et al. |
| 4,953,572 A | | 9/1990 | Rose et al. |
| 5,015,741 A | | 5/1991 | Osdene et al. |
| 5,060,671 A | | 10/1991 | Counts et al. |
| 5,093,894 A | | 3/1992 | Deevi et al. |
| 5,224,498 A | | 7/1993 | Deevi et al. |
| 5,228,460 A | | 7/1993 | Sprinkel et al. |
| 5,249,586 A | | 10/1993 | Morgan et al. |
| 5,261,423 A | | 11/1993 | Gaudlitz et al. |
| 5,269,327 A | | 12/1993 | Counts et al. |
| 5,322,075 A | | 6/1994 | Deevi et al. |
| 5,353,813 A | | 10/1994 | Deevi et al. |
| 5,369,723 A | | 11/1994 | Counts et al. |
| 5,372,148 A | | 12/1994 | Mccafferty et al. |
| 5,388,594 A | | 2/1995 | Counts et al. |
| 5,468,936 A | | 11/1995 | Deevi et al. |
| 5,479,948 A | | 1/1996 | Counts et al. |
| 5,487,378 A | | 1/1996 | Robertson et al. |
| 5,497,763 A | | 3/1996 | Lloyd et al. |
| 5,498,850 A | | 3/1996 | Das |
| 5,498,855 A | | 3/1996 | Deevi et al. |
| 5,505,214 A | | 4/1996 | Collins et al. |
| 5,507,277 A | | 4/1996 | Rubsamen et al. |
| 5,522,385 A | | 6/1996 | Lloyd et al. |
| 5,530,225 A | | 6/1996 | Hajaligol |
| 5,544,646 A | | 8/1996 | Lloyd et al. |
| 5,573,692 A | | 11/1996 | Das et al. |
| 5,591,368 A | | 1/1997 | Fleischhauer et al. |
| 5,613,504 A | | 3/1997 | Collins et al. |
| 5,613,505 A | | 3/1997 | Campbell et al. |
| 5,649,554 A | | 7/1997 | Sprinkel et al. |
| 5,659,656 A | | 8/1997 | Das |
| 5,665,262 A | | 9/1997 | Hajaligol et al. |
| 5,666,977 A | | 9/1997 | Higgins et al. |
| 5,692,291 A | | 12/1997 | Collins et al. |
| 5,692,525 A | | 12/1997 | Counts et al. |
| 5,692,526 A | | 12/1997 | Adams et al. |
| 5,718,222 A | | 2/1998 | Lloyd et al. |
| 5,730,158 A | | 3/1998 | Collins et al. |
| 5,743,251 A | | 4/1998 | Howell et al. |
| 5,750,964 A | | 5/1998 | Counts et al. |
| 5,778,897 A | | 7/1998 | Nordlicht |
| 5,798,850 A | | 8/1998 | Ishikawa et al. |
| 5,816,263 A | | 10/1998 | Counts et al. |
| 5,865,185 A | | 2/1999 | Collins et al. |
| 5,894,841 A | | 4/1999 | Voges et al. |
| 5,915,387 A | | 6/1999 | Baggett et al. |
| 5,934,289 A | | 8/1999 | Watkins et al. |
| 5,954,979 A | | 9/1999 | Counts et al. |
| 5,957,124 A | | 9/1999 | Lloyd et al. |
| 5,960,792 A | | 10/1999 | Lloyd et al. |
| 5,971,951 A | | 10/1999 | Ruskewicz |
| 5,988,176 A | | 11/1999 | Baggett et al. |
| 6,026,820 A | | 2/2000 | Baggett et al. |
| 6,040,560 A | | 3/2000 | Fleischhauer et al. |
| 6,053,176 A | | 4/2000 | Adams et al. |
| 6,062,213 A | | 5/2000 | Fuisz et al. |
| 6,070,575 A | | 6/2000 | Gonda et al. |
| 6,116,237 A | | 9/2000 | Schultz et al. |
| 6,116,247 A | | 9/2000 | Banyasz et al. |

| | | |
|---|---|---|
| 6,125,853 A | 10/2000 | Susa et al. |
| 6,131,570 A | 10/2000 | Schuster et al. |
| 6,155,268 A | 12/2000 | Takeuchi |
| 6,192,882 B1 | 2/2001 | Gonda |
| 6,196,218 B1 | 3/2001 | Voges |
| 6,230,706 B1 | 5/2001 | Gonda et al. |
| 6,234,167 B1 | 5/2001 | Cox et al. |
| 6,254,854 B1 | 7/2001 | Edwards et al. |
| 6,263,872 B1 | 7/2001 | Schuster et al. |
| 6,349,728 B1 | 2/2002 | Pham |
| 6,360,739 B1 | 3/2002 | Rand et al. |
| 6,443,146 B1 | 9/2002 | Voges |
| 6,503,922 B2 | 1/2003 | Crooks et al. |
| 6,516,796 B1 | 2/2003 | Cox et al. |
| 6,532,965 B1 | 3/2003 | Abhulimen et al. |
| 6,543,442 B2 | 4/2003 | Gonda et al. |
| 6,557,552 B1 | 5/2003 | Cox et al. |
| 6,598,602 B1 | 7/2003 | Sjoholm |
| 6,615,840 B1 | 9/2003 | Fournier et al. |
| 6,629,524 B1 | 10/2003 | Goodall et al. |
| 6,635,283 B2 | 10/2003 | Edwards et al. |
| 6,637,430 B1 | 10/2003 | Voges et al. |
| 6,647,987 B2 | 11/2003 | Gonda et al. |
| 6,655,379 B2 | 12/2003 | Clark et al. |
| 6,681,769 B2 | 1/2004 | Sprinkel, Jr. et al. |
| 6,688,313 B2 | 2/2004 | Wrenn et al. |
| 6,701,922 B2 | 3/2004 | Hindle et al. |
| 6,749,835 B1 | 6/2004 | Lipp et al. |
| 6,766,220 B2 | 7/2004 | Mcrae et al. |
| 6,766,817 B2 | 7/2004 | Da Silva |
| 6,772,756 B2 | 8/2004 | Shayan |
| 6,772,757 B2 | 8/2004 | Sprinkel, Jr. |
| 6,799,572 B2 | 10/2004 | Nichols et al. |
| 6,799,576 B2 | 10/2004 | Farr et al. |
| 6,803,545 B2 | 10/2004 | Blake et al. |
| 6,803,550 B2 | 10/2004 | Sharpe et al. |
| 6,804,458 B2 | 10/2004 | Sherwood et al. |
| 6,810,883 B2 | 11/2004 | Felter et al. |
| 6,845,216 B2 | 1/2005 | Schuster et al. |
| 6,854,461 B2 | 2/2005 | Nichols et al. |
| 6,854,470 B1 | 2/2005 | Pu |
| 6,874,507 B2 | 4/2005 | Farr |
| 6,875,020 B2 | 4/2005 | Niddrie et al. |
| 6,883,516 B2 | 4/2005 | Hindle et al. |
| 6,886,557 B2 | 5/2005 | Childers et al. |
| 6,889,687 B1 | 5/2005 | Olsson |
| 6,917,754 B2 | 7/2005 | Pedrotti et al. |
| 6,923,179 B2 | 8/2005 | Gupta et al. |
| 6,962,151 B1 | 11/2005 | Knoch et al. |
| 6,994,096 B2 | 2/2006 | Rostami et al. |
| 6,995,265 B2 | 2/2006 | Comins et al. |
| 7,028,686 B2 | 4/2006 | Gonda et al. |
| 7,040,314 B2 | 5/2006 | Nguyen et al. |
| 7,070,765 B2 | 7/2006 | Rabinowitz et al. |
| 7,078,019 B2 | 7/2006 | Rabinowitz et al. |
| 7,090,830 B2 | 8/2006 | Hale et al. |
| 7,117,867 B2 | 10/2006 | Cox et al. |
| 7,128,067 B2 | 10/2006 | Byron et al. |
| 7,132,545 B2 | 11/2006 | Comins et al. |
| 7,147,170 B2 | 12/2006 | Nguyen et al. |
| 7,163,015 B2 | 1/2007 | Moffitt et al. |
| 7,167,776 B2 | 1/2007 | Maharaji et al. |
| 7,182,961 B2 | 2/2007 | Batycky et al. |
| 7,185,659 B2 | 3/2007 | Sharpe |
| 7,234,470 B2 | 6/2007 | Yang |
| 7,252,840 B1 | 8/2007 | Batycky et al. |
| 7,293,565 B2 | 11/2007 | Griffin et al. |
| 7,373,938 B2 | 5/2008 | Nichols et al. |
| 7,384,649 B2 | 6/2008 | Batycky et al. |
| 7,392,809 B2 | 7/2008 | Larson et al. |
| 7,400,940 B2 | 7/2008 | Mcrae et al. |
| 7,435,408 B2 | 10/2008 | Edwards et al. |
| 7,442,388 B2 | 10/2008 | Weers et al. |
| 7,458,373 B2 | 12/2008 | Nichols et al. |
| 7,481,226 B2 | 1/2009 | Cholet |
| 7,530,352 B2 | 5/2009 | Childers et al. |
| 7,537,009 B2 | 5/2009 | Hale et al. |
| 7,540,286 B2 | 6/2009 | Cross et al. |
| 7,550,133 B2 | 6/2009 | Hale et al. |

(56) References Cited

U.S. PATENT DOCUMENTS

| | | |
|---|---|---|
| 7,581,540 B2 | 9/2009 | Hale et al. |
| 7,585,493 B2 | 9/2009 | Hale et al. |
| 7,645,442 B2 | 1/2010 | Hale et al. |
| 7,690,385 B2 | 4/2010 | Moffitt et al. |
| 7,726,310 B2 | 6/2010 | Andrus et al. |
| 7,726,320 B2 | 6/2010 | Robinson et al. |
| 7,743,766 B2* | 6/2010 | Gupta .................. A61M 11/041 128/200.24 |
| 7,766,013 B2 | 8/2010 | Wensley et al. |
| 7,767,698 B2 | 8/2010 | Warchol et al. |
| 7,810,505 B2 | 10/2010 | Yang |
| 7,832,410 B2 | 11/2010 | Hon |
| 7,913,688 B2* | 3/2011 | Cross .................... A61M 11/041 128/203.24 |
| 7,931,020 B2 | 4/2011 | Trees et al. |
| 7,942,147 B2 | 5/2011 | Hodges et al. |
| 7,953,613 B2 | 5/2011 | Gizewski |
| 7,997,280 B2 | 8/2011 | Rosenthal |
| 8,003,080 B2 | 8/2011 | Rabinowitz et al. |
| 8,066,010 B2 | 11/2011 | Newbery et al. |
| 8,074,644 B2 | 12/2011 | Hale et al. |
| 8,156,944 B2* | 4/2012 | Han ........................ A24F 47/008 128/202.21 |
| 8,191,555 B2 | 6/2012 | Herbrich et al. |
| 8,201,554 B2 | 6/2012 | Reinhold et al. |
| 8,205,622 B2 | 6/2012 | Pan |
| 8,251,063 B2 | 8/2012 | Andrus et al. |
| 8,256,433 B2 | 9/2012 | Gonda |
| 8,314,591 B2 | 11/2012 | Terry et al. |
| 8,322,350 B2 | 12/2012 | Lipowicz |
| 8,333,197 B2 | 12/2012 | Cross et al. |
| 8,353,302 B2 | 1/2013 | Olegario et al. |
| 8,365,742 B2 | 2/2013 | Hon |
| 8,371,310 B2 | 2/2013 | Brenneise |
| 8,375,957 B2 | 2/2013 | Hon |
| 8,375,959 B2 | 2/2013 | Dittrich et al. |
| 8,381,738 B2 | 2/2013 | Luan et al. |
| 8,381,739 B2 | 2/2013 | Gonda |
| 8,393,331 B2 | 3/2013 | Hon |
| 8,402,976 B2 | 3/2013 | Fernando et al. |
| 8,424,537 B2 | 4/2013 | Rosenthal |
| 8,479,747 B2 | 7/2013 | O'connell |
| 8,490,628 B2 | 7/2013 | Hon |
| 8,495,998 B2 | 7/2013 | Schennum |
| 8,499,766 B1 | 8/2013 | Newton |
| 8,505,548 B2 | 8/2013 | Hearn |
| 8,506,935 B2 | 8/2013 | Hale et al. |
| 8,511,318 B2 | 8/2013 | Hon |
| 8,515,570 B2 | 8/2013 | Lee |
| 8,528,569 B1 | 9/2013 | Newton |
| 8,539,959 B1 | 9/2013 | Scatterday |
| 8,550,069 B2 | 10/2013 | Alelov |
| 8,558,147 B2 | 10/2013 | Greim et al. |
| 8,578,942 B2 | 11/2013 | Schennum |
| 8,596,460 B2 | 12/2013 | Scatterday |
| 8,634,709 B2 | 1/2014 | Maharajh et al. |
| 8,636,012 B2 | 1/2014 | Le Roux et al. |
| 8,640,713 B2 | 2/2014 | Fiebelkorn |
| 8,678,012 B2 | 3/2014 | Li et al. |
| 8,689,804 B2 | 4/2014 | Fernando et al. |
| 8,689,805 B2 | 4/2014 | Hon |
| 8,695,794 B2 | 4/2014 | Scatterday |
| 8,714,150 B2 | 5/2014 | Alelov |
| 8,794,231 B2* | 8/2014 | Thorens ................. A24F 47/008 128/202.21 |
| 8,857,446 B2 | 10/2014 | Wu |
| 8,903,228 B2 | 12/2014 | Goodman et al. |
| 8,910,640 B2* | 12/2014 | Sears ......................... F22B 1/28 128/202.21 |
| 8,910,641 B2 | 12/2014 | Hon |
| 8,948,578 B2* | 2/2015 | Buchberger ......... A61M 11/041 128/203.27 |
| 9,072,321 B2* | 7/2015 | Liu ........................ A24F 47/008 |
| 9,414,629 B2* | 8/2016 | Egoyants ............... A24F 47/008 |
| 9,420,829 B2* | 8/2016 | Thorens ................ A24F 47/008 |
| 9,510,623 B2* | 12/2016 | Tucker .................... H01C 17/00 |
| 9,609,893 B2* | 4/2017 | Novak, III ............ A24F 47/008 |
| 9,609,894 B2* | 4/2017 | Abramov .............. A24F 47/008 |
| 9,668,523 B2* | 6/2017 | Tucker .................... H01C 17/00 |
| 9,687,027 B2* | 6/2017 | Poston .................. A24F 47/008 |
| 9,713,346 B2 | 7/2017 | Hon |
| 2001/0032647 A1 | 10/2001 | Schuster et al. |
| 2002/0037316 A1 | 3/2002 | Weers et al. |
| 2003/0051728 A1 | 3/2003 | Lloyd et al. |
| 2003/0056790 A1 | 3/2003 | Nichols et al. |
| 2003/0064052 A1 | 4/2003 | Waters et al. |
| 2003/0070555 A1 | 4/2003 | Reyhanloo |
| 2003/0108342 A1 | 6/2003 | Sherwood et al. |
| 2004/0020500 A1 | 2/2004 | Wrenn et al. |
| 2004/0025865 A1 | 2/2004 | Nichols et al. |
| 2004/0050383 A1 | 3/2004 | Cox et al. |
| 2004/0065324 A1 | 4/2004 | Pivinski |
| 2004/0079368 A1* | 4/2004 | Gupta .................. A61M 11/041 128/203.12 |
| 2004/0084044 A1 | 5/2004 | Childers et al. |
| 2004/0099266 A1 | 5/2004 | Cross et al. |
| 2004/0129280 A1 | 7/2004 | Woodson et al. |
| 2004/0129793 A1* | 7/2004 | Nguyen ................ A61M 11/041 239/13 |
| 2004/0149737 A1 | 8/2004 | Sharpe et al. |
| 2004/0200488 A1 | 10/2004 | Felter et al. |
| 2004/0226569 A1 | 11/2004 | Yang et al. |
| 2005/0003003 A1 | 1/2005 | Basu et al. |
| 2005/0016550 A1 | 1/2005 | Katase |
| 2005/0043965 A1 | 2/2005 | Heller et al. |
| 2005/0090798 A1 | 4/2005 | Clark et al. |
| 2005/0169814 A1 | 8/2005 | Rosenthal |
| 2005/0172976 A1 | 8/2005 | Newman et al. |
| 2005/0235991 A1 | 10/2005 | Nichols et al. |
| 2005/0268911 A1* | 12/2005 | Cross ................... A61M 15/0045 128/204.17 |
| 2006/0047368 A1 | 3/2006 | Maharajh et al. |
| 2006/0070633 A1 | 4/2006 | Rostami et al. |
| 2006/0130860 A1 | 6/2006 | Cholet |
| 2006/0174899 A9 | 8/2006 | Luan et al. |
| 2006/0185687 A1 | 8/2006 | Hearn et al. |
| 2006/0196518 A1 | 9/2006 | Lik |
| 2006/0249144 A1 | 11/2006 | DeHaan et al. |
| 2007/0068523 A1 | 3/2007 | Fishman |
| 2007/0074734 A1 | 4/2007 | Braunshtyen et al. |
| 2007/0102013 A1 | 5/2007 | Adams et al. |
| 2007/0163610 A1 | 7/2007 | Lindell et al. |
| 2007/0186940 A1 | 8/2007 | Bhattacharyya et al. |
| 2007/0267031 A1 | 11/2007 | Lik |
| 2007/0267032 A1 | 11/2007 | Yansong |
| 2008/0108822 A1 | 5/2008 | King et al. |
| 2008/0138294 A1 | 6/2008 | Gonda et al. |
| 2008/0138398 A1 | 6/2008 | Gonda |
| 2008/0168987 A1 | 7/2008 | Denny et al. |
| 2008/0216828 A1 | 9/2008 | Wensley et al. |
| 2008/0216851 A1 | 9/2008 | Olegario et al. |
| 2008/0227088 A1 | 9/2008 | Albino et al. |
| 2008/0241255 A1 | 10/2008 | Rose et al. |
| 2008/0257367 A1 | 10/2008 | Paterno et al. |
| 2008/0264416 A1* | 10/2008 | Gonda ...................... A61K 9/007 128/203.15 |
| 2008/0315011 A1 | 12/2008 | Pesu |
| 2009/0004249 A1 | 1/2009 | Gonda |
| 2009/0004250 A1 | 1/2009 | Gonda |
| 2009/0005423 A1 | 1/2009 | Gonda |
| 2009/0014020 A1 | 1/2009 | Yoss et al. |
| 2009/0084865 A1 | 4/2009 | Maharajh |
| 2009/0130178 A1 | 5/2009 | Oronsky et al. |
| 2009/0133691 A1 | 5/2009 | Yamada et al. |
| 2009/0151717 A1 | 6/2009 | Bowen et al. |
| 2009/0188490 A1* | 7/2009 | Han ........................ A61M 11/041 128/200.14 |
| 2009/0196930 A1 | 8/2009 | Surber et al. |
| 2009/0230117 A1 | 9/2009 | Fernando et al. |
| 2009/0234129 A1 | 9/2009 | Comins et al. |
| 2009/0258075 A1 | 10/2009 | Hale et al. |
| 2009/0260641 A1 | 10/2009 | Monsees et al. |
| 2009/0272379 A1 | 11/2009 | Thorens et al. |

(56) References Cited

U.S. PATENT DOCUMENTS

| | | |
|---|---|---|
| 2009/0283103 A1 | 11/2009 | Nielsen et al. |
| 2010/0031968 A1 | 2/2010 | Sheikh et al. |
| 2010/0063111 A1 | 3/2010 | Lindell et al. |
| 2010/0200008 A1 | 8/2010 | Taieb |
| 2010/0236546 A1 | 9/2010 | Yamada et al. |
| 2010/0236562 A1 | 9/2010 | Hearn et al. |
| 2010/0260688 A1 | 10/2010 | Warchol et al. |
| 2010/0288293 A1 | 11/2010 | Slasli et al. |
| 2010/0294268 A1 | 11/2010 | Wensley et al. |
| 2010/0313901 A1 | 12/2010 | Fernando et al. |
| 2010/0319686 A1 | 12/2010 | Schennum |
| 2011/0005535 A1 | 1/2011 | Xiu |
| 2011/0011160 A1 | 1/2011 | Gerde |
| 2011/0011396 A1 | 1/2011 | Fang |
| 2011/0094523 A1* | 4/2011 | Thorens ............... A24F 47/008 131/194 |
| 2011/0120456 A1 | 5/2011 | Immel |
| 2011/0126848 A1 | 6/2011 | Zuber et al. |
| 2011/0147486 A1 | 6/2011 | Oliver et al. |
| 2011/0155153 A1 | 6/2011 | Thorens et al. |
| 2011/0168194 A1 | 7/2011 | Hon |
| 2011/0209717 A1 | 9/2011 | Li |
| 2011/0232654 A1 | 9/2011 | Mass |
| 2011/0233043 A1* | 9/2011 | Cross ............... A61M 15/0045 202/185.1 |
| 2011/0240013 A1 | 10/2011 | Hale et al. |
| 2011/0240022 A1 | 10/2011 | Hodges et al. |
| 2011/0265806 A1 | 11/2011 | Alarcon et al. |
| 2011/0277756 A1 | 11/2011 | Terry et al. |
| 2011/0277757 A1 | 11/2011 | Terry et al. |
| 2011/0277760 A1 | 11/2011 | Terry et al. |
| 2011/0277761 A1 | 11/2011 | Terry et al. |
| 2011/0277764 A1 | 11/2011 | Terry et al. |
| 2011/0277780 A1 | 11/2011 | Terry et al. |
| 2011/0290244 A1 | 12/2011 | Schennum |
| 2011/0290248 A1 | 12/2011 | Schennum |
| 2011/0290249 A1 | 12/2011 | Schennum |
| 2011/0290268 A1 | 12/2011 | Schennum |
| 2011/0303231 A1 | 12/2011 | Li et al. |
| 2011/0304282 A1 | 12/2011 | Li et al. |
| 2011/0309157 A1 | 12/2011 | Yang et al. |
| 2012/0006342 A1* | 1/2012 | Rose ............... A24F 47/008 131/273 |
| 2012/0042886 A1 | 2/2012 | Piskorz |
| 2012/0048266 A1 | 3/2012 | Alelov |
| 2012/0090630 A1 | 4/2012 | Lik |
| 2012/0111324 A1 | 5/2012 | Kraft et al. |
| 2012/0111347 A1 | 5/2012 | Lik |
| 2012/0145169 A1 | 6/2012 | Yangyang et al. |
| 2012/0145170 A1 | 6/2012 | O'connell |
| 2012/0160251 A1 | 6/2012 | Hammel et al. |
| 2012/0167906 A1 | 7/2012 | Gysland |
| 2012/0174914 A1 | 7/2012 | Pirshafiey |
| 2012/0186594 A1* | 7/2012 | Liu ............... A24F 47/008 131/329 |
| 2012/0199146 A1 | 8/2012 | Marangos |
| 2012/0204889 A1 | 8/2012 | Yunqiang |
| 2012/0227752 A1 | 9/2012 | Alelov |
| 2012/0227753 A1 | 9/2012 | Newton |
| 2012/0260926 A1 | 10/2012 | Martin |
| 2012/0260927 A1 | 10/2012 | Liu |
| 2012/0273589 A1 | 11/2012 | Hon |
| 2012/0279512 A1 | 11/2012 | Lik |
| 2012/0285475 A1 | 11/2012 | Liu |
| 2012/0285476 A1 | 11/2012 | Hon |
| 2012/0291791 A1 | 11/2012 | Pradeep |
| 2012/0312313 A1 | 12/2012 | Frija |
| 2012/0318882 A1 | 12/2012 | Abehasera |
| 2012/0325228 A1 | 12/2012 | Williams |
| 2013/0008457 A1 | 1/2013 | Zheng et al. |
| 2013/0008540 A1 | 1/2013 | Shah et al. |
| 2013/0019887 A1 | 1/2013 | Liu |
| 2013/0025609 A1 | 1/2013 | Liu |
| 2013/0032139 A1* | 2/2013 | Hale ............... A61K 9/0004 128/200.14 |
| 2013/0032159 A1 | 2/2013 | Capuano |
| 2013/0037041 A1 | 2/2013 | Worm et al. |
| 2013/0042865 A1 | 2/2013 | Monsees et al. |
| 2013/0056013 A1 | 3/2013 | Terry et al. |
| 2013/0068239 A1 | 3/2013 | Youn |
| 2013/0074854 A1 | 3/2013 | Lipowicz |
| 2013/0081642 A1 | 4/2013 | Safari |
| 2013/0087160 A1 | 4/2013 | Gherghe |
| 2013/0098377 A1 | 4/2013 | Borschke et al. |
| 2013/0104916 A1 | 5/2013 | Bellinger et al. |
| 2013/0118510 A1 | 5/2013 | Kaljura et al. |
| 2013/0125906 A1 | 5/2013 | Lik |
| 2013/0139833 A1 | 6/2013 | Lik |
| 2013/0139836 A1 | 6/2013 | Blick et al. |
| 2013/0140200 A1 | 6/2013 | Scatterday et al. |
| 2013/0146489 A1 | 6/2013 | Scatterday et al. |
| 2013/0152954 A1 | 6/2013 | Youn |
| 2013/0152956 A1 | 6/2013 | Von Borstel et al. |
| 2013/0153449 A1 | 6/2013 | Agirbas |
| 2013/0157995 A1 | 6/2013 | Kem et al. |
| 2013/0160764 A1 | 6/2013 | Liu |
| 2013/0160765 A1 | 6/2013 | Liu |
| 2013/0167853 A1 | 7/2013 | Liu |
| 2013/0167854 A1 | 7/2013 | Shin |
| 2013/0168880 A1 | 7/2013 | Duke |
| 2013/0169230 A1 | 7/2013 | Li et al. |
| 2013/0173293 A1 | 7/2013 | Hyde et al. |
| 2013/0173294 A1 | 7/2013 | Hyde et al. |
| 2013/0173295 A1 | 7/2013 | Hyde et al. |
| 2013/0173296 A1 | 7/2013 | Hyde et al. |
| 2013/0173297 A1 | 7/2013 | Hyde et al. |
| 2013/0180524 A1 | 7/2013 | Shahaf et al. |
| 2013/0180525 A1* | 7/2013 | Cross ............... A61M 15/0045 128/203.27 |
| 2013/0180533 A1 | 7/2013 | Kim et al. |
| 2013/0192615 A1 | 8/2013 | Tucker et al. |
| 2013/0192616 A1 | 8/2013 | Tucker et al. |
| 2013/0192617 A1 | 8/2013 | Thompson |
| 2013/0192618 A1 | 8/2013 | Li |
| 2013/0192619 A1 | 8/2013 | Tucker et al. |
| 2013/0192620 A1 | 8/2013 | Tucker et al. |
| 2013/0192621 A1 | 8/2013 | Li et al. |
| 2013/0192622 A1 | 8/2013 | Tucker et al. |
| 2013/0192623 A1 | 8/2013 | Tucker et al. |
| 2013/0199528 A1 | 8/2013 | Goodman et al. |
| 2013/0199551 A1 | 8/2013 | Le Roux et al. |
| 2013/0206154 A1 | 8/2013 | Fernando et al. |
| 2013/0213417 A1 | 8/2013 | Chong et al. |
| 2013/0213418 A1 | 8/2013 | Tucker et al. |
| 2013/0213419 A1 | 8/2013 | Tucker et al. |
| 2013/0213420 A1 | 8/2013 | Hon |
| 2013/0220315 A1 | 8/2013 | Conley et al. |
| 2013/0220316 A1 | 8/2013 | Oglesby et al. |
| 2013/0220847 A1 | 8/2013 | Fisher et al. |
| 2013/0228190 A1 | 9/2013 | Weiss et al. |
| 2013/0247924 A1 | 9/2013 | Scatterday et al. |
| 2013/0248385 A1 | 9/2013 | Scatterday et al. |
| 2013/0255675 A1 | 10/2013 | Liu |
| 2013/0255702 A1 | 10/2013 | Griffith, Jr. et al. |
| 2013/0263869 A1 | 10/2013 | Zhu |
| 2013/0276779 A1 | 10/2013 | Hale et al. |
| 2013/0276798 A1 | 10/2013 | Hon |
| 2013/0276802 A1 | 10/2013 | Scatterday et al. |
| 2013/0276804 A1 | 10/2013 | Hon |
| 2013/0284190 A1 | 10/2013 | Scatterday et al. |
| 2013/0284191 A1 | 10/2013 | Scatterday et al. |
| 2013/0284192 A1 | 10/2013 | Peleg et al. |
| 2013/0284194 A1 | 10/2013 | Newton |
| 2013/0298905 A1 | 11/2013 | Levin et al. |
| 2013/0298922 A1 | 11/2013 | Xiang et al. |
| 2013/0306064 A1 | 11/2013 | Thorens et al. |
| 2013/0306065 A1 | 11/2013 | Thorens et al. |
| 2013/0306084 A1 | 11/2013 | Flick |
| 2013/0306085 A1 | 11/2013 | Sanchez et al. |
| 2013/0312739 A1 | 11/2013 | Rome et al. |
| 2013/0312742 A1 | 11/2013 | Monsees et al. |
| 2013/0312776 A1 | 11/2013 | Newton et al. |

(56) References Cited

U.S. PATENT DOCUMENTS

| | | |
|---|---|---|
| 2013/0313139 A1 | 11/2013 | Scatterday et al. |
| 2013/0319407 A1 | 12/2013 | Liu |
| 2013/0319429 A1 | 12/2013 | Tayyarah et al. |
| 2013/0319431 A1 | 12/2013 | Cyphert et al. |
| 2013/0319435 A1 | 12/2013 | Flick |
| 2013/0319436 A1 | 12/2013 | Liu |
| 2013/0319437 A1 | 12/2013 | Liu |
| 2013/0319438 A1 | 12/2013 | Liu |
| 2013/0319439 A1 | 12/2013 | Gorelick et al. |
| 2013/0319440 A1 | 12/2013 | Capuano |
| 2013/0319989 A1 | 12/2013 | Liu |
| 2013/0319999 A1 | 12/2013 | Plojoux et al. |
| 2013/0333711 A1 | 12/2013 | Liu |
| 2013/0333712 A1 | 12/2013 | Scatterday |
| 2013/0336358 A1 | 12/2013 | Liu |
| 2013/0340750 A1 | 12/2013 | Thorens et al. |
| 2013/0340775 A1 | 12/2013 | Juster et al. |
| 2013/0340778 A1 | 12/2013 | Liu |
| 2013/0340779 A1 | 12/2013 | Liu |
| 2013/0341218 A1 | 12/2013 | Liu |
| 2013/0342157 A1 | 12/2013 | Liu |
| 2014/0000636 A1 | 1/2014 | O'connell |
| 2014/0000637 A1 | 1/2014 | O'connell |
| 2014/0000638 A1 | 1/2014 | Sebastian et al. |
| 2014/0007891 A1 | 1/2014 | Liu |
| 2014/0007892 A1 | 1/2014 | Liu |
| 2014/0014124 A1 | 1/2014 | Glasberg et al. |
| 2014/0014125 A1 | 1/2014 | Fernando et al. |
| 2014/0014126 A1 | 1/2014 | Peleg et al. |
| 2014/0020693 A1 | 1/2014 | Cochand et al. |
| 2014/0020696 A1 | 1/2014 | Liu |
| 2014/0020697 A1 | 1/2014 | Liu |
| 2014/0020699 A1 | 1/2014 | Dittrich et al. |
| 2014/0034070 A1 | 2/2014 | Schennum |
| 2014/0034071 A1 | 2/2014 | Levitz et al. |
| 2014/0048086 A1 | 2/2014 | Zhanghua et al. |
| 2014/0048444 A1 | 2/2014 | Scatterday |
| 2014/0053831 A1 | 2/2014 | Leamon et al. |
| 2014/0053856 A1 | 2/2014 | Liu |
| 2014/0053857 A1 | 2/2014 | Liu |
| 2014/0053858 A1 | 2/2014 | Liu |
| 2014/0060524 A1 | 3/2014 | Liu |
| 2014/0060525 A1 | 3/2014 | Hale et al. |
| 2014/0060527 A1 | 3/2014 | Liu |
| 2014/0060528 A1 | 3/2014 | Liu |
| 2014/0060529 A1 | 3/2014 | Zhang |
| 2014/0060532 A1 | 3/2014 | Hale et al. |
| 2014/0060552 A1 | 3/2014 | Cohen |
| 2014/0060554 A1 | 3/2014 | Collett et al. |
| 2014/0060555 A1 | 3/2014 | Chang et al. |
| 2014/0060556 A1 | 3/2014 | Liu |
| 2014/0064715 A1 | 3/2014 | Greim et al. |
| 2014/0066618 A1 | 3/2014 | Hale et al. |
| 2014/0069425 A1 | 3/2014 | Zhang |
| 2014/0072605 A1 | 3/2014 | Bennett et al. |
| 2014/0076310 A1 | 3/2014 | Newton et al. |
| 2014/0076338 A1 | 3/2014 | Kaljura et al. |
| 2014/0083442 A1 | 3/2014 | Scatterday |
| 2014/0083443 A1 | 3/2014 | Liu |
| 2014/0096781 A1 | 4/2014 | Sears et al. |
| 2014/0096782 A1 | 4/2014 | Ampolini et al. |
| 2014/0097103 A1 | 4/2014 | Cameron et al. |
| 2014/0107815 A1 | 4/2014 | Lamothe |
| 2014/0144429 A1* | 5/2014 | Wensley .......... A61M 15/06 128/200.14 |
| 2014/0190496 A1* | 7/2014 | Wensley .......... A24F 47/008 131/273 |
| 2014/0207016 A1* | 7/2014 | Addington ...... A61M 15/0036 600/538 |
| 2014/0261408 A1 | 9/2014 | DePiano et al. |
| 2014/0270729 A1 | 9/2014 | DePiano et al. |
| 2014/0270730 A1 | 9/2014 | DePiano et al. |
| 2014/0283855 A1 | 9/2014 | Hawes et al. |
| 2014/0350028 A1* | 11/2014 | Weers .......... A61K 9/0075 514/253.08 |
| 2015/0196060 A1 | 7/2015 | Wensley et al. |
| 2015/0216237 A1 | 8/2015 | Wensley et al. |
| 2016/0324212 A1* | 11/2016 | Cameron .......... A24F 47/008 |

FOREIGN PATENT DOCUMENTS

| | | |
|---|---|---|
| CN | 1541577 A | 11/2004 |
| CN | 101084801 A | 12/2007 |
| CN | 201208444 Y | 3/2008 |
| CN | 100381083 C | 4/2008 |
| CN | 101878958 A | 11/2010 |
| CN | 202014571 U | 10/2011 |
| CN | 102266125 A | 12/2011 |
| CN | 102655773 A | 9/2012 |
| CN | 202445136 U | 9/2012 |
| CN | 202941411 U | 5/2013 |
| CN | 103209728 A | 7/2013 |
| CN | 203087526 U | 7/2013 |
| CN | 203194541 U | 9/2013 |
| CN | 103504479 A | 1/2014 |
| CN | 203538366 U | 4/2014 |
| CN | 103948172 A | 7/2014 |
| CN | 203676143 U | 7/2014 |
| CN | 203748678 U | 8/2014 |
| CN | 203884698 U | 10/2014 |
| CN | 203943069 U | 11/2014 |
| CN | 203952431 U | 11/2014 |
| CN | 203952433 U | 11/2014 |
| CN | 104254356 A | 12/2014 |
| CN | 204070546 U | 1/2015 |
| CN | 204120238 U | 1/2015 |
| CN | 104323433 A | 2/2015 |
| CN | 104397880 A | 3/2015 |
| DE | 202010002041 U1 | 5/2010 |
| EP | 0174550 B1 | 1/1991 |
| EP | 0438862 B1 | 11/1994 |
| EP | 0696457 B1 | 2/1999 |
| EP | 0911041 A2 | 4/1999 |
| EP | 0615411 B1 | 7/1999 |
| EP | 0612221 B1 | 11/1999 |
| EP | 0628376 B1 | 12/1999 |
| EP | 0703734 B1 | 6/2000 |
| EP | 0640297 B1 | 10/2000 |
| EP | 0703735 B1 | 7/2001 |
| EP | 0706352 B1 | 3/2002 |
| EP | 0893071 B1 | 3/2002 |
| EP | 0951219 B1 | 11/2002 |
| EP | 0917830 B1 | 12/2002 |
| EP | 0857431 B1 | 3/2003 |
| EP | 1089712 B1 | 5/2003 |
| EP | 0822760 B1 | 6/2003 |
| EP | 0845220 B1 | 9/2003 |
| EP | 1349601 A2 | 10/2003 |
| EP | 1025397 B1 | 5/2004 |
| EP | 1154815 B1 | 7/2004 |
| EP | 1119384 B1 | 6/2005 |
| EP | 1011767 B1 | 11/2005 |
| EP | 1389137 B1 | 7/2006 |
| EP | 1322357 B1 | 1/2007 |
| EP | 1126892 B1 | 4/2007 |
| EP | 1276672 B1 | 11/2007 |
| EP | 1972215 A1 | 9/2008 |
| EP | 1618803 B1 | 12/2008 |
| EP | 2022349 A1 | 2/2009 |
| EP | 2022350 A1 | 2/2009 |
| EP | 2047880 A1 | 4/2009 |
| EP | 1736065 B1 | 6/2009 |
| EP | 1265504 B1 | 7/2009 |
| EP | 1827146 B1 | 9/2009 |
| EP | 2100525 A1 | 9/2009 |
| EP | 2110033 A1 | 10/2009 |
| EP | 2110034 A1 | 10/2009 |
| EP | 2113178 A1 | 11/2009 |
| EP | 1415677 B1 | 12/2009 |
| EP | 2143346 A1 | 1/2010 |
| EP | 1392242 B1 | 5/2010 |
| EP | 1656171 B1 | 6/2010 |
| EP | 1968406 B1 | 6/2010 |
| EP | 2201850 A1 | 6/2010 |

(56) References Cited

FOREIGN PATENT DOCUMENTS

| | | |
|---|---|---|
| EP | 2213321 A1 | 8/2010 |
| EP | 1055430 B1 | 9/2010 |
| EP | 2253233 A1 | 11/2010 |
| EP | 1556171 B1 | 12/2010 |
| EP | 2260733 A1 | 12/2010 |
| EP | 2276360 A1 | 1/2011 |
| EP | 1392381 B1 | 3/2011 |
| EP | 2316286 A1 | 5/2011 |
| EP | 2319334 A1 | 5/2011 |
| EP | 2327318 A1 | 6/2011 |
| EP | 2338360 A1 | 6/2011 |
| EP | 2338361 A1 | 6/2011 |
| EP | 2340729 A1 | 7/2011 |
| EP | 2340730 A1 | 7/2011 |
| EP | 2359705 A1 | 8/2011 |
| EP | 2378905 A1 | 10/2011 |
| EP | 2392218 A1 | 12/2011 |
| EP | 2399636 A1 | 12/2011 |
| EP | 2404515 A1 | 1/2012 |
| EP | 2408494 A1 | 1/2012 |
| EP | 2432339 A1 | 3/2012 |
| EP | 1441785 B1 | 4/2012 |
| EP | 2443946 A1 | 4/2012 |
| EP | 2454956 A1 | 5/2012 |
| EP | 2257195 B1 | 6/2012 |
| EP | 2460422 A1 | 6/2012 |
| EP | 2460423 A1 | 6/2012 |
| EP | 2460424 A1 | 6/2012 |
| EP | 2461857 A1 | 6/2012 |
| EP | 2461858 A1 | 6/2012 |
| EP | 2468116 A1 | 6/2012 |
| EP | 2468117 A1 | 6/2012 |
| EP | 2468118 A1 | 6/2012 |
| EP | 2469969 A1 | 6/2012 |
| EP | 1463883 B1 | 7/2012 |
| EP | 2481308 A1 | 8/2012 |
| EP | 2489391 A1 | 8/2012 |
| EP | 2265138 B1 | 9/2012 |
| EP | 2493342 A1 | 9/2012 |
| EP | 2503912 A1 | 10/2012 |
| EP | 2515690 A1 | 10/2012 |
| EP | 2519121 A1 | 11/2012 |
| EP | 1549440 B1 | 12/2012 |
| EP | 2381805 B1 | 12/2012 |
| EP | 1558098 B1 | 1/2013 |
| EP | 2364101 B1 | 1/2013 |
| EP | 2540173 A1 | 1/2013 |
| EP | 2543265 A2 | 1/2013 |
| EP | 2170280 B1 | 3/2013 |
| EP | 2392217 B1 | 4/2013 |
| EP | 2578095 A2 | 4/2013 |
| EP | 2580970 A1 | 4/2013 |
| EP | 2580971 A1 | 4/2013 |
| EP | 2589306 A1 | 5/2013 |
| EP | 2606756 A1 | 6/2013 |
| EP | 2493341 B1 | 7/2013 |
| EP | 2609820 A1 | 7/2013 |
| EP | 2614731 A1 | 7/2013 |
| EP | 2614732 A1 | 7/2013 |
| EP | 1489931 B1 | 8/2013 |
| EP | 2625975 A1 | 8/2013 |
| EP | 2471392 B1 | 9/2013 |
| EP | 2640205 A2 | 9/2013 |
| EP | 2641490 A1 | 9/2013 |
| EP | 2645890 A1 | 10/2013 |
| EP | 2645891 A1 | 10/2013 |
| EP | 2645892 A1 | 10/2013 |
| EP | 2649891 A1 | 10/2013 |
| EP | 2649892 A1 | 10/2013 |
| EP | 2653047 A2 | 10/2013 |
| EP | 2654469 A1 | 10/2013 |
| EP | 2654470 A1 | 10/2013 |
| EP | 2654471 A1 | 10/2013 |
| EP | 1599243 B1 | 12/2013 |
| EP | 2488054 B1 | 12/2013 |
| EP | 2668858 A1 | 12/2013 |
| EP | 2668859 A2 | 12/2013 |
| EP | 2668860 A2 | 12/2013 |
| EP | 2672848 A2 | 12/2013 |
| EP | 2675302 A1 | 12/2013 |
| EP | 1750788 B1 | 1/2014 |
| EP | 2282649 B1 | 1/2014 |
| EP | 2695531 A1 | 2/2014 |
| EP | 2696711 A2 | 2/2014 |
| EP | 2698070 A1 | 2/2014 |
| EP | 2700324 A1 | 2/2014 |
| EP | 1465693 B1 | 3/2014 |
| EP | 2519122 B1 | 4/2014 |
| EP | 2712322 A1 | 4/2014 |
| EP | 2712350 A1 | 4/2014 |
| EP | 2712511 A1 | 4/2014 |
| GB | 2357035 A | 6/2001 |
| GB | 2466758 A | 7/2010 |
| GB | 2468932 B | 8/2011 |
| GB | 2466758 B | 9/2011 |
| GB | 2488257 B | 2/2013 |
| GB | 2465247 B | 3/2013 |
| GB | 2494315 A | 3/2013 |
| GB | 2496684 A | 5/2013 |
| GB | 2497536 A | 6/2013 |
| GB | 2497616 A | 6/2013 |
| GB | 2500293 A | 9/2013 |
| GB | 2500956 A | 10/2013 |
| GB | 2500957 A | 10/2013 |
| GB | 2501671 A | 11/2013 |
| GB | 2502052 A | 11/2013 |
| GB | 2502053 A | 11/2013 |
| GB | 2502054 A | 11/2013 |
| GB | 2502055 A | 11/2013 |
| GB | 2502162 A | 11/2013 |
| GB | 2502163 A | 11/2013 |
| GB | 2502164 A | 11/2013 |
| GB | 2504075 A | 1/2014 |
| GB | 2504076 A | 1/2014 |
| GB | 2504077 A | 1/2014 |
| JP | 2004283244 A | 10/2004 |
| JP | 2005-034021 A | 2/2005 |
| KR | 20110132290 A | 12/2011 |
| KZ | 28108 B | 12/2013 |
| RU | 2297781 C2 | 4/2007 |
| WO | WO 95/01137 A1 | 1/1995 |
| WO | WO 95/27411 A1 | 10/1995 |
| WO | WO 95/27412 A1 | 10/1995 |
| WO | WO 96/32854 A2 | 10/1996 |
| WO | WO 96/36247 A1 | 11/1996 |
| WO | WO 98/16088 A1 | 4/1998 |
| WO | WO 98/17130 A1 | 4/1998 |
| WO | WO 99/20939 A1 | 4/1999 |
| WO | WO 99/20940 A1 | 4/1999 |
| WO | WO 00/21598 A1 | 4/2000 |
| WO | WO 01/82725 A1 | 11/2001 |
| WO | WO 02/43514 A1 | 6/2002 |
| WO | WO 02/051466 A2 | 7/2002 |
| WO | WO 03/012565 A1 | 2/2003 |
| WO | WO 03/013618 A1 | 2/2003 |
| WO | 03034847 A1 | 5/2003 |
| WO | WO 03/046695 A2 | 6/2003 |
| WO | WO 03/049792 A1 | 6/2003 |
| WO | WO 03/053502 A1 | 7/2003 |
| WO | WO 03/055486 A1 | 7/2003 |
| WO | WO 03/059413 A2 | 7/2003 |
| WO | WO 03/070031 A1 | 8/2003 |
| WO | WO 03/094900 A1 | 11/2003 |
| WO | WO 03/105529 A1 | 12/2003 |
| WO | WO 2004/022242 A1 | 3/2004 |
| WO | WO 2004/022243 A1 | 3/2004 |
| WO | WO 2004/041007 A2 | 5/2004 |
| WO | WO 2004/043175 A1 | 5/2004 |
| WO | WO 2004/050139 A2 | 6/2004 |
| WO | WO 2004/066762 A2 | 8/2004 |
| WO | WO 2004/080216 A1 | 9/2004 |
| WO | WO 2004/095955 A1 | 11/2004 |
| WO | WO 2004/106170 A2 | 12/2004 |
| WO | WO 2005/099494 A1 | 10/2005 |

(56) References Cited

FOREIGN PATENT DOCUMENTS

| | | |
|---|---|---|
| WO | WO 2005/120614 A1 | 12/2005 |
| WO | WO 2006/067627 A1 | 6/2006 |
| WO | WO 2006/070288 A2 | 7/2006 |
| WO | WO 2007/042941 A2 | 4/2007 |
| WO | WO 2007/078273 A1 | 7/2007 |
| WO | WO 2007/131449 A1 | 11/2007 |
| WO | WO 2007/131450 A1 | 11/2007 |
| WO | WO 2008/015441 A1 | 2/2008 |
| WO | WO 2008/069970 A2 | 6/2008 |
| WO | WO 2008/094693 A2 | 8/2008 |
| WO | WO 2009/001078 A2 | 12/2008 |
| WO | WO 2009/001082 A1 | 12/2008 |
| WO | WO 2009/001085 A2 | 12/2008 |
| WO | WO 2009/044280 A3 | 4/2009 |
| WO | WO 2009/044281 A1 | 4/2009 |
| WO | WO 2009/105919 A1 | 9/2009 |
| WO | WO 2009/112182 A1 | 9/2009 |
| WO | WO 2009/118085 A1 | 10/2009 |
| WO | WO 2009/120057 A1 | 10/2009 |
| WO | WO 2009/127401 A1 | 10/2009 |
| WO | 2009132793 A1 | 11/2009 |
| WO | WO 2009/135729 A1 | 11/2009 |
| WO | WO 2009/155734 A1 | 12/2009 |
| WO | WO 2010/003480 A1 | 1/2010 |
| WO | WO 2010/073018 A1 | 7/2010 |
| WO | WO 2010/073122 A1 | 7/2010 |
| WO | WO 2010/086074 A1 | 8/2010 |
| WO | WO 2010/090655 A1 | 8/2010 |
| WO | WO 2010/091593 A1 | 8/2010 |
| WO | WO 2010/107613 A1 | 9/2010 |
| WO | WO 2010/118644 A1 | 10/2010 |
| WO | WO 2010/133342 A1 | 11/2010 |
| WO | WO 2010/145894 A1 | 12/2010 |
| WO | WO 2011/010334 A1 | 1/2011 |
| WO | WO 2011/015825 A1 | 2/2011 |
| WO | WO 2011/015826 A1 | 2/2011 |
| WO | WO 2011/033396 A2 | 3/2011 |
| WO | WO 2011/034723 A1 | 3/2011 |
| WO | WO 2011/042212 A1 | 4/2011 |
| WO | 2011050943 A1 | 5/2011 |
| WO | WO 2011/050964 A1 | 5/2011 |
| WO | WO 2011/061130 A1 | 5/2011 |
| WO | WO 2011/063970 A1 | 6/2011 |
| WO | WO 2011/075722 A3 | 6/2011 |
| WO | WO 2011/076407 A1 | 6/2011 |
| WO | WO 2011/079932 A1 | 7/2011 |
| WO | WO 2011/079933 A1 | 7/2011 |
| WO | WO 2011/107737 A1 | 9/2011 |
| WO | WO 2011/117580 A2 | 9/2011 |
| WO | WO 2011/124033 A1 | 10/2011 |
| WO | WO 2011/127639 A1 | 10/2011 |
| WO | WO 2011/127644 A1 | 10/2011 |
| WO | WO 2011/130886 A1 | 10/2011 |
| WO | WO 2011/137453 A2 | 11/2011 |
| WO | WO 2011/146175 A2 | 11/2011 |
| WO | WO 2011/146264 A2 | 11/2011 |
| WO | WO 2011/146365 A2 | 11/2011 |
| WO | WO 2011/146372 A2 | 11/2011 |
| WO | WO 2011/146375 A2 | 11/2011 |
| WO | WO 2011/147687 A1 | 12/2011 |
| WO | WO 2011/147691 A1 | 12/2011 |
| WO | WO 2011/160788 A1 | 12/2011 |
| WO | WO 2012/019372 A1 | 2/2012 |
| WO | WO 2012/019533 A1 | 2/2012 |
| WO | WO 2012/026963 A2 | 3/2012 |
| WO | WO 2012/029064 A1 | 3/2012 |
| WO | WO 2012/039720 A1 | 3/2012 |
| WO | WO 2012/043941 A1 | 4/2012 |
| WO | WO 2012/045683 A2 | 4/2012 |
| WO | WO 2012/062619 A1 | 5/2012 |
| WO | WO 2012/065310 A1 | 5/2012 |
| WO | WO 2012/065754 A3 | 5/2012 |
| WO | WO 2012/070107 A1 | 5/2012 |
| WO | 2012085207 A1 | 6/2012 |
| WO | WO 2012/072264 A1 | 6/2012 |
| WO | WO 2012/072762 A1 | 6/2012 |
| WO | WO 2012/072790 A1 | 6/2012 |
| WO | WO 2012/081804 A2 | 6/2012 |
| WO | WO 2012/085082 A1 | 6/2012 |
| WO | WO 2012/085203 A1 | 6/2012 |
| WO | WO 2012/085205 A1 | 6/2012 |
| WO | WO 2012/088675 A1 | 7/2012 |
| WO | WO 2012/091249 A1 | 7/2012 |
| WO | WO 2012/100430 A1 | 8/2012 |
| WO | WO 2012/100523 A1 | 8/2012 |
| WO | WO 2012/109371 A2 | 8/2012 |
| WO | WO 2012/110819 A1 | 8/2012 |
| WO | WO 2012/129787 A1 | 10/2012 |
| WO | WO 2012/129812 A1 | 10/2012 |
| WO | WO 2012/133289 A1 | 10/2012 |
| WO | WO 2012/142293 A2 | 10/2012 |
| WO | WO 2012/164033 A1 | 12/2012 |
| WO | WO 2012/170424 A1 | 12/2012 |
| WO | WO 2012/173322 A1 | 12/2012 |
| WO | WO 2012/177510 A2 | 12/2012 |
| WO | WO 2013/004160 A1 | 1/2013 |
| WO | WO 2013/012157 A1 | 1/2013 |
| WO | WO 2013/014275 A2 | 1/2013 |
| WO | WO 2013/020220 A1 | 2/2013 |
| WO | WO 2013/022936 A1 | 2/2013 |
| WO | WO 2013/024263 A1 | 2/2013 |
| WO | WO 2013/025921 A1 | 2/2013 |
| WO | WO 2013/027066 A2 | 2/2013 |
| WO | WO 2013/030546 A1 | 3/2013 |
| WO | WO 2013/034039 A1 | 3/2013 |
| WO | WO 2013/034452 A1 | 3/2013 |
| WO | WO 2013/034453 A1 | 3/2013 |
| WO | WO 2013/034454 A1 | 3/2013 |
| WO | WO 2013/034455 A1 | 3/2013 |
| WO | WO 2013/034456 A1 | 3/2013 |
| WO | WO 2013/034458 A1 | 3/2013 |
| WO | WO 2013/034459 A1 | 3/2013 |
| WO | WO 2013/034460 A1 | 3/2013 |
| WO | WO 2013/040193 A2 | 3/2013 |
| WO | WO 2013/040275 A1 | 3/2013 |
| WO | WO 2013/040814 A1 | 3/2013 |
| WO | WO 2013/044537 A1 | 4/2013 |
| WO | WO 2013/045914 A1 | 4/2013 |
| WO | WO 2013/045944 A2 | 4/2013 |
| WO | WO 2013/050934 A1 | 4/2013 |
| WO | WO 2013/060607 A1 | 5/2013 |
| WO | WO 2013/060781 A1 | 5/2013 |
| WO | WO 2013/060827 A1 | 5/2013 |
| WO | WO 2013/064600 A1 | 5/2013 |
| WO | WO 2013/064690 A1 | 5/2013 |
| WO | WO 2013/075439 A1 | 5/2013 |
| WO | WO 2013/076098 A3 | 5/2013 |
| WO | WO 2013/076750 A1 | 5/2013 |
| WO | WO 2013/083631 A1 | 6/2013 |
| WO | WO 2013/083634 A1 | 6/2013 |
| WO | WO 2013/083635 A1 | 6/2013 |
| WO | WO 2013/083636 A1 | 6/2013 |
| WO | WO 2013/083638 A1 | 6/2013 |
| WO | WO 2013/083963 A1 | 6/2013 |
| WO | WO 2013/088230 A1 | 6/2013 |
| WO | WO 2013/089358 A1 | 6/2013 |
| WO | WO 2013/089551 A1 | 6/2013 |
| WO | WO 2013/091251 A1 | 6/2013 |
| WO | WO 2013/091252 A1 | 6/2013 |
| WO | WO 2013/093469 A2 | 6/2013 |
| WO | WO 2013/093470 A2 | 6/2013 |
| WO | WO 2013/093695 A2 | 6/2013 |
| WO | WO 2013/097158 A1 | 7/2013 |
| WO | WO 2013/098395 A1 | 7/2013 |
| WO | WO 2013/098396 A2 | 7/2013 |
| WO | WO 2013/098397 A2 | 7/2013 |
| WO | WO 2013/098398 A2 | 7/2013 |
| WO | WO 2013/102609 A2 | 7/2013 |
| WO | WO 2013/102611 A2 | 7/2013 |
| WO | WO 2013/102612 A2 | 7/2013 |
| WO | WO 2013/102613 A2 | 7/2013 |
| WO | WO 2013/102614 A2 | 7/2013 |
| WO | WO 2013/102615 A2 | 7/2013 |
| WO | WO 2013/104914 A1 | 7/2013 |

(56) References Cited

FOREIGN PATENT DOCUMENTS

| | | |
|---|---|---|
| WO | WO 2013/105739 A1 | 7/2013 |
| WO | WO 2013/110208 A1 | 8/2013 |
| WO | WO 2013/110209 A1 | 8/2013 |
| WO | WO 2013/110210 A1 | 8/2013 |
| WO | WO 2013/110211 A1 | 8/2013 |
| WO | WO 2013/110411 A2 | 8/2013 |
| WO | WO 2013/110412 A1 | 8/2013 |
| WO | WO 2013/113173 A1 | 8/2013 |
| WO | WO 2013/113174 A1 | 8/2013 |
| WO | WO 2013/113612 A1 | 8/2013 |
| WO | WO 2013/116558 A1 | 8/2013 |
| WO | WO 2013/116561 A1 | 8/2013 |
| WO | WO 2013/116567 A1 | 8/2013 |
| WO | WO 2013/116568 A2 | 8/2013 |
| WO | WO 2013/116571 A1 | 8/2013 |
| WO | WO 2013/116572 A1 | 8/2013 |
| WO | WO 2013/116983 A1 | 8/2013 |
| WO | WO 2013/120849 A1 | 8/2013 |
| WO | WO 2013/126770 A1 | 8/2013 |
| WO | WO 2013/126777 A2 | 8/2013 |
| WO | WO 2013/128176 A1 | 9/2013 |
| WO | WO 2013/128447 A1 | 9/2013 |
| WO | WO 2013/131763 A1 | 9/2013 |
| WO | WO 2013/131764 A1 | 9/2013 |
| WO | WO 2013/138384 A2 | 9/2013 |
| WO | WO 2013/138898 A1 | 9/2013 |
| WO | WO 2013/141906 A1 | 9/2013 |
| WO | WO 2013/141907 A1 | 9/2013 |
| WO | WO 2013/141994 A1 | 9/2013 |
| WO | WO 2013/141998 A2 | 9/2013 |
| WO | WO 2013/142671 A1 | 9/2013 |
| WO | WO 2013/142678 A1 | 9/2013 |
| WO | WO 2013/148810 A1 | 10/2013 |
| WO | WO 2013/149404 A1 | 10/2013 |
| WO | WO 2013/149484 A1 | 10/2013 |
| WO | WO 2013/151295 A1 | 10/2013 |
| WO | WO 2013/152873 A1 | 10/2013 |
| WO | WO 2013/155645 A1 | 10/2013 |
| WO | WO 2013/159245 A1 | 10/2013 |
| WO | WO 2013/164626 A1 | 11/2013 |
| WO | WO 2013/171206 A1 | 11/2013 |
| WO | WO 2013/171208 A1 | 11/2013 |
| WO | WO 2013/171215 A1 | 11/2013 |
| WO | WO 2013/171217 A1 | 11/2013 |
| WO | WO 2013/171221 A1 | 11/2013 |
| WO | WO 2013/173440 A1 | 11/2013 |
| WO | WO 2013/173469 A1 | 11/2013 |
| WO | WO 2013/174002 A1 | 11/2013 |
| WO | WO 2013/178767 A1 | 12/2013 |
| WO | WO 2013/178768 A1 | 12/2013 |
| WO | WO 2013/181788 A1 | 12/2013 |
| WO | WO 2013/181789 A1 | 12/2013 |
| WO | WO 2013/181796 A1 | 12/2013 |
| WO | WO 2013/181797 A1 | 12/2013 |
| WO | WO 2013/182024 A1 | 12/2013 |
| WO | WO 2013/182026 A1 | 12/2013 |
| WO | WO 2013/185357 A1 | 12/2013 |
| WO | WO 2013/185358 A1 | 12/2013 |
| WO | WO 2013/189048 A1 | 12/2013 |
| WO | WO 2013/189050 A1 | 12/2013 |
| WO | WO 2013/189052 A1 | 12/2013 |
| WO | WO 2013/190036 A1 | 12/2013 |
| WO | WO 2014/004648 A1 | 1/2014 |
| WO | WO 2014/005275 A1 | 1/2014 |
| WO | WO 2014/005614 A1 | 1/2014 |
| WO | WO 2014/008623 A1 | 1/2014 |
| WO | WO 2014/008646 A1 | 1/2014 |
| WO | WO 2014/012894 A1 | 1/2014 |
| WO | WO 2014/012905 A1 | 1/2014 |
| WO | WO 2014/012906 A1 | 1/2014 |
| WO | WO 2014/012907 A1 | 1/2014 |
| WO | WO 2014/015461 A1 | 1/2014 |
| WO | WO 2014/015463 A1 | 1/2014 |
| WO | WO 2014/015669 A1 | 1/2014 |
| WO | WO 2014/017794 A1 | 1/2014 |
| WO | WO 2014/029078 A1 | 2/2014 |
| WO | WO 2014/029103 A1 | 2/2014 |
| WO | WO 2014/029105 A1 | 2/2014 |
| WO | WO 2014/029827 A1 | 2/2014 |
| WO | WO 2014/031952 A1 | 2/2014 |
| WO | WO 2014/032275 A1 | 3/2014 |
| WO | WO 2014/032276 A1 | 3/2014 |
| WO | WO 2014/032280 A1 | 3/2014 |
| WO | WO 2014/037794 A2 | 3/2014 |
| WO | WO 2014/039308 A1 | 3/2014 |
| WO | WO 2014/040217 A1 | 3/2014 |
| WO | WO 2014/040221 A1 | 3/2014 |
| WO | WO 2014/040915 A1 | 3/2014 |
| WO | WO 2014/040988 A2 | 3/2014 |
| WO | WO 2014/043887 A1 | 3/2014 |
| WO | WO 2014/047826 A1 | 4/2014 |
| WO | WO 2014/047869 A1 | 4/2014 |
| WO | WO 2014/047948 A1 | 4/2014 |
| WO | WO 2014/047953 A1 | 4/2014 |
| WO | WO 2014/047954 A1 | 4/2014 |
| WO | WO 2014/047955 A1 | 4/2014 |
| WO | WO 2014/054035 A1 | 4/2014 |
| WO | WO 2014/058678 A1 | 4/2014 |
| WO | WO 2014/085719 A1 | 6/2014 |
| WO | 2014110119 A1 | 7/2014 |
| WO | 2014150573 A2 | 9/2014 |
| WO | 2014159982 A1 | 10/2014 |
| WO | 2014187770 A2 | 11/2014 |
| WO | WO-2015042412 A1 | 3/2015 |

OTHER PUBLICATIONS

U.S. Appl. No. 14/603,217, filed Jan. 22, 2015, Wensley, et al.
International search report and written opinion dated Jan. 12, 2015 for PCT/US2014/056578.
Office action dated Nov. 20, 2014 for U.S. Appl. No. 14/168,338.
UK office action dated Dec. 17, 2014 for GB 1321023.2.
U.S. Appl. No. 14/092,405, filed Nov. 27, 2013, Wensley et al.
U.S. Appl. No. 14/168,338, filed Jan. 30, 2014, Wensley et al.
Achieving Rapid Smoking Urge Relief and Nicotine Pharmacokinetics Through the Manipulation of the Particle Size of a Condensation Aerosol of Nicotine and Propylene Glycol. SPRNT 2014 Poster.
Aradigm, A respiratory specialty pharmaceutical company fulfiling unmet needs in pulmonary medicine. Feb. 2008.
Benowitz. Clinical pharmacology of nicotine: implications for understanding, preventing, and treating tobacco addiction. Clin Pharmacol Ther. Apr. 2008;83(4):531-41. doi: 10.1038/clpt.2008.3. Epub Feb. 27, 2008.
Brody, et al. Brain nicotinic acetylcholine receptor occupancy: effect of smoking a denicotinized cigarette. Int J Neuropsychophamiacol. Apr. 2009;12(3):305-16. doi: 10.1017/S146114570800922X. Epub Aug. 18, 2008.
Brody, et al. Cigarette smoking saturates brain alpha 4 beta 2 nicotinic acetylcholine receptors. Arch Gen Psychiatry. Aug. 2006;63(8):907-15.
CDC. Quitting smoking among adults—United States, 2001-2010. MMWR 2011;60:1513-19.
CDC. Smoking-attributable mortality, years of potential life lost, and productivity losses—United States, 2000-2004. MMWR Morb Mortal Wkly Rep. Nov. 14, 2008;57(45):1226-8.
e-Nicotine Technology announces statistically and clinically significant reductions in smoking urge in clinical trial. e-Nicotine Technology Press release. Chapel Hill, NC. Feb. 14, 2014.
e-Nicotine Technology to bring electronic nicotine delivery products to market to address key unmet needs for smokers and the public health community. e-Nicotine Technology Press release. Chapel Hill, NC. Mar. 10, 2014.
e-Nicotine Technology to present clinical data at the society for research on nicotine and tobacco. e-Nicotine Technology Press release. Chapel Hill, NC. Jan. 31, 2014.
Gonda, I. Aerosols for delivery of therapeutic and diagnostic agents to the respiratory tract. Crit Rev Ther Drug Carrier Syst. 1990;6(4):273-313.

(56) References Cited

OTHER PUBLICATIONS

Heatherton, et al. The Fagerström Test for Nicotine Dependence: a revision of the Fagerström Tolerance Questionnaire. Br J Addict. Sep. 1991;86(9):1119-27.
Henningfield, et al. Tobacco dependence and withdrawal: science base, challenges and opportunities for pharmacotherapy. Pharmacol Ther. Jul. 2009;123(1):1-16. Epub Apr. 8, 2009.
Houezec. Role of nicotine pharmacokinetics in nicotine addiction and nicotine replacement therapy: a review. Int J Tuberc Lung Dis. Sep. 2003;7(9):811-9.
International search report and written opinion dated Mar. 26, 2012 for PCT/US2011/048782.
International search report and written opinion dated Mar. 27, 2014 for PCT/US2013/072426.
Kumar, et al. Initial Observations of Cell-Mediated Drug Delivery to the Deep Lung. Cell Transplant. 2011; 20(5): 609-618.
Office action dated Jan. 2, 2013 for U.S. Appl. No. 13/460,982.
Office action dated Apr. 17, 2014 for U.S. Appl. No. 14/168,338.
Office action dated Jun. 25, 2013 for U.S. Appl. No. 13/460,982.
Office action dated Sep. 4, 2012 for U.S. Appl. No. 13/460,982.
Patton, et al. Inhaling medicines: delivering drugs to the body through the lungs. Nat Rev Drug Discov. Jan. 2007;6(1):67-74.
Polosa, et al. Effect of an electronic nicotine delivery device (e-Cigarette) on smoking reduction and cessation: a prospective 6-month pilot study. BMC Public Health. Oct. 11, 2011;11:786.
POS4-71 Abstract: Achieving rapid smoking urge relief and nictoine pharmacokinetics through the manipulation of the particle size of a condensation aerosol of nicotine and propylene glycol. Poster Session 4. Feb. 8, 2014.
Presentation published on Apr. 16, 2014 by e-Nicotine presenting at Tobacco Products Scientific Advisory Committee Meeting (TPSAC) held from Apr. 16-18, 2014.
Presentation transcript published on Apr. 16, 2014 by e-Nicotine presenting at Tobacco Products Scientific Advisory Committee Meeting (TPSAC) held from Apr. 16-18, 2014.
Rabinowitz, et al. Fast Onset Medications through Thermally Generated Aerosols. J Pharmacol Exp Ther. May 2004;309(2):769-75. Epub Jan. 29, 2004.
Rose, et al. Pulmonary delivery of nicotine pyruvate: sensory and pharmacokinetic characteristics. Exp Clin Psychopharmacol. Oct. 2010;18(5):385-94. doi: 10.1037/a0020834.
UK search report and opinin dated Feb. 12, 2014 for GB 1321023.2.
Wayne, et al. Tobacco industry research and efforts to manipulate smoke particle size: implications for product regulation. Nicotine Tob Res. Apr. 2008;10(4):613-25. doi: 10.1080/14622200801978698.
Whitten. Imaging Studies Elucidate Neurobiology of Cigarette Craving. NIDA Notes. Dec. 2008; 22(2):1-16.
WHO. Tobacco fact sheet. May 2012. Accessed Dec. 3, 2012. http://www.who.int/mediacentre/factsheets/fs339/en/index.html.
Williams. eNicotine Technologies. Taking the smoke out of smoking. OMB Meeting PPT. Dec. 18, 2013.
Zhang, et al. In Vitro Particle Size Distributions in Electronic and Conventional Cigarette Aerosols Suggest Comparable Deposition Patterns. Nicotine Tob Res. Feb. 2013; 15(2):501-508. doi: 10.1093/ntr/nts165. Epub Oct. 4, 2012.
Extended European Search Report for European Patent Application No. 15740106.8; dated Sep. 26, 2017; 9 pages.
Chinese Office Action with Search Report dated Nov. 7, 2017 for Chinese Application No. 20130071459.4, 9 pages.
Korean Intellectual Property Office, International Search Report and Written Opinion for PCT/US2014/056578, dated Jan. 12, 2015, 15 pages.
Korean Intellectual Property Office, International Search Report and Written Opinion for PCT/US2016/014158, dated May 3, 2016, 15 pages.
Japanese Patent Office, "Office Action," for JP2015-544216 with English translation, dated Sep. 15, 2017, 9 pgs.
United States Patent and Trademark Office, Office Action in U.S. Appl. No. 14/603,217; dated Jan. 24, 2018; 9 pages.
United States Patent and Trademark Office, Office Action in U.S. Appl. No. 14/168,338; dated Jul. 7, 2015; 12 pages.
United States Patent and Trademark Office, Office Action in U.S. Appl. No. 14/168,338; dated Feb. 1, 2016; 11 pages.
United States Patent and Trademark Office, Office Action in U.S. Appl. No. 14/168,338; dated Sep. 16, 2016, 11 pages.
United States Patent and Trademark Office, Office Action in U.S. Appl. No. 14/168,338; dated Jun. 15, 2017; 20 pages.
United States Patent and Trademark Office, Office Action in U.S. Appl. No. 14/168,338; dated Dec. 13, 2017; 11 pages.
United States Patent and Trademark Office, Office Action in U.S. Appl. No. 15/004,431; dated Mar. 22, 2018; 27 pages.
Australian Government IP Australia, Examination Report No. 1 for Australian Patent Application No. 2016209328; dated Aug. 28, 2018; 4 pages.
Rosepatent, Examination Report for Russian Federation Patent Application No. 2017128298; dated Aug. 6, 2018; 8 pages.
State Intellectual Property Office, Office Action in Chinese Application No. 201580014558.8; dated Sep. 27, 2018; 12 pages.
Canadian Patent Office, Office Action in Canadian Application No. 2,974,364; dated Sep. 18, 2018; 6 pages.

\* cited by examiner

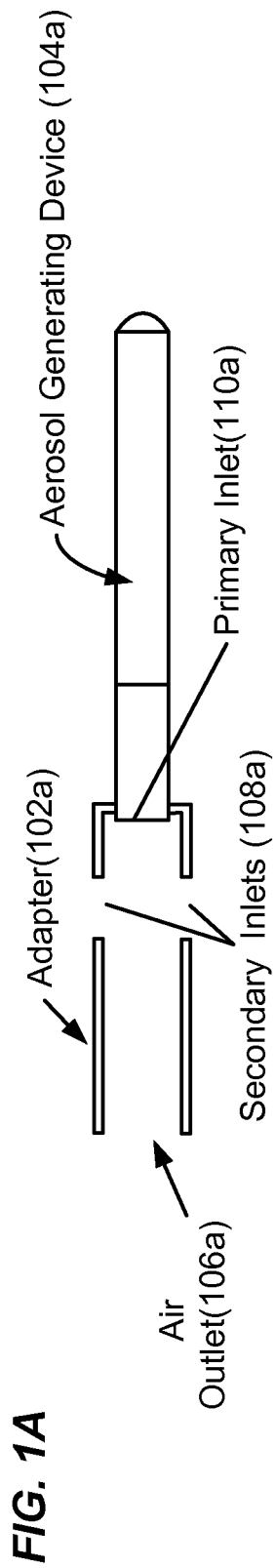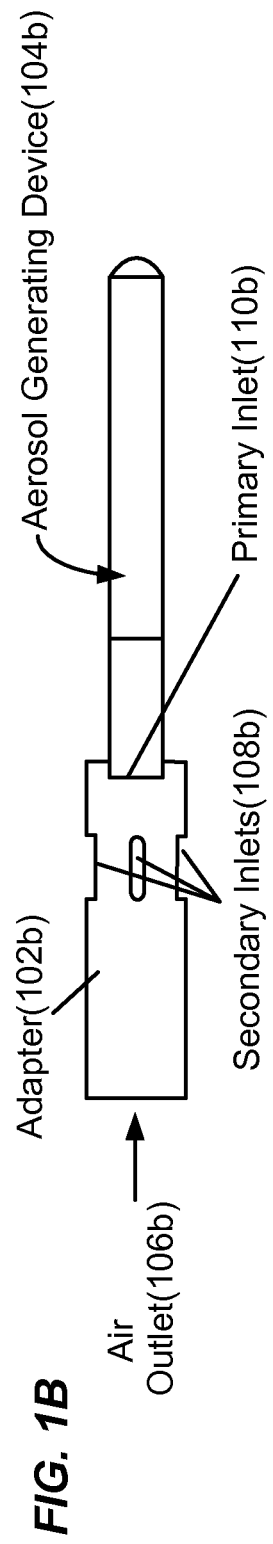
FIG. 1A
FIG. 1B

*FIG. 4*

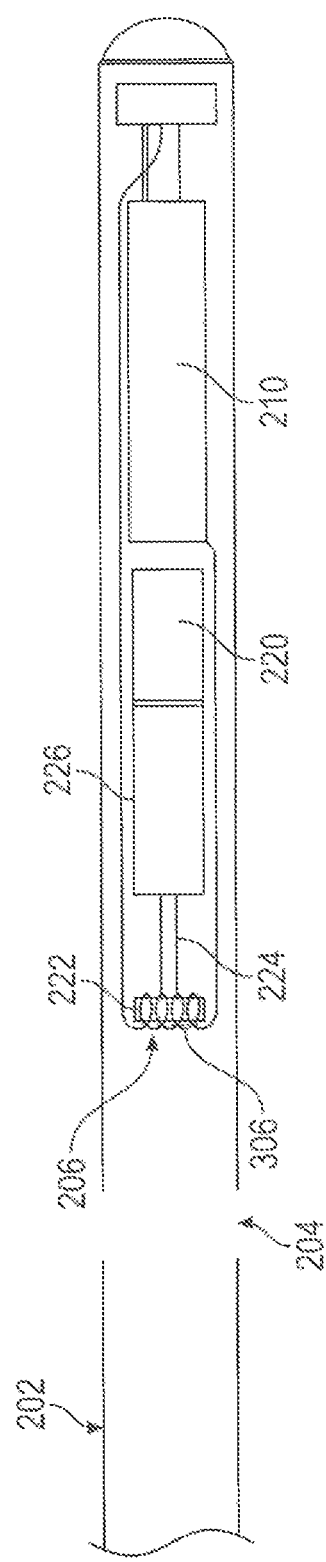

AEROSOL GENERATING DEVICE

CROSS-REFERENCE

This application claims the benefit of U.S. Provisional Application Nos. 62/048,795, filed Sep. 10, 2014 and 61/880,525, filed Sep. 20, 2013, each of which is herein incorporated by reference in its entirety.

BACKGROUND

In 2011, an estimated 19% of U.S. adults were current smokers (43.8 million people), and an estimated 950 children become addicted to smoking daily. Smokers vary widely in terms of their daily nicotine intake, ranging from "social smokers" who may only consume 1 or 2 cigarettes in the presence of friends and/or with alcohol, to heavy smokers who consume 60 or more cigarettes per day.

A number of costs are associated with smoking. For example, during 2000-2004, cigarette smoking was estimated to be responsible for $193 billion in annual health-related economic losses in the United States (nearly $96 billion in direct medical costs and an additional $97 billion in lost productivity). See Centers for Disease Control and Prevention. Smoking-Attributable Mortality, Years of Potential Life Lost, and Productivity Losses-United States, 2000-2004. *Morbidity and Mortality Weekly Report* 2008; 57(45): 1226-8. Half of smokers will die from their habit.

Nicotine from smoked cigarettes is delivered to the smoker's lung. Nicotine laden smoke particles from combustible tobacco products can be carried proximally on tar droplets (0.1-1.0 µm in diameter). These particles can be inhaled and travel to the small airways and alveoli in the deep lung. Nicotine can off-gas from the particles and defuse to, and deposit on, the alveoli wall where it can be rapidly absorbed into the blood stream.

An electronic cigarette can be used to simulate and substitute for tobacco smoking. However, electronic cigarettes can create aerosol particles in a size range too small to gravitationally settle in the alveoli of the deep lung. As a result, little or no nicotine delivered by an electronic cigarette can enter the circulatory system. Some nicotine delivered by an electronic cigarette can be slowly absorbed through the gastrointestinal (GI) tract and the buccal tissues of mouth and throat. The pharmacokinetics of nicotine delivered via electronic cigarettes can be much slower than the pharmacokinetics of nicotine delivered by smoked cigarettes; as such, electronic cigarettes can be ineffective in treating acute nicotine cravings.

A need exists to control nicotine particle size generated from an electronic nicotine delivery device (e.g., electronic cigarette) to ensure deep lung absorption of nicotine. Aerosol particles with a mass median aerodynamic diameter of about 1 µm to about 5 µm can be small enough to reach the deep lung but large enough to gravitationally settle in alveoli, which can result in a rapid pharmacokinetics (PK). With an increase in the particle size, the amount and speed of nicotine absorption can more closely mimic that of smoked cigarettes and can help to reduce nicotine cravings and more generally provide a reinforcing experience for users.

SUMMARY

In one aspect, provided herein is an aerosol generating device comprising: a. an elongated housing; b. an air flow channel comprising an inlet and an outlet, wherein the air flow channel comprises an aerosol generation region located between the inlet and the outlet; c. a liquid formulation; d. a heater element, wherein the heater element is located in the aerosol generation region, and wherein the liquid formulation is in fluid communication with the heater element; and e. a control apparatus configured to activate the heater element at an air flow rate in the aerosol generation region, wherein the device is configured to vaporize the liquid formulation upon activation of the heater element, wherein the air flow rate permits generation of aerosol particles from the vaporized liquid formulation in the air flow channel, wherein the aerosol particles comprise a diameter of from about 1 µm to about 5 µm, wherein the device is configured to pass the aerosol particles comprising a diameter of from about 1 µm to about 5 µm through the outlet of the device. In some cases, the control apparatus comprises an air-flow switch. In some cases, the air-flow switch comprises a pressure sensor. In some cases, the pressure sensor is a vacuum sensor. In some cases, the air-flow switch comprises an optical sensor. In some cases, the control apparatus further comprises a controller, wherein the controller is configured to determine the air flow rate detected by the air-flow switch. In some cases, the controller comprises a processor. In some cases, the air flow channel comprises a gas-control valve located between the inlet and the aerosol generation region, wherein the gas-control valve is configured to limit air flowing through the aerosol generation region of the air flow channel to the air flow rate that generates the condensation aerosol particles comprising a diameter of from about 1 µm to about 5 µm. In some cases, the air flow channel further comprises an internal passageway within the air flow channel, wherein the internal passageway is located in the air flow channel between the inlet and the outlet, and wherein the internal passageway comprises the aerosol generation region. In some cases, the internal passageway comprises a gas-control valve, wherein the gas-control valve is located between the inlet and the aerosol generation region and is configured to limit the first portion of air flow to the air flow rate. In some cases, the device is configured to permit a first portion of air to flow through the inlet and into the internal passageway within the air flow channel and a second portion of air to flow through the inlet and into a space between the internal passageway and the air flow channel. In some cases, the internal passageway comprises a gas-control valve, wherein the gas-control valve is located between the inlet and the aerosol generation region and is configured to limit the first portion of air flow to the air flow rate. In some cases, the first portion of air flows at the air flow rate in the aerosol generation region that generates the aerosol particles comprising a diameter of from about 1 µm to about 5 µm. In some cases, the internal passageway comprises a gas-control valve, wherein the gas-control valve is located between the inlet and the aerosol generation region and is configured to limit the first portion of air flow to the air flow rate. In some cases, the internal passageway is concentric with the air flow channel. In some cases, the control apparatus comprises the gas-control valve. In some cases, the gas-control valve is an orifice. In some cases, the device further comprises an adapter, wherein the adapter comprises a hollow main body having opposing first and second open ends, wherein the first open end is configured to couple to and surround the outlet of the air flow channel. In some cases, the adapter comprises at least one secondary air inlet between the first and second open ends of the adapter. In some cases, the at least one secondary air inlet is configured to permit a flow of entrainment air that entrains the condensation aerosol particles comprising a diameter of from about 1 μm to about 5 μm in the entrainment air flowing at a rate effective to deliver the condensation aerosol comprising a diameter of from about 1 μm to about 5 μm to a deep lung of a user of the device. In some cases, the adapter is removable. In some cases, the adapter is not removable. In some cases, the air flow channel further comprises a second air inlet, wherein the second air inlet is located between the aerosol generation region and the outlet, and wherein the second air inlet is configured to allow entrainment air into the airflow channel between the aerosol generation region and the outlet. In some cases, the entrainment air that enters the air flow channel through the second air inlet entrains the condensation aerosol particles comprising a diameter of from about 1 μm to about 5 μm in the entrainment air flowing at a rate effective to deliver the condensation aerosol particles comprising a diameter of from about 1 μm to about 5 μm to a deep lung of a user of the device. In some cases, the entrainment air flow rate effective to deliver the condensation aerosol particles comprising a diameter of from about 1 μm to about 5 μm to a deep lung of a user of the device is from about 6 liters per minute to about 40 liters per minute (LPM). In some cases, the air flow channel comprises a gas-control valve located between the inlet and the aerosol generation region, wherein the gas-control valve is configured to limit air flowing through the aerosol generation region of the air flow channel to the air flow rate that generates the condensation aerosol particles comprising a diameter of from about 1 μm to about 5 μm. In some cases, the control apparatus comprises the gas-control valve. In some cases, the air flow rate is less than 3 LPM. In some cases, the air flow rate is less than 1 LPM. In some cases, the air flow rate is up to 0.5 LPM. In some cases, the air flow rate is about 0.15 LPM. In some cases, the control apparatus is configured to activate the heater element at a vacuum of 10 inches (25.4 cm) of water or less in the outlet of the air flow channel. In some cases, the liquid formulation is stored in a reservoir. In some cases, the reservoir is located within the air flow channel. In some cases, the reservoir is located adjacent to the air flow channel. In some cases, the liquid formulation comprises nicotine. In some cases, the liquid formulation comprises at least 4.5% nicotine. In some cases, the liquid formulation comprises up to 4.5% nicotine. In some cases, the liquid formulation comprises a carrier. In some cases, the carrier comprises propylene glycol. In some cases, the carrier comprises vegetable glycerin. In some cases, the diameter is a mass median aerodynamic diameter (MMAD). In some cases, the diameter is a volume median diameter (VMD). In some cases, the heater element comprises a coil comprising electrically resistive material. In some cases, the air flow channel further comprises a vaporization nozzle, wherein the vaporization nozzle is in fluid communication with the liquid formulation and comprises the coil comprising electrically resistive material. In some cases, the coil comprising electrically resistive material is arranged on the outside of the vaporization nozzle. In some cases, the coil comprising electrically resistive material is arranged on the inside of the vaporization nozzle. In some cases, the heater element comprises a coil comprising electrically resistive material. In some cases, the air flow channel further comprises a wicking element in fluid communication with the liquid formulation and wherein the coil comprising electrically resistive material is wrapped around the wicking element. In some cases, the coil is at least partially in contact with the wicking element. In some cases, the wicking element comprises electrically resistive material. In some cases, the wicking element and the coil are formed from the same rod.

In some cases, the air flow channel is configured to permit an inhalation resistance no greater than that of a cigarette. In some cases, the air flow channel is configured to permit an inhalation resistance of from about 1 sqrt (cm-$H_2$O)/LPM to about 2.5 sqrt (cm-$H_2$O)/LPM. In some cases, the device further comprises a light emitting diode (LED), wherein the LED is activated when a user inhales from the outlet. In some cases, the device further comprises a mouthpiece surrounding the outlet of the air flow channel. In some cases, the elongated housing is cylindrical. In some cases, the aerosol particles comprise condensation aerosol particles.

In one aspect, provided herein is an aerosol generating device comprising: a. an air flow channel comprising an aerosol generation region, wherein the air flow channel comprises an inlet and an outlet; b. a substrate; c. a heater element; and d. a control apparatus configured to activate the heater element at an air flow rate less than 3 LPM in the air flow channel. In some cases, the air flow rate less than 3 LPM is detected in the aerosol generation region of the air flow channel. In some cases, the control apparatus comprises an air-flow switch. In some cases, the air-flow switch comprises a pressure sensor. In some cases, the pressure sensor is a vacuum sensor. In some cases, the air flow switch comprises an optical sensor. In some cases, the control apparatus further comprises a controller, wherein the controller is configured to determine the air flow rate detected by the air-flow switch. In some cases, the controller comprises a processor. In some cases, the air flow rate in the aerosol generation region of the air flow channel generates aerosol particles comprising a diameter of from about 1 μm to about 5 μm in the air flow channel. In some cases, the air flow channel further comprises a second air inlet, wherein the second air inlet is located between the aerosol generation region and the outlet, and wherein the second air inlet is configured to allow entrainment air into the airflow channel between the aerosol generation region and the outlet. In some cases, the entrainment air that enters the air flow channel through the second air inlet entrains the aerosol particles comprising a diameter of from about 1 μm to about 5 μm in the entrainment air flowing at a rate effective to deliver the aerosol particles comprising a diameter of from about 1 μm to about 5 μm to a deep lung of a user of the device. In some cases, the entrainment air flow rate effective to deliver the aerosol particles comprising a diameter of from about 1 μm to about 5 μm to the deep lung of a user of the device is from about 6 LPM to about 40 LPM. In some cases, the air flow channel comprises a gas-control valve located prior to the aerosol generation region, wherein the gas-control valve is configured to limit air flowing through the aerosol generation region of the air flow channel to the air flow rate of less than 3 LPM. In some cases, the control apparatus comprises the gas-control valve. In some cases, the air flow channel further comprises an internal passageway within the air flow channel, wherein the internal passageway is located in the air flow channel between the inlet and the outlet, and wherein the internal passageway comprises the aerosol generation region. In some cases, the internal passageway comprises a gas-control valve, wherein the gas-control valve is located between the inlet and the aerosol generation region and is configured to limit the first portion of air flow to the air flow rate. In some cases, the device is configured to permit a first portion of air to flow through the inlet and into the internal passageway within the air flow channel and a second portion of air to flow through the inlet and into a space between the internal passageway and the air flow channel. In some cases, the internal passageway comprises a gas-control valve, wherein the gas-control valve is located between the inlet and the aerosol generation region and is configured to limit the first portion of air flow to the air flow rate. In some cases, the first portion of air flowing through the internal passageway is at the air flow rate that generates the aerosol particles comprising a diameter of from about 1 µm to about 5 µm in the internal passageway. In some cases, the internal passageway comprises a gas-control valve, wherein the gas-control valve is located between the inlet and the aerosol generation region and is configured to limit the first portion of air flow to the air flow rate. In some cases, the gas-control valve is an orifice. In some cases, the internal passageway is concentric with the air flow channel. In some cases, the control apparatus comprises the gas-control valve. In some cases, the device further comprises an adapter, wherein the adapter comprises a hollow main body having opposing first and second open ends, wherein the first open end is configured to couple to and surround the outlet of the air flow channel. In some cases, the adapter comprises at least one secondary air inlet between the first and second open ends of the adapter. In some cases, the at least one secondary air inlet is configured to a permit a flow of entrainment air that entrains the aerosol particles comprising a diameter of from about 1 µm to about 5 µm in the entrainment air flowing at a rate effective to deliver the aerosol particles comprising a diameter of from about 1 µm to about 5 µm to a deep lung of a user of the device. In some cases, the adapter is removable. In some cases, the adapter is not removable. In some cases, the entrainment air flow rate effective to deliver the aerosol particles comprising a diameter of from about 1 µm to about 5 µm to the deep lung of a user of the device is from about 6 LPM to about 40 LPM. In some cases, the air flow channel comprises a gas-control valve located prior to the aerosol generation region, wherein the gas-control valve is configured to limit air flowing through the aerosol generation region of the air flow channel to the air flow rate of less than 3 LPM. In some cases, the control apparatus comprises the gas-control valve. In some cases, the air flow rate is less than 1 LPM. In some cases, the air flow rate is from about 0 to about 0.5 LPM. In some cases, the air flow rate is about 0.15 LPM. In some cases, the device is configured to emit the condensation aerosol particles comprising a diameter of from about 1 µm to about 5 µm through the outlet. In some cases, the diameter is a mass median aerodynamic diameter (MMAD). In some cases, the diameter is a volume median diameter (VMD). In some cases, the device further comprises an elongated housing, wherein the elongated housing comprises the air flow channel. In some cases, the elongated housing is cylindrical. In some cases, the substrate is a liquid formulation. In some cases, the liquid formulation comprises nicotine. In some cases, the liquid formulation comprises at least 4.5% nicotine. In some cases, the liquid formulation comprises up to 4.5% nicotine. In some cases, the liquid formulation comprises a carrier. In some cases, the carrier comprises propylene glycol. In some cases, the carrier comprises vegetable glycerin. In some cases, the heater element is located within the aerosol generation region. In some cases, the heater element comprises a coil comprising electrically resistive material. In some cases, the air flow channel further comprises a vaporization nozzle, wherein the vaporization nozzle is in fluid communication with the liquid formulation and comprises the coil comprising electrically resistive material. In some cases, the coil comprising electrically resistive material is outside of the vaporization nozzle. In some cases, the coil comprising electrically resistive material is inside of the vaporization nozzle. In some cases, the heater element comprises a coil comprising electrically resistive material. In some cases, the air flow channel further comprises a wicking element in fluid communication with the liquid formulation and wherein the coil comprising electrically resistive material is wrapped around the wicking element. In some cases, the coil is at least partially in contact with the wicking element. In some cases, the wicking element comprises electrically resistive material. In some cases, the wicking element and the coil are formed from the same rod. In some cases, the air flow channel is configured to permit an inhalation resistance no greater than that of a cigarette. In some cases, the air flow channel is configured to permit an inhalation resistance of from about 1 sqrt (cm-H2O)/LPM to about 2.5 sqrt (cm-H2O)/LPM. In some cases, the aerosol particles comprise condensation aerosol particles.

In one aspect, provided herein is an aerosol generating device comprising: a. an elongated housing; b. an air flow channel, wherein the air flow channel comprises an inlet and an outlet; c. a substrate; d. a heater element, wherein the heater element is located within an aerosol generation region of the air flow channel located between the inlet and the outlet, wherein a cross-sectional area of the aerosol generation region is configured to produce aerosol particles comprising a diameter of from about 1 µm to about 5 µm; and e. an adapter, wherein the adapter surrounds the first outlet of the airflow channel, and wherein the adapter comprises a second air inlet and a second outlet, wherein the second air inlet is configured to permit a flow of air that entrains the aerosol particles comprising a diameter of from about 1 µm to about 5 µm exiting the first outlet in air flowing at a rate effective to deliver the aerosol particles comprising a diameter of from about 1 µm to about 5 µm to a deep lung of a user upon inhalation through the second outlet. In some cases, the rate effective to deliver the aerosol particles comprising a diameter of from about 1 µm to about 5 µm to the deep lung of a subject upon inhalation through the second outlet is from about 10 to about 40 LPM. In some cases, the diameter is a mass median aerodynamic diameter (MMAD). In some cases, the diameter is a volume median diameter (VMD). In some cases, the adapter is removable. In some cases, the adapter is not removable. In some cases, the air flow channel comprises a gas-control valve located upstream to the aerosol generation region, wherein the gas-control valve is configured to limit air flowing through the aerosol generation region of the air flow channel to the air flow rate. In some cases, the substrate is a liquid formulation. In some cases, the liquid formulation is stored in a reservoir. In some cases, the reservoir is located within the air flow channel. In some cases, the reservoir is located adjacent to the air flow channel. In some cases, the liquid formulation comprises nicotine. In some cases, the liquid formulation comprises at least 4.5% nicotine. In some cases, the liquid formulation comprises up to 4.5% nicotine. In some cases, the liquid formulation comprises a carrier. In some cases, the carrier comprises propylene glycol. In some cases, the carrier comprises vegetable glycerin. In some cases, the aerosol particles comprise condensation aerosol particles.

In one aspect, provided herein is a method for delivering an agent to a user, the method comprising: a. producing aerosol particles with a diameter of about 1 µm to about 5 µm in an aerosol generating device, wherein the aerosol generating device comprises: i. an air flow channel comprising an inlet, an outlet, and an aerosol generation region; ii. a liquid formulation comprising an agent; iii. a heater element within the aerosol generation region, wherein the heater element is in fluid communication with the liquid formulation; and iv.

a control apparatus configured to activate the heater element at an air flow rate through the aerosol generation region of the air flow channel, wherein producing the aerosol particles comprises vaporizing the liquid formulation upon activation of the heater element; and b. delivering the aerosol particles comprising a diameter of about 1 μm to about 5 μm to a user of the device. In some cases, the control apparatus comprises an air-flow switch. In some cases, the air-flow switch comprises a pressure sensor. In some cases, the pressure sensor is a vacuum sensor. In some cases, the air flow switch comprises an optical sensor. In some cases, the control apparatus further comprises a controller, wherein the controller is configured to determine the air flow rate detected by the air-flow switch. In some cases, the controller comprises a processor. In some cases, the method further comprises entraining the aerosol particles comprising a diameter of about 1 μm to about 5 μm in entrainment air at an entrainment air flow rate effective to deliver the aerosol particles to a deep lung of the user, wherein the entrainment air enters the air flow channel through a secondary air inlet located between the aerosol generation region and the outlet of the air flow channel. In some cases, the entrainment air flow rate effective to deliver the aerosol particles to the deep lung of the user upon inhalation is from about 6 LPM to about 40 LPM. In some cases, the diameter is a mass median aerodynamic diameter (MMAD). In some cases, the diameter is a volume median diameter (VMD). In some cases, the air flow rate is less than 3 LPM. In some cases, the air flow rate is less than 1 LPM. In some cases, the air flow rate is up to about 0.5 LPM. In some cases, the air flow rate is about 0.15 LPM. In some cases, the liquid formulation comprising the agent is stored in a reservoir. In some cases, the reservoir is located within or adjacent to the air flow channel. In some cases, the agent comprises nicotine. In some cases, the agent comprises at least 4.5% nicotine. In some cases, the agent comprises up to 4.5% nicotine. In some cases, the liquid formulation comprises a carrier. In some cases, the carrier comprises propylene glycol. In some cases, the carrier comprises vegetable glycerin. In some cases, the aerosol particles are condensation aerosol particles.

In one aspect, provided herein is a kit comprising: a. an aerosol generating device comprising an elongated housing, a substrate, and a heater element, wherein the aerosol generating device is configured to be activated by an air flow rate over or around the heater element that is effective for generating aerosol particles comprising a diameter of from about 1 μm to about 5 μm; and b. an adapter for coupling to an outlet of the elongated housing, wherein the adapter comprises: i. a hollow main body having first and second open ends, wherein the first open end comprises an air outlet and the second open end is configured to couple to the outlet of the elongated housing; and ii. a flow modulation element configured to modulate a flow of the aerosol from the aerosol generating device into a deep lung of a user upon inhalation through the first open end of the adapter. In some cases, the kit further comprises instructions. In some cases, the diameter is a mass median aerodynamic diameter (MMAD). In some cases, the diameter is a volume median diameter (VMD). In some cases, the adapter is removable. In some cases, the adapter is not removable. In some cases, the air flow rate is less than 3 LPM. In some cases, the air flow rate is less than 1 LPM. In some cases, the air flow rate is from up to about 0.5 LPM. In some cases, the air flow rate is about 0.15 LPM. In some cases, the flow modulation element comprises at least one secondary air inlet between the first and second open ends of the adapter. In some cases, the at least one secondary air inlet comprises a surface comprising a semi-porous material. In some cases, the at least one secondary air inlet comprises a plurality of air inlets. In some cases, when the adapter is coupled to the aerosol generating device, the adapter is configured to modulate an entrainment air flow rate, wherein the entrainment air flow rate is about 6 LPM to about 40 LPM. In some cases, the aerosol particles comprise condensation aerosol particles.

In one aspect, provided herein is an aerosol generating device, the device comprising an elongated housing comprising: a. a reservoir comprising a liquid substrate comprising nicotine and a carrier; b. an air flow channel comprising: i. a first air inlet; ii. a heater element, wherein the heater element comprises a coil wrapped around a wick element, wherein the coil and wick element are made of an electrically resistive material that when heated vaporizes the liquid substrate comprising nicotine and a carrier that is delivered onto the heater element; iii. a tube located within the air flow channel; wherein the tube is in fluid communication with the reservoir and the heater element; and iv. an outlet, wherein the heater element is located in an aerosol generation region of the air flow channel between the inlet and the outlet, and wherein the device is configured to emit a condensation aerosol comprising nicotine and a carrier from the outlet; v. a second air inlet, wherein the second air inlet is located between the aerosol generation region and the outlet; c. a pump connected to the tube, wherein the pump is configured to deliver the liquid substrate comprising nicotine and the carrier through the tube onto the heater element; d. an air flow switch, wherein the air flow switch is configured to activate the heater element at an air flow rate through the aerosol generating region of less than 1 LPM; and e. a power supply, wherein the power supply is in electrical communication with the heater element and the air flow switch.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Novel features are set forth with particularity in the appended claims. A better understanding of the features and advantages will be obtained by reference to the following detailed description that sets forth illustrative embodiments, in which the principles are utilized, and the accompanying drawings of which:

FIG. 1A illustrates an internal view of a system comprising a removable mouthpiece coupled to an aerosol generating device (e.g., electronic cigarette).

FIG. 1B illustrates an external view of a system comprising a removable mouthpiece coupled to an aerosol generating device (e.g., electronic cigarette).

FIG. 4 illustrates an aerosol generating device system in remote communication with user devices through a network.

FIG. 5 illustrates another embodiment of a heater element for an aerosol generating device as provided herein.

DETAILED DESCRIPTION

I. Overview

Figure 2:
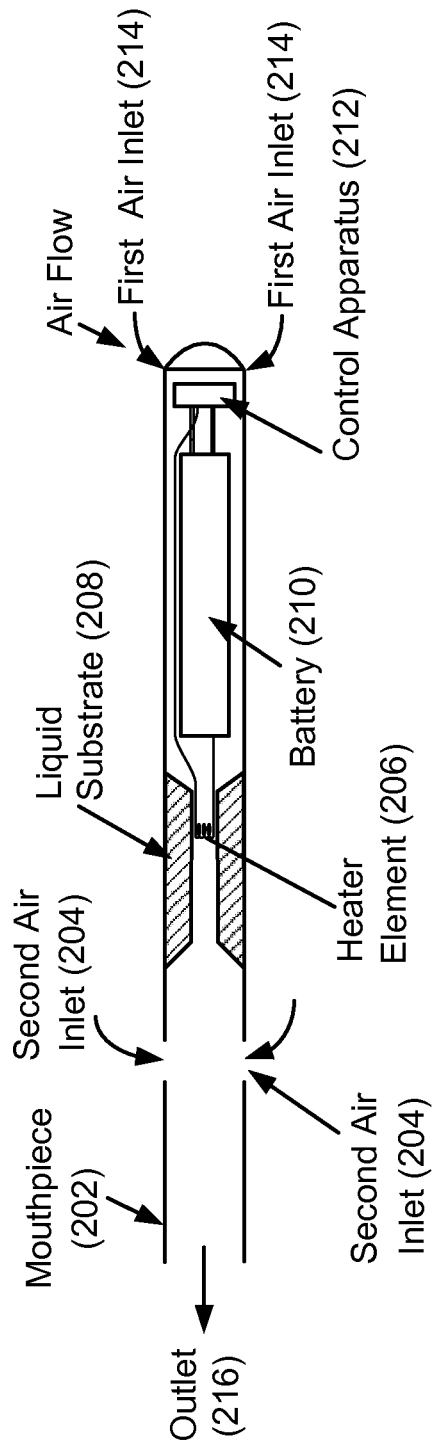
FIG. 2 illustrates a schematic of an aerosol generating device (e.g., electronic cigarette) with a modified trip point.

Provided herein are devices, kits, systems, and methods for electronic delivery of an agent (e.g., nicotine) for facilitating deep lung delivery and rapid pharmacokinetics of the agent, and for facilitating reduction of nicotine cravings in a user. Devices described herein can have a variety of combinations of features. Examples of features of devices described herein include apparatus for transporting and/or storing a substrate (e.g., liquid formulation) within a device, types and configurations of elements for vaporizing substrate (e.g., liquid formulation), electronics for communication within a device, power supply to activate a device, apparatus for "tripping" or "triggering" a device, and configuration and dimensions of one or more passageways for movement of air within a device. Properties of devices that can be affected by the design of a device include the size of aerosol particles produced by the device and the internal resistance to draw by a user of a device.

Devices described herein can generate aerosol particles comprising an agent (e.g., nicotine) at a known and consistent size at a flow rate suitable for delivery of the agent to the deep lung of a user of the device. Devices, kits, systems, and methods provided herein can generate nicotine aerosol particle sizes such that the amount and speed of nicotine absorption permitted by the devices, kits, systems, and methods more closely mimic the amount and speed of nicotine absorption achieved using smoked cigarettes (e.g., combustible tobacco articles) as compared to the amount and speed of nicotine absorption permitted by conventional electronic cigarettes (e.g., non-combustible electronic smoking articles).

The devices, kits, systems, and methods provided herein can modulate delivery of aerosol particles to the deep lung of a user. The respiratory tract of a user can include the upper airways, including the oropharynx and larynx, followed by the lower airways, which include the trachea followed by bifurcations into the bronchi and bronchioli. The upper and lower airways can be called the conductive airways. The terminal bronchioli then divide into respiratory bronchioli which then lead to the ultimate respiratory zone, the alveoli, or deep lung. See Gonda, I. Aerosols for delivery of therapeutic and diagnostic agents to the respiratory tract," *Critical Reviews in Therapeutic Drug Carrier Systems* 6:273-313 (1990); see also U.S. Pat. No. 7,435,408 B2 and U.S. Pat. No. 6,254,854 B1. The deep lung, or alveoli, can be the primary target of inhaled therapeutic aerosols for systemic delivery. The particle size for deep lung delivery can range from about 1 to about 3 microns in diameter for optimal deposition efficiency. Smaller particles can reach the alveoli but can be quickly expelled during exhalation. See e.g., Kumar, A. Initial Observations of Cell-Mediated Drug Delivery to the Deep Lung, *Cell Transplantation* 20:609-610 (2011).

A user of the devices, kits, systems, and methods provided herein can be a smoker. The user can also be referred to as a subject. The user or subject can be a human. The smoker can be a new smoker, a trough maintainer smoker, an intermittent smoker, a light smoker, a weight-loss smoker, a heavy smoker, or a very heavy smoker. An intermittent smoker can be an individual who does not smoke every day. A light smoker can be an individual who smokes 1 to 9 cigarettes per day. A moderate smoker can be an individual who smokes 10 to 19 cigarettes a day. A heavy smoker can be an individual who smokes 20 to 29 cigarettes per day. A very heavy smoker can be an individual who smokes 30 or more cigarettes per day. The user of the devices, kits, systems, and methods provided herein can use the device, kits, systems, and methods provided herein to transition away from the use of tobacco or nicotine containing smoking products or devices.

Provided herein is an aerosol generating device, wherein the aerosol generating device can generate nicotine aerosol particles of an optimum size for delivery to the deep lung. In some cases, the aerosol generating device is an electronic cigarette. The electronic cigarette can be a modified electronic cigarette. The aerosol particles can be any of the sizes provided herein. In some cases, the aerosol particles comprise a diameter of from about 1 μm to about 5 μm. In some cases, the aerosol particles can comprise a mass median aerodynamic diameter (MMAD) of from about 1 μm to about 5 μm. In some cases, the aerosol particles can comprise a volume median diameter (VMD) of from about 1 μm to about 5 μm. The aerosol particles can have a geometric standard deviation (GSD) of less than 2. The aerosol particles can have a geometric standard deviation (GSD) of from about 1 to about 2. The aerosol particles can have a geometric standard deviation (GSD) of about 1. The aerosol generating devices provided herein can generate aerosol particles with sizes optimal for deep lung delivery by controlling the linear flow rate for a carrier gas (e.g., air) over a heater element within a device provided herein, wherein a substrate (e.g., liquid nicotine solution) is vaporized upon delivery to or onto the heater element. The linear flow rate for a carrier gas (e.g., air) over the heater upon vaporization of the substrate (e.g., liquid nicotine solution) affects the particle size of the aerosol particles produced by vapor condensation, with more rapid flow rates dilute the vapor such that it condenses into smaller particles. In other words the particle size distribution of the aerosol can be determined by the concentration of the substrate vapor during condensation. This vapor concentration can, in turn, be determined by the extent to which flow of carrier gas (e.g., air) over the surface of the heater element dilutes the vaporized substrate (e.g. liquid nicotine solution). To achieve smaller or larger particles, the flow rate of a carrier gas (e.g., air) through an aerosol generation region of the device comprising the heater element can be altered by (i) modifying (increase or decrease) flow rate through the use of a valve, and/or (ii) modifying the cross-sectional area of the region of the device comprising the heater element (e.g., aerosol generation region) to increase or decrease linear carrier gas (e.g., air) velocity for a given volumetric flow rate.

In some cases, an aerosol generating device (e.g., electronic cigarette) is configured to have a low, or lowered, trip point relative to a trip point used in a conventional electronic cigarette. A trip point can be a flow rate (or vacuum applied to a mouthpiece which results in a flow rate) at which electrical current is applied to a heater element in an aerosol generating device (e.g., electronic cigarette). The trip point can be controlled by a control apparatus that detects and responds to an air flow rate at which aerosol particles with a desired diameter as provided herein are generated. The control apparatus can detect and be responsive to the air-flow rate in an airway of an aerosol generating device as provided herein. The air-flow rate detected can be in an aerosol generation region of the aerosol generating device (e.g., electronic cigarette). The control apparatus can comprise a flow switch (e.g., air flow switch). The flow switch can comprise a sensor and a processor or microprocessor. The flow switch can be in electrical communication with a heater element. The heater element can be any heater element as provided herein. The electrical communication can be direct or indirect. In some cases, the flow switch is in direct electrical communication a heater element such that activation of the flow switch causes direct activation of the heater element. The flow switch can comprise a processor (or microprocessor). In some cases, the flow switch is in indirect electrical communication with a heater element, wherein activation of the flow switch sends a signal to a processor (or microprocessor), wherein the processor (or microprocessor) then causes activation of the heater element. The flow switch can be activated by a user inhaling from an outlet of an aerosol generating device as provided herein. In some cases, a flow switch in an aerosol generating device as provided herein is located at an end of the device opposite from an outlet end (e.g., mouthpiece) of the device. The end comprising the flow switch can comprise an inlet for a carrier gas (e.g., air). The flow switch can also be referred to as a breath actuation or activation switch. The trip point can be set to a specific flow rate or a range of flow rates by using a flow switch with desired properties. The trip point can be less than 3 liters per minute (LPM). The trip point can be less than 1 LPM. The trip point can be between 0 and 0.5 LPM. The trip point can be up to 0.5 LPM. The desired properties can be a diaphragm material with a specific modulus of elasticity, distance between electrical contacts or diameter of diaphragm between electrical contacts. The diaphragm can be composed of material with a lower modulus as compared to conventional or commercially available electronic cigarettes. The distance between electrical contacts can be shortened such that the diaphragm can connect the electrical contacts at a reduced flow rate as compared to conventional or commercially available electronic cigarettes. The diaphragm can have an increased diameter as compared to conventional or commercially available electronic cigarettes thus facilitating contact between electrical contacts at a reduced or lower trip point than conventional electronic cigarette. The diaphragm can be made from an elastomeric material or thin metal material. The elastomeric material can be a synthetic rubber (e.g., Hypalon X), plastic, thermoset plastic, thermoplastic, or combinations or mixtures thereof. The elastomeric material can be polytetrafluorethylene, chlorosulfonated polyethylene, silicone, fluorosilicone, fluorocarbon, vinyl methyl silicone (VMQ), nitriles, neoprene, fluoroelastomers, ethylene propylene diene monomers (EPDM), or various combinations or mixtures thereof. The elastomeric material can comprise a chemically resistant layer. The elastomeric material can be cured (e.g., with heat and pressure) or uncured. In some cases, a breath actuation or air-flow switch that has a sufficiently low trip point using a Hall effect or change in capacitance can be used. A Hall effect can be production of a voltage difference across an electrical conductor transverse to both an electric current in the conductor and an external magnetic field applied at right angles to the current upon application of the magnetic field.

In some cases, an aerosol generating device (e.g., electronic cigarette) is configured to have an elongated housing, wherein the elongated housing comprises an air flow channel comprising an inlet and an outlet. The air flow channel can comprise a heater element. The heater element can be located in an aerosol generation region of the air flow channel. The heater element can be located outside of an aerosol generation region of the air flow channel. In some cases, an aerosol generating device (e.g., electronic cigarette) is configured to have a second inlet, wherein the second inlet is configured to deliver a carrier gas (e.g., air) downstream of the aerosol generation region and upstream of the outlet of the air flow channel. The second inlet can be a plurality of inlets. The second inlet can be in the elongated housing and be configured to allow outside air into the air flow channel. The second inlet can be connected to a bypass channel, wherein the second inlet is in a wall of the air flow channel, wherein the air flow channel is internal to the elongated housing. The inlet of the air flow channel can be configured to permit entry of outside air, wherein a portion of the air flows through the aerosol generation region of the air flow channel as well as through the bypass channel, wherein air flowing through the bypass channel enters the air flow channel through the second inlet downstream of the aerosol generation region and upstream of the outlet of the air flow channel. The second inlet in an aerosol generating device (e.g., electronic cigarette) as provided herein can modulate or facilitate a flow of the aerosol into a deep lung of a user upon inhalation of the aerosol by the user through the outlet of the air flow channel. In some cases, the second inlet modulates flow of an aerosol by increasing the flow rate of the aerosol as it exits an aerosol generation region. In some cases, the second inlet modulates flow of an aerosol by entraining the aerosol generated in an aerosol generation region in air with an increased flow rate as it exits the aerosol generating device (e.g., electronic cigarette).

Provided herein is an aerosol generating device (e.g., electronic cigarette) configured to have an elongated housing, wherein the elongated housing comprises an air flow channel comprising an inlet and an outlet. The air flow channel can comprise a heater element. The heater element can be located in an aerosol generation region of the air flow channel. The heater element (206) may comprise a coil (306) wrapped around a wick element (222), wherein the coil and wick element are made of an electrically resistive material that when heated vaporizes the liquid comprising nicotine and a carrier that is delivered onto the heater element. A tube (224) is located within the air flow channel; wherein the tube (224) is in fluid communication with the reservoir (220) and the heater element (206). A pump (226) is connected to the tube, wherein the pump is configured to deliver the liquid comprising nicotine and the carrier through the tube onto the heater element. The aerosol generation region of an aerosol generating device (e.g., electronic cigarette) as provided herein can have a cross-sectional area that permits generation of aerosol particles comprising a diameter of about 1 m to about 5 μm. The cross-sectional area can be configured to increase or decrease linear gas velocity for a given volumetric flow rate in the aerosol generation region. The diameter of the aerosol particles can be a mass median aerodynamic diameter (MMAD) of about 1 μm to about 5 μm. In some cases, the diameter of the aerosol particles can be a volumetric median diameter (VMD) of about 1 μm to about 5 μm.

Also provided herein is an adapter configured for coupling to an outlet end of an aerosol generation device, e.g., electronic cigarette. The adaptor can comprise a mouthpiece. In some cases, the adapter is removably coupled to the aerosol generation device. The adapter can comprise a continuous channel (e.g., hollow main body) comprising a first open end and a second open end, wherein the first open end can be an outlet and the second open end can be a primary inlet configured to couple to the outlet end of an aerosol generating device (e.g., electronic cigarette). The aerosol generating device can be any electronic cigarette. In some cases, the aerosol generating device is an electronic cigarette, wherein the electronic cigarette is modified or configured to produce aerosol particles with a diameter of about 1 μm to about 5 μm. In some cases, the aerosol generating device is an electronic cigarette, wherein the electronic cigarette is modified or configured to produce aerosol particles with a mass median aerodynamic diameter (MMAD) of about 1 μm to about 5 μm. In some cases, the aerosol generating device is an electronic cigarette, wherein the electronic cigarette is modified or configured to produce aerosol particles with a volumetric median diameter (VMD) of about 1 μm to about 5 μm. The adapter can modulate or facilitate a flow of the aerosol into a deep lung of a subject upon inhalation of the aerosol by the subject through the outlet of the adapter following coupling of the primary inlet of the adapter to the outlet end of an aerosol generating device (e.g., electronic cigarette). In some cases, the adapter modulates flow of an aerosol by increasing the flow rate of the aerosol as it exits an aerosol generating device (e.g., electronic cigarette). In some cases, the mouthpiece modulates flow of an aerosol by entraining the aerosol generated in an aerosol generating device in air with an increased flow rate as it exits the aerosol generating device (e.g., electronic cigarette). Also provided herein are systems and kits comprising an adapter and an aerosol generating device, e.g., electronic cigarette. The aerosol generating device, e.g., electronic cigarette, can be configured to have a trip point (or trigger point) lower than a trip point of a conventional electronic cigarettes. The trip point can be less than 3 liters per minute (LPM). The trip point can be less than 1 LPM. The trip point can be between 0 and 0.5 LPM. The trip point can be up to 0.5 LPM. In some cases, a trip point of an aerosol generating device (e.g., electronic cigarette) is controlled by an air flow switch. In some cases, an air flow switch in an aerosol generating device as provided herein is located at an end of the device opposite from an outlet end (e.g., mouthpiece) of the device. The end comprising the air flow switch can comprise an inlet for a carrier gas (e.g., air). In some cases, an air flow switch in an aerosol generating device as provided herein comprises a diaphragm. The diaphragm can be configured to react or move in response to a flow rate (or a vacuum pressure associated with the flow rate) in the device that generates an aerosol with a select size. In some cases, the diaphragm is activated at a select flow rate (or a vacuum pressure associated with the flow rate) in an aerosol generation region in the device. The select size can be a select diameter. The select diameter can be from about 1 μm to about 5 μm. The select diameter can be an MMAD or a VMD. The diaphragm material can have a lower modulus than a conventional electronic cigarette.

In some cases, a distance between electrical contacts in a switch in a control apparatus in an aerosol generating device as provided herein is less than a distance between electrical contacts in a conventional electronic cigarette. In some cases, a diameter of a diaphragm of an aerosol generating device is greater than a diameter of a diaphragm of a conventional electronic cigarette thus shortening the distance between electrical contacts in a switch comprising the diaphragm.

An aerosol generating device, e.g., electronic cigarette, can be configured to permit introduction of a carrier gas (e.g., air) for entraining an aerosol generated in the aerosol generating device that permits delivery of the aerosol to the deep lung of a user of the device. Carrier gas (e.g., air) can be introduced, e.g., by a second inlet in an aerosol generating device, e.g., electronic cigarette. In some cases, a carrier gas is provided through an adapter. In some cases, a carrier gas (e.g., air) modulates flow of an aerosol by increasing the flow rate of the aerosol as it exits an aerosol generating device (e.g., electronic cigarette). In some cases, flow of an aerosol is modulated by entraining the aerosol generated in an aerosol generating device in air with an increased flow rate as it exits the aerosol generating device (e.g., electronic cigarette).

In one aspect, provided herein is an aerosol generating device comprising an elongated cylindrical housing comprising an inlet for a carrier gas (e.g., air) at a first end of the housing and a mouthpiece at a second end of the housing such that the inlet and the mouthpiece define an air flow channel. The housing can further comprise an air flow switch, a heater element, and a liquid formulation comprising nicotine. The air-flow switch can be configured to activate the heater element at a flow rate of carrier gas (e.g., air) through the air flow channel of less than 3 LPM. In some cases, the flow rate is about 0.15 LPM. The air-flow switch can comprise a diaphragm with a modulus of elasticity responsive to a flow rate less than 3 LPM. The air-flow switch can comprise a diaphragm with a modulus of elasticity responsive to a flow rate of about 0.15 LPM. The diaphragm can serve to connect electrical contacts in electrical communication with the heater element in response to the flow rate. In some cases, the diaphragm comprises a length or diameter such that an air flow rate as provided herein causes the diaphragm to form a complete circuit that serves to activate the heater element. In some cases, the flow rate is about 0.15 LPM. In some cases, the flow rate is less than 3 LPM. In some cases, the flow rate is less than 1 LPM. The flow rate through the air flow channel generates a condensation aerosol in the device comprising a diameter of from about 1 μm to about 5 μm. The heater element can comprise an electrically resistive wire wrapped around a wicking element. The wicking element can be in fluid communication with the liquid formulation comprising nicotine. The liquid formulation can be stored in a reservoir or soaked in a porous substrate. The housing can further comprise a light emitting diode (LED) at the first end of the housing. The housing can further comprise an additional inlet or a plurality of additional inlets located between the heater element and the mouthpiece. The additional inlet(s) can permit entry of entrainment air to entrain the aerosol in a total flow rate effective to deliver the aerosol to the deep lung of a user of the device. The housing can be from about 150 mm to about 180 mm in length. The housing can have an external diameter of from about 5 mm to about 30 mm. The diameter can vary along the length of the device. The diameter can be the same along the length of the device.

In some cases, method, systems, and kits provided herein comprise a non-electronic delivery device.

Also provided herein are methods for delivering aerosol particles comprising a diameter of about 1 μm to about 5 μm using an aerosol generating device (e.g., electronic cigarette). In some cases, a method comprises providing an aerosol generating device (e.g., electronic cigarette), wherein the aerosol generating device comprises an air flow channel comprising an inlet, an outlet, a heater element, an aerosol forming substrate, and a control apparatus. In some cases, methods provided herein further comprise emitting aerosol particles from the aerosol generating device, wherein the aerosol particles comprise a diameter of from about 1 μm to about 5 μm. An aerosol forming substrate can be a liquid. The substrate can comprise a pharmaceutically active agent. The pharmaceutically active agent can be nicotine. The control apparatus can comprise an air-flow switch. The air-flow switch can be in electrical communication with the heater element. The air-flow switch can be configured to trip or activate the heater element when a predetermined air flow rate is reached in an aerosol generation region of the aerosol generating device. The predetermined air-flow rate can be less than 3 LPM. The predetermined air flow rate can be less than 1 LPM. The predetermined air flow rate can be up to about 0.5 LPM. The predetermined air flow rate can be about 0.15 LPM. The aerosol generating device can be configured to transport or delivering the aerosol particles to the deep lung of a user of the device. In some cases, a second inlet is configured to deliver carrier gas (e.g., air) that entrains aerosol generated in an aerosol generation region of a device. In some cases, a second inlet is located in a wall of an air flow channel, wherein the second inlet is located between the heater element and the outlet of the air flow channel. The wall of an air flow channel can be an external wall, wherein the second inlet permits entry of outside air. In some cases, an air flow channel is located within an external housing, wherein an second inlet permits entry of carrier gas (e.g., air) from a bypass channel, wherein the bypass channel is configured to flow carrier gas (e.g., air) that entrains an aerosol generated in the aerosol generation region of the air flow channel downstream of the aerosol generation region prior to the outlet of the air flow channel. In some cases, a method comprises providing an aerosol generating device (e.g., electronic cigarette) comprising an adapter, wherein the adapter is coupled to the outlet of the airflow channel. The adapter can provide a second inlet downstream of the heater element configured to allow entry of air than entrains an aerosol produced by an aerosol generating device that the adapter is coupled thereto. The diameter of aerosol particles generated by methods provided herein can be a mass median aerodynamic diameter (MMAD) of about 1 µm to about 5 The diameter of aerosol particles generated by methods provided herein can be a volume median diameter (VMD) of about 1 to about 5 µm. An aerosol generated by methods provided herein can be a condensation aerosol.

II. Devices

FIG. 2 illustrates an embodiment of an aerosol generating device for generating an aerosol with a particle size conducive for deep lung delivery and rapid pharmacokinetics. The aerosol can be generated from a liquid substrate (208). The liquid substrate (208) can comprise an agent (e.g., nicotine). The aerosol generating device can be an electronic cigarette. The aerosol generating device can be an electronic delivery device for an agent (e.g., nicotine) that is not an electronic cigarette. In some cases, as depicted in FIG. 2, an aerosol generating device comprises an elongated housing with an air flow channel comprising a first air inlet (214) at a first end, and a mouthpiece (202) with an outlet (216) for air and aerosol generated within the device. In this embodiment, the air flow channel of the elongated housing in FIG. 2 further comprises second air inlets (204), a heater element (206), the liquid substrate (208), a battery (210), and a control apparatus (212) used to regulate the creation of an aerosol. A region of the elongated housing comprising the heater element (206) can be an aerosol generation region. An elongated housing can be cylindrical in dimension. The liquid substrate (208) can further comprise a carrier as provided herein. The liquid substrate (208) can be housed in a reservoir. A reservoir housing the liquid substrate (208) can be located within the air flow channel of an elongated housing. In the embodiment in FIG. 2, the second air inlets (204) are located between the heater element (206) and the outlet (216). The battery (210) can be rechargeable and/or replaceable. The control apparatus (212) in FIG. 2 can be an air-flow switch. The air-flow switch can comprise a pressure sensor and be in electrical communication with the heater element (206). The air flow switch can comprise a diaphragm. The diaphragm can be configured to react or move in response to a flow rate (or a vacuum pressure associated with the flow rate) in an airway or passageway of the device that generates an aerosol with a select size. The diaphragm can be composed of a material with a modulus of elasticity that permits the diaphragm to react or move in response to the flow rate (or a vacuum pressure associated with the flow rate) in the aerosol generation region of the device that generates the aerosol with a size (e.g., diameter) as provided herein. In some cases, the distance between electrical contacts in the air flow switch is configured to permit the diaphragm to connect the electrical contacts at the flow rate (or a vacuum pressure associated with the flow rate) in the aerosol generation region of the device that generates the aerosol with a size (e.g., diameter) as provided herein. The size can be a diameter. The diameter can be optimal for delivery to the deep lung of a user of the device. In the aerosol generating device depicted in FIG. 2, air can enter the elongated housing through the first air inlet (214), flow past the control apparatus (212) around the battery (210) and through the portion of the housing comprising the heater element (206), wherein the air flow is at a rate that permits condensation of liquid substrate (208) vaporized by the activated heater element (206) after the liquid substrate (208) is delivered to the heater element (206). In the embodiment in FIG. 2, the air flowing through the portion of the air flow channel comprising the heater element (206) can then carry a stable concentration of condensed aerosol particles past the second inlet (204) where the condensed aerosol particles are entrained with air flowing through the second inlets (214) and subsequently the entrained condensed aerosol particles exit the air flow channel through the outlet (216). The entrainment air entering the air flow channel through the second inlets (214) can be at a flow rate that facilitates delivery of the aerosol particles to the deep lung of a user of the device. The entrainment air flow rate can be from about 6 LPM to about 40 LPM. In some cases, the entrainment air entering through the second air inlets (214) does not affect the particle size (e.g., diameter). The size (e.g., diameter) of the aerosol particles can be controlled by regulating the air flow rate through the region of the air flow channel in the elongated housing that comprises the heater element (e.g., aerosol generation region). In some cases, aerosol particles generated by a device as provided herein comprise a diameter of from about 1 to about 5 µm. The diameter can be a mass median aerodynamic diameter (MMAD) or a volume median diameter (VMD). In FIG. 2, the control apparatus can be a pressure sensor, which can detect a change in pressure when a user inhales on the mouthpiece (202). The pressure detected by the pressure sensor in FIG. 2 can be a pressure that is associated with an air flow rate conducive to the generation of aerosol particles with a diameter of from about 1 µm to about 5 µm. In FIG. 2, the control apparatus (e.g., pressure sensor) (212) can be configured to activate the heater element (206) at an air flow rate in the region of the elongated housing that comprises the heater element (206) of less than 3 liters per minute. The air flow rate that activates the heater element (206) via the control apparatus (212) can be less than 1 LPM. The air flow rate that activates the heater element (206) via the control apparatus (212) can be up to 0.5 LPM. The air flow rate that activates the heater element (206) via the control apparatus (212) can be about 0.15 LPM or less.

In some cases, a delivery device as provided herein is not electronic.

Particle Properties

A device provided herein can generate an aerosol. The aerosol can be a condensation aerosol. In some cases, an aerosol generated in an aerosol generating device as provided herein is a condensation aerosol. The aerosol can comprise particles of an optimum size for delivery to the deep lung of a user of a device as provided herein. In some cases, the device is an electronic cigarette. The electronic cigarette can generate aerosol particles of an optimum size for delivery to the deep lung. The particle size can be about, more than, less than, or at least 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, or 20 microns. The particle size can be from about 1 to about 10 microns, about 1 to about 9 microns, about 1 to about 7 microns, about 1 to 6 microns, about 1 to about 5 microns, about 1 to about 4 microns, about 1 to about 3 microns, or about 1 to about 2 microns. The particle size can be from about 0.5 to about 10 microns, about 0.5 to about 9.5 microns, about 0.5 to about 9 microns, about 0.5 to about 8.5 microns, about 0.5 to about 8 microns, about 0.5 to about 7.5 microns, about 0.5 to about 7 microns, about 0.5 to about 6.5 microns, about 0.5 to about 6 microns, about 0.5 to about 5.5 microns, about 0.5 to about 5 microns, about 0.5 to about 4.5 microns, about 0.5 to about 4.0 microns, about 0.5 to about 3.5 microns, about 0.5 to about 3 microns, about 0.5 to about 2.5 microns, about 0.5 to about 2 microns, about 0.5 to about 1.5 microns, or about 0.5 to about 1 microns. The particle size can be less than 1 micron. The particle size can be greater than 5 microns. The particle size can be less than 5 microns. The particle size can be greater than 1 micron. In some cases, the particle size is from about 1 micron to about 5 microns. In some cases, the particle size is from about 1 micron to about 3 microns. The particle size can be a mean or average. In some cases, an aerosol produced by any device as provided herein comprises a mean or average particle size. The mean can be an arithmetic or geometric mean. The particle size can be a diameter, radius, or circumference. The particle size can represent a single particle or a population of particles. The population of particles can be an aerosol or condensation aerosol produced by a device as provided herein. In some cases, the population of particles is a condensation aerosol. In some cases, the particle size is a diameter. The diameter can be a physical diameter (e.g., Feret's diameter, Martin's diameter, or equivalent projected area diameter), a fiber diameter, a Stokes' diameter, a thermodynamic diameter, a volumetric diameter, or an aerodynamic diameter. In some cases, the particle size is a volume median diameter (VMD). In some cases, the particle size is a mass median aerodynamic diameter (MMAD). In some cases, the particle size is a physical diameter (e.g., Feret's diameter, Martin's diameter, or equivalent projected area diameter). The particle size can be created at any of the flow rates for any of the devices provided herein. In some cases, an aerosol with a diameter of from about 1 micron to about 5 microns is generated in an aerosol generation area or region of an aerosol generating device as provided herein when the air flow rate through the aerosol generation area or region is no more than 0.1, 0.2, 0.3, 0.4, or 0.5 liters minute (LPM). In some cases, an aerosol with a diameter of from about 1 micron to about 5 microns is generated in an aerosol generation area or region of an aerosol generating device as provided herein when the air flow rate through the aerosol generation area or region is less than 0.15 LPM. The aerosol generating device can be an electronic cigarette. The air flow rate through the aerosol generation area or region can be the air flow rate at which the air-flow switch is tripped or triggered to activate the heater element.

A device provided herein can generate an aerosol. The aerosol can be a condensation aerosol. In some cases, an aerosol generated in an aerosol generating device (e.g., electronic cigarette) as provided herein is a condensation aerosol. The aerosol can comprise particles of an optimum size for delivery to the deep lung of a user of a device as provided herein. In some cases, the device is an electronic cigarette. The electronic cigarette can generate aerosol particles of an optimum size for delivery to the deep lung. In some cases, an aerosol or condensation aerosol produced by any device as provided herein comprises a standard deviation. In some cases, the standard deviation is for a particle size distribution of an aerosol produced by a device as provided herein. The standard deviation can be an arithmetic or geometric standard deviation (GSD). In some cases, an aerosol generated by a device as provided herein comprises a particle size distribution comprising an arithmetic standard deviation (ASD). The ASD can be about, more than, less than, or at least 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 microns. The ASD can be from about 1 to about 3, about 1 to about 2, about 0.1 to about 1, or about 0.1 to about 0.5 microns. The ASD can be between about 0.1 to about 0.5, about 0.5 to about 1, about 1 to about 1.5, about 1.5 to about 2, or about 2 to about 3 microns. The ASD can be between 0.1 and 0.5, 0.5 and 1, 1 and 1.5, 1 and 2, 1 and 3, 1.5 and 2, 1.5 and 3, or 2 and 3 microns. In one embodiment, the ASD is less than 2 microns. In some cases, an aerosol generated by a device as provided herein comprises a particle size distribution comprising a GSD. The GSD can be about, more than, less than, or at least 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3. The GSD can be from about 1 to about 3, about 1 to about 2. The GSD can be between about 1 to about 1.5, about 1.5 to about 2, or about 2 to about 3. The GSD can be between 1 and 1.5, 1 and 2, 1 and 3, 1.5 and 2, 1.5 and 3, or 2 and 3. In one embodiment, the GSD is less than 2. In one embodiment, the GSD is less than 1.5. The particle size can be a diameter, radius, or circumference. The diameter can be a physical diameter (e.g., Feret's diameter, Martin's diameter, or equivalent projected area diameter), a fiber diameter, a Stokes' diameter, a thermodynamic diameter, a volumetric diameter, or an aerodynamic diameter. In some cases, the diameter of the particles of an aerosol generated by a device as provided herein comprises an ASD. In some cases, the diameter of the particles of an aerosol generated by a device as provided herein comprises a GSD. In some cases, a device provided herein generates an aerosol comprising an MMAD of from about 1 µm to about 5 µm with a GSD of less than 2. In some cases, a device provided herein generates an aerosol comprising an MMAD of from about 1 µm to about 3 µm with a GSD of less than 2. In some cases, a device provided herein generates an aerosol comprising an MMAD of from about 1 µm to about 5 µm with a GSD of from about 1 to about 2. In some cases, a device provided herein generates an aerosol comprising an MMAD of from about 1 to about 3 μm with a GSD of from about 1 to about 2. In some cases, a device provided herein generates an aerosol comprising a VMD of from about 1 to about 5 μm with a GSD of less than 2. In some cases, a device provided herein generates an aerosol comprising a VMD of from about 1 to about 3 μm with a GSD of less than 2. In some cases, a device provided herein generates an aerosol comprising a VMD of from about 1 to about 5 μm with a GSD of from about 1 to about 2. In some cases, a device provided herein generates an aerosol comprising a VMD of from about 1 to about 3 μm with a GSD of from about 1 to about 2. The GSD can be for any of the particle sizes that can be created at any of the flow rates for any of the devices provided herein. The GSD can be around the diameter, MMAD, or VMD. In some cases, a device for generating an aerosol as provided herein generates an aerosol comprising a pharmaceutically active agent (e.g., nicotine) comprising a particle size of from about 1 microns to about 3 microns with a GSD of 1.5 at a flow rate of no more than 0.5 liters/minute (LPM). In some cases, a device for generating an aerosol as provided herein generates an aerosol comprising a pharmaceutically active agent (e.g., nicotine) comprising a particle size of from about 1 microns to about 3 microns with a GSD of 1.5 at a flow rate of 0.15 liters/minute (LPM).

The aerosol (e.g., condensation aerosol) can comprise particles of an optimum size for delivery to a deep lung of a user of a device as provided herein. In some cases, the device is an electronic cigarette. The electronic cigarette can generate aerosol particles of an optimum size for delivery to the deep lung. The aerosol can comprise a pharmaceutically active agent as provided herein (e.g., nicotine). A device provided herein can produce an aerosol wherein greater than 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the aerosol has a diameter of from about 1 μm to about 5 μm. A device provided herein can produce an aerosol wherein greater than 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the aerosol has a diameter of from about 1 μm to about 3 μm. In some cases, between 60-70%, 70-80%, 80-90%, or 90-100% of an aerosol produced by a device described herein comprises a diameter of from about 1 μm to about 5 μm. In some cases, between 60-70%, 70-80%, 80-90%, or 90-100% of an aerosol produced by a device described herein comprises a diameter of from about 1 μm to about 5 μm. In some cases, about 60 to about 70%, about 70 to about 80%, about 80 to about 90%, or about 90 to about 100% of an aerosol produced by a device described herein comprises a diameter of from about 1 μm to about 5 μm. In some cases, about 60 to about 70%, about 70 to about 80%, about 80 to about 90%, or about 90 to about 100% of an aerosol produced by a device herein comprises a diameter of from about 1 μm to about 3 μm. In some cases, a device as provided herein produces an aerosol comprising a pharmaceutically active agent (e.g., nicotine), wherein greater than 90% of the aerosol comprises a particle diameter of from about 1 μm to about 5 μm. In some cases, a device as provided herein produces an aerosol comprising a pharmaceutically active agent (e.g., nicotine), wherein greater than 90% of the aerosol comprises a particle diameter of from about 1 μm to about 3 μm. In some cases, a device as provided herein produces an aerosol comprising a pharmaceutically active agent (e.g., nicotine), wherein greater than 95% of the aerosol comprises a particle diameter of from about 1 μm to about 5 μm. In some cases, a device as provided herein produces an aerosol comprising a pharmaceutically active agent (e.g., nicotine), wherein greater than 95% of the aerosol comprises a particle diameter of from about 1 μm to about 3 μm. The particle sizes can be generated at any of the flow rates described herein for any of the devices for generating an aerosol as provided herein. In some cases, a flow rate in an aerosol generation region is no more than 0.5 LPM. In some cases, a flow rate in an aerosol generation region is 0.15 LPM. A device provided herein can produce an aerosol comprising a pharmaceutically active agent (e.g., nicotine), wherein the average mass and/or size of a particle from the aerosol is substantially greater than a particle from an aerosol produced by a conventional e-cigarette. A device provided herein can produce an aerosol comprising a pharmaceutically active agent (e.g., nicotine), wherein the average mass and/or size distribution of the aerosol is substantially greater than the average size and/or mass distribution of an aerosol produced by a conventional e-cigarette. An e-cigarette can be any conventional, commercially available e-cigarette. An e-cigarette can be an NJOY or Finiti e-cig. In one embodiment, the particle size is a diameter. In one embodiment, the particle size is a volume median diameter (VMD). In one embodiment, the particle size is a mass median aerodynamic diameter (MMAD).

An aerosol generating device (e.g., electronic cigarette) as provided herein can produce an aerosol particles at a concentration of about, more than, less than, or at least $10^5$, $5 \times 10^5$, $10^6$, $5 \times 10^6$, $10^7$, $5 \times 10^7$, $10^8$, $5 \times 10^8$, $10^9$, $5 \times 10^9$, $10^{10}$, $5 \times 10^{10}$, $10^{11}$, $5 \times 10^{11}$, $10^{12}$, $5 \times 10^{12}$ aerosol particles per cubic centimeter. An aerosol generating device (e.g., electronic cigarette) as provided herein can produce aerosol particles at a concentration of about $10^5$ to about $10^6$ aerosol particles per cubic centimeter; about $10^6$ to about $10^7$ aerosol particles per cubic centimeter; about $10^7$ to about $10^8$ aerosol particles per cubic centimeter; about $10^8$ to about $10^9$ aerosol particles per cubic centimeter; about $10^9$ to about $10^{10}$ aerosol particles per cubic centimeter; about $10^{10}$ to about $10^{11}$ aerosol particles per cubic centimeter; or about $10^{11}$ to about $10^{12}$ aerosol particles per cubic centimeter. In some cases, an aerosol generating device (e.g., electronic cigarette) as provided herein produces a stable concentration of aerosol particles. The stable concentration of aerosol particles can be generated in an aerosol generation region or area of the aerosol generating device (e.g., electronic cigarette). An aerosol generation region or area can comprise a heater element as provided herein. The heater element as provided herein can vaporize a liquid substrate or formulation delivered to the heater element or delivered onto the heater element.

In some cases, when a removable adapter as described herein is attached to an aerosol generating device (e.g., electronic cigarette) as provided herein, inhalation into the adapter does not change the size of aerosol particles produced by the aerosol generating device (e.g., electronic cigarette). The aerosol can be generated in an aerosol generation area or region of the aerosol generating device (e.g., electronic cigarette), while the adapter can provide entrainment air that does not alter the size of the aerosol particles produce in the aerosol generation are or region.

Flow Regulation

An aerosol generating device provided herein can be configured to limit a flow of a carrier gas through an air flow channel or passageway within the device to permit formation of an aerosol from a substrate. The device can be configured to limit the flow of a carrier gas through an aerosol generation region or chamber within the air flow channel or passageway. The aerosol can be a condensation aerosol. The substrate can be a liquid substrate or formulation. The substrate can comprise an agent as provided herein. In some cases, a device provided herein can be configured to limit a flow of a carrier gas through an air-flow channel/passageway or aerosol generation region/chamber to permit condensation of a vaporized liquid formulation. The carrier gas can be air. A flow of a carrier gas through an aerosol generation chamber or passageway comprising or in fluid communication with a heater element as provided herein can be limited to a flow rate effective for the formation of aerosol particles with a desired size. In some cases, an aerosol generating device (e.g., electronic cigarette) as provided herein can be configured to activate the heater element only when a flow rate effective for the formation of aerosol particles with a desired size exists in an aerosol generation region/chamber of an air flow channel in the device. An aerosol generating device can comprise a control apparatus or mechanism to regulate or control activation of a heater element. The control apparatus can be any control apparatus as provided herein. In some cases, the control apparatus is an air-flow switch in fluid communication with the air flow channel/passageway and in electrical communication with the heater element. The flow rate can be a volumetric flow rate. The size can be a diameter. The desired diameter can be from about 1 µm to about 5 µm. The desired diameter can be from about 1 µm to about 3 µm. The diameter can be a mass median aerodynamic diameter (MMAD) or a volume median diameter (VMD). The volumetric flow rate can be less than 3 liters per minute (LPM) (less than $5.001 \times 10^{-5}$ m$^3$/s). The volumetric flow rate can be less than 1 LPM (less than $1.667 \times 10^{-5}$ m$^3$/s). The volumetric flow rate can be up to 0.5 LPM (up to $8.335 \times 10^{-6}$ m$^3$/s). The volumetric flow rate can be about 0.15 LPM (about $2.5005 \times 10^{-6}$ m$^3$/s). A device can be configured to comprise a flow resistance (to inhalation) no greater than that of a combustible tobacco cigarette. A device can be configured to comprise a flow resistance (to inhalation) of about 1 to about 2.5 sqrt (cm-H$_2$O)/LPM. A device can be configured to comprise a flow resistance (to inhalation) of about 0.05 to about 0.15 sqrt (cm-H$_2$O)/LPM. A device can be configured to comprise an inhalation resistance comprising a vacuum pressure of about 1 to about 10 inches of H$_2$O (a range from about 249 Pa to about 2488 Pa).

In some cases, an aerosol generating device (e.g., electronic cigarette) as provided herein comprises a passageway, wherein the passageway comprises a first inlet and an outlet, wherein the first inlet serves as an inlet for a carrier gas (e.g., air) and the outlet serves as an outlet for the carrier gas and an aerosol generated in the passageway. The carrier gas can be air and the passageway can be an air flow channel. The passageway or air flow channel can be in a housing. In some cases, a housing defines the passageway or air flow channel, wherein the housing comprises a first inlet and an outlet. In some cases, a housing encompasses a passageway or air flow channel, wherein the passageway or air flow channel is internal to an exterior wall of the housing. A housing comprising a passageway or air flow channel can be elongated. A housing comprising a passageway or air flow channel can be cylindrical. A passageway or air flow channel can be cylindrical. In some cases, an aerosol generating device as provided herein comprises an elongated housing that comprises an air flow channel or passageway as described herein, wherein the housing and/or the air flow channel are cylindrical. A passageway or air flow channel can comprise a flow restrictor. A flow restrictor can be located at an inlet of the passageway or air flow channel. A flow restrictor can be located between an inlet and an outlet of a passageway or air flow channel. A flow restrictor can be located in a passageway or air flow channel upstream (with respect to normal air flow) to an aerosol generation region of a passageway or air flow channel, thereby limiting a flow of a carrier gas through the aerosol generation region. A flow restrictor can be an orifice, wherein the orifice comprises dimensions that limit the flow of a carrier gas (e.g., air) there-through to a rate suitable for producing aerosol particles of a desired size as described herein. A flow restrictor can be a valve. The valve can be any valve as described herein.

In some cases, an aerosol generating device (e.g., electronic cigarette) as provided herein comprises a passageway (e.g., air flow channel) comprising an inlet and an outlet, wherein the passageway (e.g., air flow channel) comprises an orifice that comprises dimensions that limit the flow of a carrier gas (e.g., air) through an aerosol generation region of the passageway (e.g., air flow channel) to a desired flow rate (e.g., a flow rate described herein) for generating aerosol particles of a desired size (e.g., a desired particle size described herein). The orifice can have a diameter of about, more than, less than, or at least 0.01, 0.012, 0.015, 0.02, 0.022, 0.025, 0.03, 0.032, 0.035, 0.04, 0.042, 0.045, 0.05, 0.052, 0.055, 0.06, 0.062, 0.065, 0.07, 0.075, 0.08, 0.085, 0.09, 0.1, 0.105, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, or 0.8 inches (a range from about 0.254 mm to about 20.32 mm). In some cases, an orifice for air that passes over, around or through a heater element has a diameter of about 0.01 to about 0.12 inches, about 0.02 to about 0.1 inches, about 0.03 to about 0.09 inches, about 0.04 to about 0.08 inches, about 0.05 to about 0.07 inches, or about 0.15 to about 3 inches (a range from about 0.254 mm to about 76.2 mm).

In some cases, an aerosol generating device (e.g., electronic cigarette) as provided herein comprises a passageway (e.g., air flow channel) comprising an inlet and an outlet, wherein the passageway (e.g., air flow channel) comprises a valve or flap configured to limit a flow of a carrier gas (e.g., air) through an aerosol generation region of the passageway (e.g., air flow channel) to a desired flow rate (e.g., a flow rate described herein) for generating aerosol particles of a desired size (e.g., a particle size described herein). A valve or flap can be disposed in or adjacent to the aerosol generation region. A valve or flap can be any valve or flap known in the art. For example, a valve or flap used to restrict or limit the flow of carrier gas (e.g., air) through the passageway or the aerosol generation region of the passageway can be a valve or flap as described in U.S. Pat. No. 7,913,688, the disclosure of which is incorporated by reference in its entirety. A valve or flap can be modulated at a specific flow rate. The flow rate that modulates the valve or flap can be a flow rate provided herein. A valve or flap can be opened at an inhalation resistance level provided herein. In some cases, a valve or flap is in electrical communication with a heater element, and the valve or flap is configured to activate the heater element when a desired flow rate (or vacuum associated with a desired flow rate) across the valve or flap is achieved. The flap can have an electrical contact on it which when deflected by the flow of air closes an electrical contact with a secondary contact that is on a fixed member some distance away from the contact on the flap. A valve or flap can be a control apparatus configured to activate a heater element.

An aerosol generating device (e.g., electronic cigarette) as provided herein can be configured to limit a flow rate of a carrier gas (e.g., air) across or through an aerosol generation region of a passageway (e.g., air flow channel) or heater element as provided herein to a flow rate of exactly, about, more than, less than, at least, or at most 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 liters per minute.

In some cases, an aerosol generating device (e.g., electronic cigarette) as provided herein comprises a passageway, wherein the passageway comprises a first inlet and an outlet, wherein the first inlet serves as an inlet for a carrier gas (e.g., air) and the outlet serves as an outlet for the carrier gas and an aerosol generated in the passageway, and the passageway (e.g., air flow channel) comprises a second inlet for the carrier gas (e.g., air). The second inlet can be located between the inlet and the outlet. In some cases, the second inlet is located between the inlet and the outlet of the passageway, and the second inlet is located between an aerosol generation region/chamber in the passageway and the outlet. An example of such a device is shown in FIG. 2. The second inlet in the passageway (e.g., air flow channel) can serve to allow air to be added to an aerosol generated and emitted by the aerosol generating device and to generate a flow rate that permits delivery of the aerosol particles to the deep lung of a user. The second inlet in an aerosol generating device (e.g., electronic cigarette) can be configured so that it does not significantly change (increase or decrease) the size of aerosol particles generated by the aerosol generating device. The second inlet can allow entry of carrier gas (e.g., air) that has a substantially laminar flow with respect to the flow of aerosol particles through the aerosol generating device after the aerosol particles have reached a stable number concentration and carry the aerosol particles through an outlet of the device. In some cases, a second inlet in an aerosol generating device is configured to allow entry of an air flow that can increase or decrease the size of aerosol particles generated by the aerosol generating device. The second inlet can allow entry of carrier gas (e.g., air) that has a substantially perpendicular or transverse flow with respect to the flow of aerosol particles through the aerosol generating device prior to the aerosol particles having reached a stable number concentration. Entry of the carrier gas through the second inlet can impact the size of aerosol particles formed prior to exit of the aerosol particles from an outlet of the device.

In some cases, an aerosol generating device as provided herein comprises a second inlet located between an inlet and an outlet in a passageway as described herein. The second inlet can be a plurality of second inlets. The plurality of second inlets can comprise about, more than, less than, or at least 1, 2, 3, 4, 5, 6, 7, 8, 9, 10, 11, 12, 13, 14, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 330, 331, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 660, 661, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 725, 750, 775, 800, 825, 850, 875, 900, 925, 950, 975, or 1000 second air inlets. The plurality of second inlets can comprise about 1 to about 9, about 1 to about 8, about 1 to about 7, about 1 to about 6, about 1 to about 5, about 1 to about 4, about 2 to about 8, about 2 to about 7, about 2 to about 6, about 2 to about 5, about 3 to about 8, about 3 to about 7, about 3 to about 6, about 4 to about 8, about 4 to about 7, about 4 to about 6, about 1 to about 10, about 5 to about 15, about 10 to about 20, about 15 to about 25, about 20 to about 30, about 25 to about 35, about 30 to about 40, about 35 to about 45, about 40 to about 50, about 45 to about 55, about 50 to about 60, about 55 to about 65, about 60 to about 70, about 65 to about 75, about 70 to about 80, about 75 to about 85, about 80 to about 90, about 85 to about 95, or about 90 to about 100 second air inlets. In some cases, an aerosol generating device as provided herein a plurality of second inlets comprises 2 second inlets. In some cases, an aerosol generating device as provided herein a plurality of second inlets comprises 3 second inlets. In some cases, an aerosol generating device as provided herein a plurality of second inlets comprises 4 second inlets. In some cases, an aerosol generating device as provided herein a plurality of second inlets comprises 5 second inlets. In some cases, an aerosol generating device as provided herein a plurality of second inlets comprises 6 second inlets. In some cases, an aerosol generating device as provided herein a plurality of second inlets comprises 8 second inlets.

The second inlet can have the shape of a curve, circle, parabola, hyperbola, polygon, concave polygon, constructible polygon, convex polygon, cyclic polygon, decagon, digon, dodecagon, nonagon, equiangular polygon, equilateral polygonhenagon, hendecagon, heptagon, hexadecagon, hexagon, Lemoine hexagon, icosagon, octagon, pentagon, regular polygon, regular decagon, regular octagon, regular pentagon, star without crossing lines, star polygon, decagram, octagram, heptagram, hexagram, pentagram, triangle, acute triangle, anticomplementary triangle, equilateral triangle, excentral triangle, isosceles triangle, medial triangle, obtuse triangle, rational triangle, right triangle, 30-60-90 triangle, isosceles right triangle, Kepler triangle, scalene triangle, reuleaux triangle, penrose tile, trapezium, isosceles trapezium, undecagon, quadrilateral, cyclic quadrilateral, tetrachord, kite, parallelogram, equilateral parallelogram, rhombus, Lozenge, rhomboid, rectangle, regular quadrilateral, square, rhombus, tangential quadrilateral, trapezoid, isosceles trapezoid, polydrafter, balbis, annulus, arbelos, disc, Archimedes' twin circles, Bankoff circle, circumcircle, excircle, incircle, nine-point circle, circular sector, circular segment, crescent, ellipse, various lemniscates, lune, oval, Reuleaux polygon, rotor, lens, vesica piscis, Reuleaux triangle, salinon, semicircle, sphere, gomboc, tomoe, magatama, triquetra, Yin-Yang, Archimedean spiral, astroid, deltoid, ellipse, super ellipse, tomahawk or any geometric shape or combination thereof.

Each of the plurality of second inlets can be of uniform or non-uniform size. Second inlets can be arranged in a random or structured pattern. One or more second inlets can be arranged in symmetrical, mirror symmetrical, rotational symmetrical, fivefold symmetrical, sixfold symmetrical, crystal symmetrical, fractal, spirals, meanders, flow, chaos, waves, dunes, bubbles, foams, tilings, cracks, spots, stripes, tiling or any additional pattern or combination thereof. In some cases, each of the plurality of second inlets is in a row.

In some cases, one or more of the plurality of second inlets comprises a surface of semi-porous or semi-permeable material such as a filter, filter paper, screen or mesh. The filter can be a 0.2 μm filter, 0.45 μm filter, 0.7 μm filter, 1.0 μm filter, 1.2 μm filter, 1.6 μm filter, or 2.7 μm filter. The filter can comprise glass microfiber, cellulose acetate, polyvinylidene difluoride (PVDF), polyethersulfone (PES), Whatman® glass microfiber filter (grade GF/A, GF/B, GF/C, GF/D, GF/F), Whatman™ 934-AH™ glass microfiber filter. The semi-porous material can comprise metal, fiber, flexible material, or ductile material. In some cases, the mesh comprises plastic. In some cases, the plastic mesh is extruded, expanded, tubular, or oriented. Plastic can be, e.g., polypropylene, polyethylene, nylon, polyvinyl chloride (PVC), or polytetrafluoroethylene (PTFE). In some cases, the mesh comprises metal. Metal mesh can be photochemically etched or electroformed (screen filter), knitted, welded, expanded, or woven from steel or other metals. In some cases, the mesh comprises fiberglass.

The second inlet or each of the plurality of second inlets can have a length of about, more than, less than, or at least 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.62, 7.75, 8, 8.25, 8.5, 8.75, 9, 9.25, 9.5, 9.75, 10, 10.25, 10.5, 10.75, 11, 11.25, 11.5, 11.75, 12, 12.25, 12.5, 12.75, 13, 13.5, 14, 14.5, 15, 15.5, 16, 16.5, 17, 17.5, 18, 18.5, 19, 19.5, 20, 21, 22, 23, 24, or 25 mm. The second inlet or each of the plurality of second inlets can have a length of about 0.10 to about 0.2 cm, about 0.2 to about 0.3 cm, about 0.3 to about 0.4 cm, about 0.4 to about 0.5 cm, about 0.5 to about 0.6 cm, about 0.6 to about 0.7 cm, about 0.7 to about 0.8 cm, about 0.8 to about 0.9 cm, about 0.7 to about 1 cm, about 0.8 to about 1 cm, about 0.9 to about 1 cm, about 0.9 to about 1.1 cm, about 1 to about 1.25 cm, about 1.25 to about 1.5 cm, about 1.5 to about 2 cm, or about 2 cm to about 2.5 cm.

The second inlet or each of the plurality of second inlets can have a width of about, more than, less than, or at least 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.62, 7.75, 8, 8.25, 8.5, 8.75, 9, 9.25, 9.5, 9.75, 10, 10.25, 10.5, 10.75, 11, 11.25, 11.5, 11.75, 12, 12.25, 12.5, 12.75, 13, 13.5, 14, 14.5, 15, 15.5, 16, 16.5, 17, 17.5, 18, 18.5, 19, 19.5, 20, 21, 22, 23, 24, or 25 mm. The second inlet or each of the plurality of second inlets can have a width of about 0.05 to about 0.1 cm, about 0.10 to about 0.2 cm, about 0.2 to about 0.3 cm, about 0.3 to about 0.4 cm, about 0.4 to about 0.5 cm, about 0.5 to about 0.6 cm, about 0.6 to about 0.7 cm, about 0.7 to about 0.8 cm, about 0.8 to about 0.9 cm, about 0.7 to about 1 cm, about 0.8 to about 1 cm, about 0.9 to about 1 cm, about 0.9 to about 1.1 cm, about 1 to about 1.25 cm, about 1.25 to about 1.5 cm, about 1.5 to about 2 cm, or about 2 cm to about 2.5 cm.

When a second inlet is a circle, the circle can have a diameter of about, more than, less than, or at least 0.1, 0.15, 0.2, 0.25, 0.3, 0.35. 0.4, 0.45, 0.5, 0.55, 0.6, 0.65, 0.7, 0.75, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.1, 1.2, 1.3, 1.4, 1.5, 1.6, 1.7, 1.8, 1.9, or 2 cm.

An external opening of the second inlet or each of the plurality of second inlets can be at a surface of an outer wall of passageway. In some cases, an external opening of the second inlet or each of the plurality of second inlets can be raised above a surface of an outer wall of a passageway by about, more than, less than, at least, or at most 0.1, 0.15, 0.2, 0.21, 0.22, 0.23, 0.24, 0.25, 0.26, 0.27, 0.28, 0.29, 0.3, 0.35, 0.4, 0.45, or 0.5 cm. An external opening of the second inlet or each of the plurality of second inlets can be raised above a surface of an outer wall of a passageway by about 0.1 to about 0.2 cm, about 0.2 to about 0.25 cm, about 0.25 to about 0.3 cm, about 0.3 to about 0.35 cm, about 0.35 to about 0.4 cm, about 0.4 to about 0.45 cm, or about 0.45 to about 0.5 cm, or about 0.1 to about 0.5 cm.

An exterior opening of the second inlet or each of the plurality of second inlets can be recessed into an outer wall of a passageway by about, more than, less than, at least, or at most 0.05, 0.075, 0.1, 0.15, 0.175, 0.2, 0.21, 0.22, 0.23, 0.24, 0.25, 0.26, 0.27, 0.28, 0.29, 0.3, 0.35, 0.4, 0.45, or 0.5 cm. An exterior opening of the second inlet or each of the plurality of second inlets can be recessed into an outer wall of a passageway by about 0.1 to about 0.2 cm, about 0.2 to about 0.25 cm, about 0.25 to about 0.3 cm, about 0.3 to about 0.35 cm, about 0.35 to about 0.4 cm, about 0.4 to about 0.45 cm, about 0.45 to about 0.5 cm, or about 0.1 to about 0.5 cm.

An interior opening of the second inlet or each of the plurality of second inlets on the passageway can be at a surface of an inner wall of a passageway. In some cases, an interior opening of the second inlet or each of the plurality of second inlets on the passageway can be raised above a surface of an inner wall of a passageway (protrude into the passageway) by about, more than, less than, at least, or at most 0.1, 0.15, 0.2, 0.21, 0.22, 0.23, 0.24, 0.25, 0.26, 0.27, 0.28, 0.29, 0.3, 0.35, 0.4, 0.45, or 0.5 cm. An interior opening of the second inlet or each of the plurality of second inlets on the passageway can be raised above a surface of an inner wall of a passageway (protrude into the passageway) by about 0.1 to about 0.2 cm, about 0.2 to about 0.25 cm, about 0.25 to about 0.3 cm, about 0.3 to about 0.35 cm, about 0.35 to about 0.4 cm, about 0.4 to about 0.45 cm, or about 0.45 to about 0.5 cm, or about 0.1 to about 0.5 cm.

An interior opening of the second inlet or each of the plurality of second inlets on the passageway can be recessed into an inner wall of the passageway by exactly, about, more than, less than, at least or at most 0.05, 0.075, 0.1, 0.15, 0.175, 0.2, 0.21, 0.22, 0.23, 0.24, 0.25, 0.26, 0.27, 0.28, 0.29, 0.3, 0.35, 0.4, 0.45, or 0.5 cm. An interior opening of one or more secondary inlets can be recessed into an inner wall of an adapter by about 0.1 to about 0.2 cm, about 0.2 to about 0.25 cm, about 0.25 to about 0.3 cm, about 0.3 to about 0.35 cm, about 0.35 to about 0.4 cm, about 0.4 to about 0.45 cm, about 0.45 to about 0.5 cm, or about 0.1 to about 0.5 cm.

Positioning of the second inlet or each of the plurality of second inlets on the passageway can be varied in order to control the performance characteristics of the device.

A second inlet or each of a plurality of second inlets on a passageway can be separated along a main axis of the passageway by about, more than, less than, at least or at most 0.1, 0.15, 0.2, 0.21, 0.22, 0.23, 0.24, 0.25, 0.26, 0.27, 0.28, 0.29, 0.3, 0.35, 0.4, 0.45, 0.5, 0.6, 0.7, 0.8, 0.9, 1, 1.5, 2, 2.5, or 3 cm. In some cases, a second inlet or each of a plurality of second inlets on a passageway are separated in any direction on a surface of the passageway by about, more than, less than, at least, or at most 0.1, 0.15, 0.2, 0.21, 0.22, 0.23, 0.24, 0.25, 0.26, 0.27, 0.28, 0.29, 0.3, 0.35, 0.4, 0.45, 0.5, 0.6, 0.7, 0.8, 0.9, 1, 2, or 3 cm.

In some cases, an aerosol generating device (e.g., electronic cigarette) as provided herein comprises a passageway, and the passageway comprises an inlet and an outlet, and the passageway is located within a housing of the device. In some cases, an aerosol generating device comprises a first passageway and a second passageway, and the first passageway comprises a first inlet and a first outlet, and the second passageway comprises a second inlet and a second outlet and is located within the first passageway. The first and second passageways can be tubular and comprise a cylindrical dimension. The second passageway can be concentric with the first passageway. In some cases, a carrier gas (e.g., air) flows through the first inlet of the first passageway, wherein a first portion of the carrier gas flows through the second inlet of the second passageway and exits the second outlet of the second passageway, while a second portion of carrier gas flows through the first passageway. The second portion of carrier gas can flow in a space within the first passageway located between the second and first passageways, thereby bypassing the second passageway. The space can be an annular space. In some cases, the second portion of carrier gas can mix with and entrain the first portion of carrier gas exiting the outlet of the second passageway. The first and second portions of carrier gas can flow in a substantially laminar fashion. The flow rate of the first portion of carrier gas flowing through the second passageway can be limited to a desired flow rate. The desired flow rate can be a flow rate effective to generate an aerosol comprising a desired size. The desired flow rate can be less than 3 liters per minute (LPM) (less than $5.001\times10^{-5}$ $m^3/s$). The desired flow rate can be less than 1 LPM (less than $1.667\times10^{-5}$ $m^3/s$). The desired flow rate can be up to 0.5 LPM (up to $8.335\times10^{-6}$ $m^3/s$). The desired flow rate can be about 0.15 LPM (about $2.5005\times10^{-6}$ $m^3/s$). The desired size can be a diameter. The desired diameter can be from about 1 μm to about 5 μm. The desired diameter can be from about 1 μm to about 3 μm. The diameter can be a mass median aerodynamic diameter (MMAD) or a volume median diameter (VMD). The flow rate of the first portion of air in the second passageway can be limited through the use of a valve or restrictive orifice as described herein. In some cases, an aerosol generating device comprising a first and second passageway as provided herein comprises an aerosol generation region within the second passageway. A heater element can be located within the second passageway. The heater element can be located within the aerosol generation region.

An aerosol generating device (e.g., electronic cigarette) as provided herein can be configured to permit a total flow rate at the outlet of a passageway (e.g., air flow channel) of exactly, about, more than, less than, or at least 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 liters per minute.

The total flow rate at the outlet can be about 1 to about 10 LPM, about 10 to about 20 LPM, about 20 to about 30 LPM, about 30 to about 40 LPM, about 40 to about 50 LPM, about 50 to about 60 LPM, about 60 to about 70 LPM, about 70 to about 80 LPM, about 80 to about 90 LPM, or about 90 to about 100 LPM when the user inhales through an outlet of the passageway of an aerosol generating device (e.g., electronic cigarette). The total flow rate at the outlet can be about 5 to about 50 LPM, about 5 to about 45 LPM, about 6 to about 40 LPM, about 10 to about 50 LPM, about 10 to about 40 LPM, about 20 to about 80 LPM, about 20 to about 100 LPM, or about 30 to about 50 LPM when the user inhales through an outlet of the passageway of an aerosol generating device (e.g., electronic cigarette). The total flow rate can be a combination of one or more flow rates. The combination of flow rates can be a combination of a flow rate exiting an outlet of the passageway of an aerosol generating device (e.g., electronic cigarette) and flow rates from a second inlet or plurality of second inlets in the passageway. The combination of flow rates can be a combination of a flow rate exiting an outlet of a first passageway of an aerosol generating device (e.g., electronic cigarette) and a flow rate from a second passageway located within a first passageway as described herein. In some cases, a second inlet or plurality of second inlets in a passageway of an aerosol generating device (e.g., electronic cigarette) permits an increase in the total flow rate of an aerosol into a mouth of a user relative to the flow rate of the aerosol at the outlet of an aerosol generating device (e.g., electronic cigarette) without a second inlet or plurality of second inlets. In some cases, a second inlet or plurality of second inlets in a passageway of an aerosol generating device (e.g., electronic cigarette) decreases the total flow rate of an aerosol into a mouth of a user relative to the flow rate of the aerosol at the outlet of the aerosol generating device (e.g., electronic cigarette) without a second inlet or plurality of second inlets in a passageway.

An aerosol generating device can comprise a passageway as described, and the passageway is configured to generate an interior air resistance (to inhalation) no greater than an inhalation resistance of a cigarette. The interior air resistance (to inhalation) can also be referred to as the inhalation resistance, resistance to draw, draft resistance, draw resistance, puff resistance or puffability. The passageway can be configured to generate an inhalation resistance with an associated vacuum of about, more than, less than, or at least 0.1, 0.2, 0.3, 0.4, 0.5, 0.6, 0.7, 0.8, 0.9, 1, 1.5, 2, 2.5, 2.54, 3, 3.5, 4, 4.5, 5, 5.5, 6, 6.5, 7, 7.5, 8, 8.5, 9, 9.5, 10, 10.5, 11, 11.5, or 12 inches of water at a flow rate of about, more than, less than, or at least 0.1, 0.5, 1, 5, 10, 15, 20, 25, 30, 35, 40, 45, 50, 55, 60, 65, 70, 75, or 80 liters per minute. The passageway can be configured to generate an inhalation resistance with an associated vacuum of about 0.1 to about 1 inches of water, about 1 to about 1.5 inches of water, about 1.5 to about 2 inches of water, about 2 to about 2.5 inches of water, about 2.5 to about 3 inches of water, about 3 to about 3.5 inches of water, about 3.5 to about 4 inches of water, about 4 to about 4.5 inches of water, about 4.5 to about 5 inches of water, about 5 to about 5.5 inches of water, about 5.5 to about 6 inches of water, about 6 to about 6.5 inches of water, about 6.5 to about 7 inches of water, about 7 to about 7.5 inches of water, about 7.5 to about 8 inches of water, about 8 to about 8.5 inches of water, about 8.5 to about 9 inches of water, about 9 to about 9.5 inches of water, about 9.5 to about 10 inches of water, about 10 to about 10.5 inches of water, about 10.5 to about 11 inches of water, about 11 to about 11.5 inches of water, about 11.5 to about 12 inches of water, about 0.25 to about 5 inches of water, about 1 to about 5 inches of water, or about 0.5 to about 4 inches of water at a flow rate of about, more than, less than, or at least 0.1, 0.5, 1, 5, 10, 15, 20, 25, 30, 35, 40, 45, 50, 55, 60, 65, 70, 75, or 80 liters per minute. The passageway can be configured to generate an inhalation resistance with an associated vacuum of about 1 to about 5 inches of water, about 5 to about 10 inches of water, about 1 to about 2 inches of water, about 1 to about 4 inches of water, about 1 to about 6 inches of water, about 1 to about 8 inches of water, about 1 to about 10 inches of water, or about 1 to about 12 inches of water at a flow rate of about, more than, less than, or at least 1, 5, 10, 15, 20, 25, 30, 35, 40, 45, 50, 55, 60, 65, 70, 75, or 80 liters per minute. The passageway can be configured to generate an inhalation resistance with an associated vacuum of about, more than, less than, or at least 0.254, 0.508, 0.762, 1.016, 1.27, 1.524, 1.778, 2.032, 2.286, 2.54, 3.81, 5.08, 6.35, 7.62, 8.89, 10.16, 11.43, 12.7, 13.97, 15.24, 16.51, 17.78, 19.05, 20.32, 21.59, 22.86, 24.13, 25.4, 26.67, 27.94, 29.21, or 30.48 cm of water at a flow rate of about, more than, less than, or at least 0.1, 0.5, 1, 5, 10, 15, 20, 25, 30, 35, 40, 45, 50, 55, 60, 65, 70, 75, or 80 liters per minute. The passageway can be configured to generate an inhalation resistance with an associated vacuum of about 0.254 to about 2.54 cm of water, about 2.54 to about 3.81 cm of water, about 3.81 to about 5.08 cm of water, about 5.08 to about 6.35 cm of water, about 6.35 to about 7.62 cm of water, about 7.62 to about 8.89 cm of water, about 8.89 to about 10.16 cm of water, about 10.16 to about 11.43 cm of water, about 11.43 to about 12.7 cm of water, about 12.7 to about 13.97 cm of water, about 13.97 to about 15.24 cm of water, about 15.24 to about 16.51 cm of water, about 16.51 to about 17.78 cm of water, about 17.78 to about 19.05 cm of water, about 19.05 to about 20.32 cm of water, about 20.32 to about 21.59 cm of water, about 21.59 to about 22.86 cm of water, about 22.86 to about 24.13 cm of water, about 24.13 to about 25.4 cm of water, about 25.4 to about 26.67 cm of water, about 26.67 to about 27.94 cm of water, about 27.94 to about 29.21 cm of water, about 29.21 to about 30.48 cm of water, about 0.635 to about 12.7 cm of water, about 2.54 to about 12.7 cm of water, or about 1.27 to about 10.16 cm of water at a flow rate of about, more than, less than, or at least 0.1, 0.5, 1, 5, 10, 15, 20, 25, 30, 35, 40, 45, 50, 55, 60, 65, 70, 75, or 80 liters per minute. The passageway can be configured to generate an inhalation resistance with an associated vacuum of about 2.54 to about 12.7 cm of water, about 12.7 to about 25.4 cm of water, about 2.54 to about 5.08 cm of water, about 2.54 to about 10.16 cm of water, about 2.54 to about 15.24 cm of water, about 2.54 to about 20.32 cm of water, about 2.54 to about 25.4 cm of water, or about 2.54 to about 30.48 cm of water at a flow rate of about, more than, less than, or at least 1, 5, 10, 15, 20, 25, 30, 35, 40, 45, 50, 55, 60, 65, 70, 75, or 80 liters per minute. Expressed differently, the passageway of an aerosol generating device as provided herein can be configured to generate an inhalation resistance no greater than 0.08 (cm $H_2O)^{1/2}$/LPM. The passageway can be configured to generate an inhalation resistance of about, more than, less than, or at least 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.25, 0.3, 0.4, 0.5, 0.6, 0.7, 0.8, 0.9, 1, 1.5, 2, or 2.5 (cm $H_2O)^{1/2}$/LPM. The passageway can be configured to generate an inhalation resistance of about 0.01 to about 0.03 (cm $H_2O)^{1/2}$/LPM, about 0.03 to about 0.05 (cm $H_2O)^{1/2}$/LPM, about 0.05 to about 0.07 (cm $H_2O)^{1/2}$/LPM, about 0.07 to about 0.09 (cm $H_2O)^{1/2}$/LPM, about 0.09 to about 0.11 (cm $H_2O)^{1/2}$/LPM, about 0.11 to about 0.13 (cm $H_2O)^{1/2}$/LPM, about 0.13 to about 0.15 (cm $H_2O)^{1/2}$/LPM, about 0.15 to about 0.17 (cm $H_2O)^{1/2}$/LPM, about 0.17 to about 0.19 (cm $H_2O)^{1/2}$/LPM, or about 0.19 to about 0.25 (cm $H_2O)^{1/2}$/LPM. In some cases, the inhalation resistance of an aerosol generating device comprising a passageway as provided herein is controlled by altering the number and/or size of a second inlet or plurality of second inlets as provided herein in the passageway.

An aerosol generating device comprising a passageway and one or more sources (e.g., second inlets or first/second passageways) of additional or bypass carrier gas (e.g. air) as provided herein can produce a mixing ratio of bypass or additional carrier gas to carrier gas flowing through the passageway of 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, or 50:1. The mixing ratio can be between 1:1 and 5:1, 5:1 and 10:1, 10:1 and 15:1, 15:1 and 20:1; 20:1 and 25:1, 25:1, and 30:1, 30:1, and 35:1, 35:1 and 40:1, 40:1 and 45:1, or 45:1 and 50:1. The mixing ratio can be about 1:1 to about 5:1, about 5:1 to about 10:1, about 10:1 to about 15:1, about 15:1 to about 20:1; about 20:1 to about 25:1, about 25:1 to about 30:1, about 30:1 to about 35:1, about 35:1 to about 40:1, about 40:1 to about 45:1, or about 45:1 to about 50:1.

Agent/Dose

An aerosol generating device can provide doses of an agent in a consistent and known amount. The aerosol generating device can be an electronic cigarette. In some cases, the variability between doses of an agent in an aerosol generating device as provided herein is no greater than ±30%. The device can have a variability between doses of an agent over the lifetime of the device that can be about or more than 1%, 2%, 3%, 4%, 5%, 6%, 7%, 8%, 9%, 10%, 11%, 12%, 13%, 14%, 15%, 16%, 17%, 18%, 19%, 20%, 30%, 31%, 32%, 33%, 34%, 35%, 36%, 37%, 38%, 39%, 40%, 41%, 42%, 43%, 44%, 45%, 46%, 47%, 48%, 49%, or 50%. A dose of an agent can about, more than, less than, or at least 1, 2, 3, 4, 4.5, 5, 6, 7, 8, 9, 10, 11, 12, 13, 14, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 94, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 µg of agent (e.g., nicotine). In some cases, a device can deliver a dose of an agent of about, more than, less than, or at least 1, 2, 3, 4, 5, 6, 7, 8, 9, 10, 11, 12, 13, 14, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 94, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg.

An aerosol generating device can provide emitted doses of an agent in a consistent and known amount. The aerosol generating device can be an electronic cigarette. An emitted dose of an agent (e.g., nicotine) can be about, more than, less than, or at least 1, 2, 3, 4, 5, 6, 7, 8, 9, 10, 11, 12, 13, 14, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 94, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µg of agent (e.g., nicotine). In some cases, an emitted dose of an agent is about, more than, less than, or at least 1, 2, 3, 4, 5, 6, 7, 8, 9, 10, 11, 12, 13, 14, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 94, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg. In some cases, an emitted dose of an agent is about 1 mg to about 100 mg, about 1 mg to about 50 mg, about 10 mg to about 50 mg, about 20 mg to about 50 mg, about 25 mg to about 50 mg, about 30 mg to about 50 mg, about 40 mg to about 50 mg, about 50 mg to about 100 mg, about 1 mg to about 25 mg, about 2 mg to about 25 mg, about 3 mg to about 25 mg, about 4 mg to about 25 mg, about 5 mg to about 25 mg, about 1 mg to about 20 mg, about 1 mg to about 20 mg, about 2 mg to about 20 mg, about 3 mg to about 20 mg, about 4 mg to about 20 mg, or about 5 mg to about 20 mg of agent. In another embodiment, a device according to any of the embodiments described herein delivers only a single emitted dose of an agent (e.g., nicotine).

In some cases, an emitted dose of an agent emitted from an aerosol generating device as provided herein can be about, more than, less than, or at least 1, 2, 3, 4, 5, 6, 7, 8, 9, 10, 11, 12, 13, 14, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 94, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the dose (or loaded dose). In some cases, the emitted dose can be between 1%-10%, 10%-20%, 20%-30%, 30%-40%, 40%-50%, 50%-60%, 60%-70%, 70%-80%, 80%-90%, or 90%-100% of the dose (or loaded dose). In some cases, the emitted dose is more than 20% of the dose (or loaded dose). In some cases, the emitted dose is less than 20% of the dose (or loaded dose). In some cases, the dose (or loaded dose) is the amount of an agent (e.g., nicotine solution) delivered to or onto the heater element prior to the creation of the aerosol. In some cases, the dose (or loaded dose) is the amount of an agent coated on a heater element prior to the creation of the aerosol. The loaded dose can be about 2% of the target dose (the label claimed dose or goal dose). The emitted dose can be 92% to 97% of the loaded dose. For example, the amount of an agent (e.g., nicotine) actually delivered to the lung if the label claim dose is 100 µg can be between 90% and 99%.

In some cases, a substrate in an aerosol generating device as provided herein comprises a nicotine mixture or formulation. The substrate can be a liquid formulation. In some cases, a substrate in an aerosol generating device as provided herein comprises a liquid nicotine formulation. The nicotine mixture can comprise about, more than, less than, or at least 1, 2, 3, 4, 4.5, 5, 6, 7, 8, 9, 10, 11, 12, 13, 14, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 94, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% nicotine. In some cases, a mixture in an aerosol generating device as provided herein (e.g., electronic cigarette) comprises 0% nicotine.

The nicotine bolus theory can indicate that the dependence-producing potential of combustible, tobacco cigarettes can relate to a rapid increase in nicotine at receptor sites in the brain. During smoking, vaporized nicotine can be absorbed by the lungs and can be subsequently carried directly to the heart and then straight to the brain. Nicotine absorbed by the lungs can remain as a relatively high concentration or bolus in the blood until it reaches the brain. In some cases, an aerosol generating device (e.g., electronic cigarette) as provided herein is configured to generate an aerosol comprising nicotine such that the size of the aerosol particles comprising nicotine are optimal for delivery to and absorption by the lungs of a user of the device, leading to a rapid, cigarette-like nicotine absorption. The nicotine containing aerosol produced by aerosol generating devices as provided herein can generate a nicotine bolus in the blood of a user of the device similar to nicotine bolus achieved by smoking a cigarette. In some cases, aerosol particles comprising nicotine produced by a heater element or device as provided herein can achieve peak plasma concentrations similar to peak plasma concentrations achieved by smoking a cigarette. In some cases, aerosol particles comprising nicotine produced by a heater element or device as provided herein can achieve peak plasma concentrations in a time frame similar to the time frame required to achieve peak plasma concentrations achieved by smoking a cigarette. The aerosol (e.g., condensation aerosol) comprising nicotine produced by any of the devices provided herein can result in rapid, cigarette-like nicotine absorption resulting in nicotine plasma concentrations similar or substantially similar to the nicotine plasma concentration achieved from smoking a cigarette. In some cases, the plasma concentration can be an arterial plasma concentration. In some cases, the plasma concentration can be a venous plasma concentration. Smoking a single cigarette can produce peak increments of plasma nicotine concentration of 5-30 ng/ml.

In some cases, use of an aerosol generating device described herein can produce an arterial plasma nicotine concentration in the user of the device of about 1 ng/mL to about 200 ng/ml, about 1 ng/mL to about 150 ng/ml, about 1 ng/ml to about 100 ng/ml, about 1 ng/ml to about 75 ng/ml, about 1 ng/ml to about 50 ng/ml, about 1 ng/ml to about 40 ng/ml, about 1 ng/ml to about 30 ng/ml, about 1 ng/ml to about 20 ng/ml, about 1 ng/ml to about 10 ng/ml, about 10 ng/ml to about 200 ng/ml, about 10 ng/ml to about 150 ng/ml, about 10 ng/ml to about 100 ng/ml, about 10 ng/ml to about 75 ng/ml, about 10 ng/ml to about 50 ng/ml, about 10 ng/ml to about 40 ng/ml, about 10 ng/ml to about 30 ng/ml, about 10 ng/ml to about 20 ng/ml, about 10 ng/ml to about 15 ng/ml, about 20 ng/ml to about 200 ng/ml, about 20 ng/ml to about 150 ng/ml, about 20 ng/ml to about 100 ng/ml, about 20 ng/ml to about 75 ng/ml, about 20 ng/ml to about 50 ng/ml, about 20 ng/ml to about 40 ng/ml, about 20 ng/ml to about 30 ng/ml, about 20 ng/ml to about 24 ng/ml, about 30 ng/ml to about 200 ng/ml, about 30 ng/ml to about 150 ng/ml, about 30 ng/ml to about 100 ng/ml, about 30 ng/ml to about 75 ng/ml, about 30 ng/ml to about 50 ng/ml, about 30 ng/ml to about 40 ng/ml, or about 30 ng/ml to about 35 ng/ml. In some cases, use of an aerosol generating device described herein can produce an arterial plasma nicotine concentration in a user of the device of about, more than, less than, or at least 1, 2, 3, 4, 5, 6, 7, 8, 9, 10, 11, 12, 13, 14, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 ng/ml. The arterial plasma nicotine concentration can be produced after receiving at least 1, 2, 3, 4, 5, 6, 7, 8, 9, or 10 doses from the aerosol generating device. A dose can be a puff or inhalation from the aerosol generating device.

In some cases, use (e.g., puff or inhalation) from an aerosol generating device described herein can produce a peak plasma nicotine concentration in a user of the device within about 30 seconds to 30 minutes, 30 seconds to 20 minutes, 30 seconds to 10 minutes, 30 seconds to 5 minutes, 30 seconds to 2 minutes, 1 to about 30 minutes, about 1 minute to about 25 minutes, about 1 minute to about 20 minutes, about 1 minute to about 15 minutes, about 1 minute to about 10 minutes, about 5 minutes to about 30 minutes, about 5 minutes to about 25 minutes, about 5 minutes to about 20 minutes, about 5 minutes to about 15 minutes, about 5 minutes to about 10 minutes, about 10 minutes to about 30 minutes, about 10 minutes to about 25 minutes, about 10 minutes to about 20 minutes, or about 10 minutes to about 15 minutes of use of the device. A use of the device can be a single inhalation on the device. A use of the device can be a plurality of inhalations on the device. A plurality can be exactly, about, at least, at most, less than, or more than 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 uses (e.g., puffs or inhalations) from the device. A plurality can be about 2 to about 4, about 2 to about 10, about 2 to about 20, about 5 to about 10, about 10 to about 20, about 20 to about 30, about 30 to about 50, about 50 to about 60, about 60 to about 75 or about 75 to about 100 uses (e.g., puffs or inhalations) from the device.

The peak increments of plasma nicotine concentration from smoking a cigarette can be achieved within 10 minutes. In some cases, peak increments of plasma nicotine concentration from using a device as provided herein can be achieved within 10 minutes of a use of a device as provided herein. The nicotine arterial plasma concentration generated in a user of an aerosol generating device as provided herein can be about, more than, less than, or at least 1%, 2%, 3%, 4%, 5%, 6%, 7%, 8%, 9%, 10%, 11%, 12%, 13%, 14%, 15%, 16%, 17%, 18%, 19%, 20%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the nicotine plasma concentration achieved by the user smoking a cigarette. The nicotine arterial plasma concentration generated in a user of an aerosol generating device as provided herein can be between 1%-10%, 10%-20%, 20%-30%, 30%-40%, 40%-50%, 50%-60%, 60%-70%, 70%-80%, 80%-90%, or 90%-100% of the nicotine plasma concentration achieved by smoking a cigarette. The nicotine arterial plasma concentration generated in a user of an aerosol generating device as provided herein can be about 1% to about 10%, about 10% to about 20%, about 20% to about 30%, about 30% to about 40%, about 40% to about 50%, about 50% to about 60%, about 60% to about 70%, about 70% to about 80%, about 80% to about 90%, or about 90% to about 100% of the nicotine plasma concentration achieved by smoking a cigarette.

In some cases, an agent can be an aerosolized medication, e.g., a sympathomimetic (e.g., nonselective sympathomimetic (e.g., epinephrine, racemic epinephrine (vaponephrine)); a beta sympathomimetics (e.g., isoetharine (Bronkosol); or a non-catecholamine beta sympathomimetic (e.g., metaproterenol (Alupent), albuterol (Porventil, Ventolin), Terbutaline (Brethine, Bricanyl), salmeterol (serevent), levalbuterol (Xeopenex). An aerosolized medication can be a nonsteroidal anti-inflammatory agent (e.g., cromolyn sodium (Intal) or nedocromil sodium (Tilade). In some cases, an aerosolized medication can be a corticosteroid (e.g., Dexamethasone (Dedcadron), Beclamethasone (Venceril, Beclovent), Triamcinolone (Azmacort), Flunisolide (Aerobid), Fluticasone proprionate (Flovent), or Budesonide suspension (Pulmocort)). In some cases, an aerosolized medication is an anticholinergic (e.g., atropine, or ipratropium bromide (Atrovent). In some cases, an aerosolized medication is a mucolytic/surface active agent (e.g., acetylcysteine (mucomyst), sodium bicarbonate ($NaHCO_3$), or ethyl alcohol 30-50% (ethanol). An aerosolized medication can be an anti-protozoal agent (e.g., pentamidine isethionate (Nebupent)). An aerosolized mediation can be a combination drug (e.g., Combivent (ipratropium bromide and albuterol sulfate) or Advair Diskus (salmeterol and flovent). An aerosolized medication can be a recombinant human deoxyribonuclease I solution (e.g., Dornase alfa (pulmozyme)). An aerosolized medication can be an anti-viral agent (virazole (ribavirin)). An aerosolized medication can be an antibiotic (e.g., tobramycin (tobi)). In some cases, an aerosolized medication is delivered by an aerosol generating device as provided herein. In some cases, an aerosolized medication is delivered by a non-electronic delivery device.

In some cases, an agent can be a luteinizing hormone-releasing hormone (LHRH) or insulin.

Carriers

In some cases, an aerosol generating device as provided herein comprises a substrate, wherein the substrate comprises an agent (e.g., nicotine). The substrate can be a liquid at room temperature. The substrate can be liquid during use of the aerosol generating device such that the liquid substrate is delivered to or onto a heater element during use of the device. In some cases, the agent (e.g., nicotine) is mixed with one or more other substances. The one or more other substances can be pharmaceutically acceptable excipients or carriers. The suitable pharmaceutically acceptable excipients or carriers can be volatile or nonvolatile. The volatile excipients, when heated, can be volatilized, aerosolized and inhaled with the agent (e.g. nicotine). Classes of such excipients are known in the art and include, without limitation, gaseous, supercritical fluid, liquid and solid solvents. The excipient/carriers can be water; a terpene, such as menthol; an alcohol, such as ethanol, propylene glycol, vegetable glycerin, glycerol and other similar alcohols; dimethylformamide; dimethylacetamide; wax; supercritical carbon dioxide; dry ice; and mixtures or combinations thereof.

The one or more other substances can be, e.g., propylene glycol (1,2-dihydroxypropane, 1,2-propanediol, methyl glycol, or trimethyl glycol). The ratio of agent (e.g., nicotine) to propylene glycol can be about, more than, less than, or at least 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 2:1, 1:1, 1:2, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, or 1:100. The ratio of agent (e.g., nicotine) to propylene glycol can be from about 100:1 to about 1:100, about 75:1 to about 1:100, about 50:1 to about 1:100, about 25:1 to about 1:100, about 25:1 to about 1:50, about 10:1 to about 1:100, about 10:1 to about 1:50, about 10:1 to about 1:20, about 5:1 to about 1:20, or about 1:1 to about 1:20. In one example, a 100 µg dose of agent (e.g., nicotine) and 1:10 ratio yields a volume of 1 $mm^3$ (1 mg). A mixture of agent (e.g., nicotine) and another substance, e.g., propylene glycol, can be held in an agent (e.g., nicotine) reservoir (e.g., as a liquid).

In one embodiment, the one or more other substances is vegetable glycerin. The ratio of an agent (e.g., nicotine) to vegetable glycerin can be about, more than, less than, or at least 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 2:1, 1:1, 1:2, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, or 1:100. The ratio of an agent (e.g., nicotine) to vegetable glycerin can be from about 100:1 to about 1:100, about 75:1 to about 1:100, about 50:1 to about 1:100, about 25:1 to about 1:100, about 25:1 to about 1:50, about 10:1 to about 1:100, about 10:1 to about 1:50, about 10:1 to about 1:20, about 5:1 to about 1:20, or about 1:1 to about 1:20. In one example, a 100 µg dose of agent (e.g., nicotine) and 1:10 ratio yields a volume of 1 $mm^3$ (1 mg). A mixture of agent (e.g., nicotine) and vegetable glycerin can be held in an agent (e.g., nicotine) reservoir (e.g., as a liquid).

In another embodiment, the one or more other substances comprise vegetable glycerin and propylene glycol. The ratio of vegetable glycerin to propylene glycol can be about, more than, less than, or at least 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 2:1, 1:1, 1:2, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, or 1:100. The ratio of agent (e.g., nicotine) to vegetable glycerin can be from about 100:1 to about 1:100, about 75:1 to about 1:100, about 50:1 to about 1:100, about 25:1 to about 1:100, about 25:1 to about 1:50, about 10:1 to about 1:100, about 10:1 to about 1:50, about 10:1 to about 1:20, about 5:1 to about 1:20, or about 1:1 to about 1:20.

The ratio of agent (e.g., nicotine) to mixture of vegetable glycerin and propylene glycol can be about, more than, less than, or at least 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 2:1, 1:1, 1:2, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, or 1:100. The ratio of agent (e.g., nicotine) to vegetable glycerin and glycerin can be from about 100:1 to about 1:100, about 75:1 to about 1:100, about 50:1 to about 1:100, about 25:1 to about 1:100, about 25:1 to about 1:50, about 10:1 to about 1:100, about 10:1 to about 1:50, about 10:1 to about 1:20, about 5:1 to about 1:20, or about 1:1 to about 1:20.

In another embodiment, the one or more other substances can be polyethylene glycol (PEG). The PEG can be PEG200, PEG300, PEG400, PEG600, PEG1000, PEG2000, PEG4000, or PEG6000.

In one embodiment, the one or more other substances is glycerol.

In another embodiment, an aerosol generating device comprises a liquid formulation comprising a mixture of an agent (e.g., nicotine) and polyethylene glycol. A mixture can comprise an agent (e.g., nicotine), polyethylene glycol, and vegetable glycerin. A mixture can comprise an agent (e.g., nicotine), polyethylene glycol, vegetable glycerin, and propylene glycol. In another embodiment, a mixture comprises an agent (e.g., nicotine), polyethylene glycol, and propylene glycol. A mixture can comprise an agent (e.g., nicotine), propylene glycol, and vegetable glycerin. A recipe for a nicotine solution can comprise: 6% nicotine, 85% propylene glycol, 2% glycerol, 2% essence, 1% organic acid and 1% anti-oxidation agent. A recipe for a nicotine solution can comprise: 4% nicotine, 80% propylene glycol, 5% glycerol, 1% butyl valerate, 1% isopentyl hexonate, 0.6% lauryl laurate, 0.4% benzyl benzoate, 0.5% methyl octynicate, 0.2% ethyl heptylate, 0.3% hexyl hexanoate, 2% geranyl butyrate, 0.5% menthol, 0.5% citric acid and 4% tobacco essence. A recipe for a nicotine solution can comprise: 2% nicotine, 90% propylene glycol, 2.5% citric acid, 1% essence and 4.5% tobacco essence. A recipe for a nicotine solution can comprise: 0.1% nicotine, 80% propylene glycol, 5% glycerol, 8% alcohol, 2.9% water, 1% essence, 1% tobacco essence and 2% organic acid. A nicotine solution can comprise 0.4-3.5% nicotine, 0.05-2% cigarette essence, 0.1-3.1% organic acid, 0.1-0.5% anti-oxidation agent, and the rest is 1,2-propylene glycol. A nicotine solution or formulation can comprise by % weight: 25-90% polyethylene glycol, 9-50% propylene glycol and 0.3-52% a taste modifier. The taste modifier's % weight can be constituted by one or more than two raw materials consisting of 2-acetylpyrazine, vanillin, 2,3,5-trimethylprazine, methyl cyclopentenolone, linalool, extracts of Vanilla planifolia, caprylolactone, Bulgarian Rose Otto, megastigmatrienone (Baosha aromatic tobacco essential oil), damascenone, purified water, menthol, fire-cured tobacco essential oil, fire-cured tobacco absolute oil, burley tobacco absolute oil, Turkey aromatic tobacco absolute oil and glycerin, 0.5-10% purified water, and 0.5-18% nicotine. A nicotine formulation as described above can further comprise by % weight extra health materials consisting of 2-10% green tea extract, 2-10% caffeine, 3-20% extracts of wolfberry or 1-5% Viagra virility medication.

In one embodiment, the percentage of an agent (e.g., nicotine) in a formulation (e.g., solution) comprising an agent (e.g., nicotine) can be about, more than, less than, or at least 0.25, 0.5, 0.75, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75, 10, 10.25, 10.5, 10.75, 11, 11.25, 11.5, 11.75, 12, 12.25, 12.5, 12.75, 13, 13.25, 13.5, 13.75, 14, 14.25, 14.5, 14.75, 15, 15.25, 15.5, 15.75, 16, 16.25, 16.5, 16.75, 17, 17.25, 17.5, 17.75, 18, 18.25, 18.5, 18.75, 19, 19.25, 19.5, 19.75, 20, 20.5, 21, 21.5, 22, 22.5, 23, 23.5, 24, 24.5, or 25% by volume. The percentage of an agent (e.g., nicotine) in a formulation (e.g., solution) comprising an agent (e.g., nicotine) can be from about 0.25 to about 1.25, about 1.25 to about 2.5, about 2.5 to about 5, about 5 to about 7.5, about 7.5 to about 10, about 10 to about 12.5, about 12.5 to about 15, about 15 to about 17.5, about 17.5 to about 20, or about 20 to about 25% by volume. The formulation (e.g., solution) can further comprise one or more substances. The one or more substances can be propylene glycol and/or vegetable glycerin. The formulation can be liquid at room temperature or at temperatures at which the device is generally used by a user or subject.

The source of nicotine for use in the devices and methods as provided herein can be a tobacco or tobacco material. Here, a tobacco or tobacco material can be defined as any combination of natural and synthetic material that can be vaporized for pleasure or medicinal use. The formulation comprising nicotine can comprise flue-cured tobacco, glycerin, and flavorings. The formulation comprising nicotine can comprise flue-cured tobacco, propylene glycol, and flavorings. A liquid formulation comprising nicotine can be produced by chopping tobacco into fine pieces (less than 3 mm diameter, less than 2 mm), adding the other ingredients (e.g., propylene glycol, vegetable glycerin, water, and/or flavorings), and mixing until even consistency is achieved.

Additives

A substrate in an aerosol generating device as provided herein can comprise a mixture comprising an agent and one or more flavors. The one or more flavorings can be a flavor offered by, e.g., Flavourart (Italy), Flavor Apprentice, or LorAnn. A flavor can be, e.g., almond, almond amaretto, apple, Bavarian cream, black cherry, black sesame seed, blueberry, brown sugar, bubblegum, butterscotch, cappuccino, caramel, caramel cappuccino, cheesecake (graham crust), cinnamon redhots, cotton candy, circus cotton candy, clove, coconut, coffee, clear coffee, double chocolate, energy cow, graham cracker, grape juice, green apple, Hawaiian punch, honey, Jamaican rum, Kentucky bourbon, kiwi, koolada, lemon, lemon lime, tobacco, maple syrup, maraschino cherry, marshmallow, menthol, milk chocolate, mocha, Mountain Dew, peanut butter, pecan, peppermint, raspberry, banana, ripe banana, root beer, RY4, spearmint, strawberry, sweet cream, sweet tarts, sweetener, toasted almond, tobacco, tobacco blend, vanilla bean ice cream, vanilla cupcake, vanilla swirl, vanillin, waffle, Belgian waffle, watermelon, whipped cream, white chocolate, wintergreen, amaretto, banana cream, black walnut, blackberry, butter, butter rum, cherry, chocolate hazelnut, cinnamon roll, cola, crème de menthe, eggnog, English toffee, guava, lemonade, licorice, maple, mint chocolate chip, orange cream, peach, pina colada, pineapple, plum, pomegranate, pralines and cream, red licorice, salt water taffy, strawberry banana, strawberry kiwi, tropical punch, tutti frutti, or vanilla. The number of flavors in a mixture can be about, more than, less than, or at least 1, 2, 3, 4, 5, 6, 7, 8, 9, or 10.

A flavoring can be used to pair nicotine administration with certain gustatory and/or olfactory sensations. Subsequent administration of agent (e.g., nicotine) doses can be reduced while retaining the flavoring to help the user reduce their agent (e.g., nicotine) dependency and enable cravings to be fully or partially sated using the flavoring as a conditioned stimulus.

Power Supply/Batteries

An aerosol generating device (e.g., electronic cigarette) as provided herein can comprise at least one primary air inlet and one air outlet, a power device, a sensor, an atomizing core component (i.e., heater element) and/or a storage component (e.g., reservoir). Adapters as described herein can be coupled to aerosol generating devices provided herein (e.g., electronic cigarettes) with different configurations. For example, the configurations can be one piece, two piece, or three piece aerosol generating devices (e.g., electronic cigarettes). A one-piece aerosol generating device (e.g., electronic cigarette) can comprise disposable units supplied with a pre-charged battery and a liquid solution (e.g., nicotine solution) cartridge or reservoir. A two-piece aerosol generating device (e.g., electronic cigarette) can comprise a refill cartridge or reservoir and a non-disposable unit. The non-disposable unit can comprise a rechargeable battery, while the refill cartridge or reservoir can comprise a combination of heater element and cartridge or reservoir in the same unit. A three-piece aerosol generating device (e.g., electronic cigarette) can comprise a rechargeable battery, a heater element, and a replacement cartridge or reservoir, wherein each of the rechargeable battery, heater element and reservoir are separate units, whereby the battery and heater element are non-disposable. In some cases, a device as provided herein comprises an amount of substrate (e.g., nicotine solution) sufficient to provide about 1 day of use on demand by a user. In some cases, a device as provided herein comprises an amount of substrate (e.g., nicotine solution) sufficient to provide about 7 days of use on demand by a user. In some cases, a device as provided herein comprises an amount of substrate (e.g., nicotine solution) sufficient to provide about 14 days of use on demand by a user. In some cases, a device as provided herein comprises an amount of substrate (e.g., nicotine solution) sufficient to provide about 1 to about 7 days of use on demand by a user. In some cases, a device as provided herein comprises an amount of substrate (e.g., nicotine solution) sufficient to provide about 1 to about 14 days of use on demand by a user. In some cases, a device as provided herein comprises an amount of substrate (e.g., nicotine solution) sufficient to provide about 7 to about 14 days of use on demand by a user. The device can be a one-piece device such that the device is disposable. The device can be a multi-piece (e.g., two or three-piece as provided herein) device such that the amount of substrate (e.g., nicotine solution) provided therein is for the number of days provided herein (e.g., 1, 7, or 14 days). The substrate (e.g., nicotine solution) can be stored in a reservoir. The reservoir can be refillable such that the volume of the reservoir provides an amount of substrate (e.g., nicotine solution) for the number of days provided herein (e.g., 1, 7, or 14 days).

An aerosol generating device (e.g., electronic cigarette) as provided herein can comprise a battery. In some cases, an aerosol generating device (e.g., electronic cigarette) as provided herein can comprise one or more batteries, e.g., a rechargeable lithium (e.g., lithium-ion) battery. A rechargeable battery can be charged via USB or AC outlet. In some cases, the aerosol generating device (e.g., electronic cigarette) comprises an elongate housing and a battery as described herein. The elongate housing can be tubular in shape. The tubular elongate housing can have a first longitudinal end and a second longitudinal end in contact with a mouthpiece. The mouthpiece can be the outlet at the second longitudinal end of the elongate housing. The mouthpiece can be the outlet of an airflow channel in the elongate housing, wherein the air flow channel comprises an inlet and an outlet. The mouthpiece can be an adapter or an outlet of an adapter as provided herein. The tubular elongate housing can be substantially cylindrical with lateral dimensions substantially identical to that of the mouthpiece to provide geometrical continuity between the elongate housing and the mouthpiece. The first longitudinal end of the tubular elongate housing can be distal from the mouthpiece and form a free end of the aerosol generating device (e.g., electronic cigarette). In some cases, an elongate and cylindrical battery is inserted inside the tubular elongate housing to provide electrical power to operate an aerosol generating device (e.g., electronic cigarette) while leaving a longitudinally extending air passage way for air to pass from a first longitudinal end to a second longitudinal end of the aerosol generating device (e.g., electronic cigarette). To facilitate smooth movement of air across the battery, the cross-sectional dimension of the battery can be smaller than the internal clearance of the air flow channel in the elongate housing and longitudinally extending air guides are formed on the inside of the air-flow channel to support the battery and to guide air to move more smoothly through the space between the outside of the battery and the interior of the air-flow channel. The air-flow channel can be tubular. A stop member can be mounted at the first longitudinal end to maintain the battery and other components inside the elongate housing. In some cases, rechargeable battery can be a nickel cadmium battery or nickel metal hydride. The one or more batteries can be one or more disposable dry cell batteries, e.g., 4.5 volt, D, C, AA, AAA, AAAA, 9-volt, CR2032, or LR44 battery. The one or more batteries can be 1/2AA, A, B, F, N, No. 6, Sub-C, A23, A27, duplex, 45R44, 523, 531, CR123A, CR2, 2CR5, CR-P2, CR-V3, CR927, CR1025, CR1216, CR1220, CR1225, CR1616, CR1620, CR1632, CR2012, CR2016, CR2025, CR2032, CR2320, CR2325, CR2330, CR2354, CR2430, CR2450, CR2477, CR3032, or CR11108. In some cases, the battery can be an alkaline battery or carbon-zinc battery. A power device can be nickel metal hydride, lithium ion, lithium polymer, lead acid, alkaline, nickel cadmium, and lithium coin cells batteries.

Style

Aerosol generating devices as provided herein can be styled as electronic cigarettes (e-cigarette), mini electronic cigarettes, pen-style electronic cigarettes, electronic cigars, electric hookahs, and electronic pipes. A mini e-cigarette can resemble regular non electronic cigarettes. Pen-styled electronic cigarettes can have the appearance of an ink pen. A pen-styled electronic cigarette can be longer than a non-electric cigarette but can be comparatively smaller and thinner Electronic cigars can be made to resemble regular cigars, and an electronic pipe can resemble regular pipes.

Dimensions

An aerosol generating device (e.g., electronic cigarette) can comprise a housing. The housing can have an outer or external wall. The housing can further comprise an internal housing. The housing can be cylindrical. The internal housing can be cylindrical. In some cases, an internal housing of an aerosol generating device as provided herein comprises an airflow channel or passageway comprising an inlet and an outlet. The internal housing or passageway can comprise an aerosol generation region. In some cases, the housing of an aerosol generating device as provided herein comprises an elongated housing. The elongated housing can be cylindrical. In some cases, the housing further comprises an internal housing. The internal housing can be cylindrical. The internal housing or passageway of an aerosol generating device as provided herein can have a diameter of about, more than, less than, or at least 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 mm. The diameter of an internal housing can be about 0.5 cm to about 1 cm, about 0.25 cm to about 0.75 cm, about 0.25 cm to about 1 cm, about 0.25 cm to about 1.5 cm, about 0.25 cm to about 2 cm, about 0.25 cm to about 2.5 cm, or about 0.25 cm to about 3 cm.

The housing can have an outer or external wall. In some cases, an aerosol generating device as provided herein comprises an elongated housing. The elongated housing can be cylindrical. In some cases, a housing of an aerosol generating device as provided herein has an inlet and an outlet such that a carrier gas (e.g., air) flow channel or passageway is created between the inlet and the outlet such that the housing defines the walls of the flow channel or passageway. The housing of an aerosol generating device as provided herein can have an outer or external diameter of about, more than, less than, or at least 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 mm. The housing can have an outer or external diameter of about 0.5 cm to about 1 cm, about 0.25 cm to about 0.75 cm, about 0.25 cm to about 1 cm, about 0.25 cm to about 1.5 cm, about 0.25 cm to about 2 cm, about 0.25 cm to about 2.5 cm, or about 0.25 cm to about 3 cm.

The housing of an aerosol generating device as provided herein can have an outer or external length of about, more than, less than, or at least 20, 21, 22, 23, 24, 25, 26 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 mm.

The housing of an aerosol generating device as provided herein can have a transverse dimension of about, more than, less than, or at least 1, 2, 3, 4, 5, 6, 7, 8, 9, 10, 11, 12, 13, 14, 15, 16, 17, 18, 19, 20, 21, 22, 23, 24, 25, 26 27, 28, 29, 30, 31, 32, 33, 34, 35, 36, 37, 38, 39, or 40 mm.

The housing of an aerosol generating device as provided herein can have a cross-sectional area. The housing of an aerosol generating device as provided herein can comprise an air flow channel comprising an inlet and an outlet. The air flow channel can have an aerosol generation region. The aerosol generation region can have a cross-sectional area. In some cases, the aerosol generation region of the air flow channel of an aerosol generating device as provided herein has a cross-sectional area that generates an aerosol comprising a desired diameter for a given volumetric air flow rate. The aerosol can be a condensation aerosol. The desired diameter can be from about 1 μm to about 5 μm. The desired diameter can be from about 1 μm to about 3 μm. The diameter can be a mass median aerodynamic diameter (MMAD). The diameter can be a volume median diameter (VMD). The cross-sectional area of an aerosol generation region as provided herein can be about, more than, less than, or at least 1, 2, 3, 4, 5, 6, 7, 8, 9, 10, 11, 12, 13, 14, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 $mm^2$. The cross-sectional area of an aerosol generation region of an aerosol generating device as provided herein can be about 1 to about 5 $mm^2$, about 5 to about 10 $mm^2$, about 10 to about 15 $mm^2$, about 15 to about 20 $mm^2$, about 20 to about 25 $mm^2$, about 25 to about 30 $mm^2$, about 30 to about 35 $mm^2$, about 35 to about 40 $mm^2$, about 40 to about 45 $mm^2$, about 45 to about 50 $mm^2$, about 50 to about 55 $mm^2$, about 55 to about 60 $mm^2$, about 60 to about 65 $mm^2$, about 65 to about 70 $mm^2$, about 70 to about 75 $mm^2$, about 75 to about 80 $mm^2$, about 80 to about 85 $mm^2$, about 85 to about 90 $mm^2$, about 90 to about 95 $mm^2$, about 95 to about 100 $mm^2$, about 100 to about 105 $mm^2$, about 105 to about 110 $mm^2$, about 110 to about 115 $mm^2$, about 115 to about 120 $mm^2$, about 120 to about 125 $mm^2$, about 125 to about 130 $mm^2$, about 130 to about 135 $mm^2$, about 135 to about 140 $mm^2$, about 140 to about 145 $mm^2$, about 145 to about 150 $mm^2$, about 150 to about 155 $mm^2$, about 155 to about 160 $mm^2$, about 160 to about 165 $mm^2$, about 165 to about 170 $mm^2$, about 170 to about 175 $mm^2$, about 175 to about 180 $mm^2$, about 180 to about 185 $mm^2$, about 185 to about 190 $mm^2$, about 190 to about 195 $mm^2$, or about 195 to about 200 $mm^2$. In some cases, a cross-sectional area of an aerosol generation region has the same cross-sectional area as regions of the air flow channel upstream and/or downstream of the aerosol generation region. The cross-sectional area of regions of the air flow channel upstream and/or downstream of the aerosol generation region can be different.

The volume of an aerosol generation region of an aerosol generating device as provided herein can be about, more than, less than, or at least 1, 10, 100, 200, 300, 400, 500, 600, 700, 800, 900, 1000, 1250, 1500, 1750, 2000, 2250, 2500, 2750, 3000, 3250, 3500, 3750, or 4000 mm$^3$. The volume of an aerosol generation region of an aerosol generating device as provided herein can be about 1 to about 10 mm$^3$, about 10 to about 100 mm$^3$, about 100 to about 200 mm$^3$, about 200 to about 400 mm$^3$, about 400 to about 600 mm$^3$, about 600 to about 800 mm$^3$, about 800 to about 1000 mm$^3$, about 1000 to about 1500 mm$^3$, about 1500 to about 2000 mm$^3$, about 2000 to about 2500 mm$^3$, about 2500 to about 3000 mm$^3$, about 3000 to about 3500 mm$^3$, or about 3500 to about 4000 mm$^3$. In some cases, a volume of an aerosol generation region has the volume as regions of the air flow channel upstream and/or downstream of the aerosol generation region. The volume of regions of the air flow channel upstream and/or downstream of the aerosol generation region can be different.

Heater Element

A heater element in an aerosol generating device (e.g., electronic cigarette) as provided herein can be used to vaporize or aerosolize a substrate. A heater element can be any heater element as provided herein. The substrate can comprise an agent. In some cases, a substrate in an aerosol generating device as provided herein is a liquid substrate. The liquid substrate can comprise an agent. The agent can be any pharmaceutically active agent as provided herein. In some cases, a pharmaceutically active agent comprises nicotine. The heater element can be used to generate a condensation aerosol from a liquid substrate comprising a pharmaceutically active agent as provided herein. The condensation aerosol can comprise particles of a size suitable for delivery to the lungs of a subject as provided herein. In some cases, the heater element comprises an electrically resistive material. Electrically conductive/resistive materials that can be useful as resistive heater elements can be those having low mass, low density, and moderate resistivity and that are thermally stable at the temperatures experienced during use of the aerosol generating device. In some cases, a heater element heats and cools rapidly, and can efficiently use energy. Rapid heating of the heater element can provide almost immediate volatilization of an aerosol forming substrate (e.g., liquid formulation comprising nicotine) in proximity thereto. Rapid cooling to a temperature below the volatilization temperature of the substrate can prevent substantial volatilization (and hence waste) of the substrate during periods when aerosol formation is not desired. Such heater elements also permit relatively precise control of the temperature range experienced by the substrate, e.g., when time based current control is employed. In some cases, electrically conductive/resistive materials are chemically non-reactive with the materials being heated (e.g., aerosol precursor materials and other inhalable substance materials) so as not to adversely affect the flavor or content of the aerosol or vapor that is produced. Exemplary, non-limiting, materials that can be used as the electrically conductive/resistive material include carbon, nickel, iron, chromium, graphite, tantalum, stainless steel, gold, platinum, tungsten molybdenum alloy, metal ceramic matrices, carbon/graphite composites, metals, metallic and non-metallic carbides, nitrides, silicides, inter-metallic compounds, cermets, metal alloys (e.g., aluminum alloys, iron alloys, etc.), and metal foils. In some cases, a refractory material is used. Various, different materials can be mixed to achieve the desired properties of resistivity, mass, and thermal conductivity. In some cases, metals that can be utilized include, for example, nickel, chromium, alloys of nickel and chromium (e.g., nichrome), and steel. Suitable metal-ceramic matrices can include silicon carbide aluminum and silicon carbide titanium. Oxidation resistant intermetallic compounds, such as aluminides of nickel and aluminides of iron are also suitable. Of the listed materials, stainless steel and the aluminum, iron or chromium alloys can be encapsulated in a suitable ceramic material because of their reactivity. Suitable ceramic materials for encapsulation include silica, alumina, and sol gels. The heater element can be made of a thin stainless steel foil or wires of the materials described herein. Materials that can be useful for providing resistive heating are described in U.S. Pat. No. 5,060,671; U.S. Pat. No. 5,093,894; U.S. Pat. No. 5,224,498; U.S. Pat. No. 5,228,460; U.S. Pat. No. 5,322,075; U.S. Pat. No. 5,353,813; U.S. Pat. No. 5,468,936; U.S. Pat. No. 5,498,850; U.S. Pat. No. 5,659,656; U.S. Pat. No. 5,498,855; U.S. Pat. No. 5,530,225; U.S. Pat. No. 5,665,262; U.S. Pat. No. 5,573,692; and U.S. Pat. No. 5,591,368, the disclosures of which are incorporated herein by reference in their entireties.

A heater element (e.g., resistive heater element) in an aerosol generating device as provided herein can be provided in a form that enables the heater element to be positioned in intimate contact with or in close proximity to the substrate (i.e. to provide heat to the substrate through, for example, conduction, radiation, or convection). In some cases, the substrate is a liquid substrate comprising a pharmaceutically active agent (e.g., nicotine). In some cases, the heater element can be provided in a form such that the substrate (e.g., liquid substrate) can be delivered to the heater element for vaporization. The delivery of the liquid substrate can take on a variety of embodiments, such as wicking of the liquid substrate to the heater element using a wick (e.g., fibrous wick) in fluid communication with the liquid substrate or flowing the liquid substrate to the heater element, such as through a capillary, which can include valve flow regulation. As such, the liquid substrate can be in one or more reservoirs positioned sufficiently away from the heater element to prevent premature vaporization, but positioned sufficiently close to the heater element to facilitate transport of the liquid substrate, in the desired amount, to the heater element for vaporization. In some cases, the one or more reservoirs comprising a liquid substrate can be located in an annular space surrounding a tubular or cylindrical air flow channel or passageway. In some cases, the heater element is in fluid communication with the liquid substrate stored in one or more reservoirs located in an annular space surrounding an air flow channel or passageway, wherein the heater element is located within the air flow channel or passageway. In some cases, the liquid substrate comprising a pharmaceutically active agent (e.g., nicotine) is delivered to the heater element through the use of a positive displacement pump. The positive displacement pump can be a reciprocating, metering, rotary-type, hydraulic, peristaltic, gear, screw, flexible impeller, diaphragm, piston, or progressive cavity pump, or any other pump utilizing positive displacement as known in the art. The positive displacement pump can be in fluid communication with the heater element. The positive displacement pump can be in fluid communication or fluidically coupled to a reservoir comprising a pharmaceutically active agent (e.g., nicotine). The positive displacement pump can be in fluid communication with the heater element and a reservoir comprising a pharmaceutically active agent (e.g., nicotine). The positive displacement pump can be within an air-flow channel or passageway in an aerosol generating device as provided herein or external to the air flow channel or passageway.

The heater element (e.g., electrically resistive material) can be provided in a variety forms, such as in the form of straight line, a foil, a foam, discs, spirals (e.g., single spiral, double spiral, cluster or spiral cluster), fibers, wires, films, yarns, strips, ribbons, or cylinders, as well as irregular shapes of varying dimensions. In some cases, a heater element can be a resistive heater element comprising a conductive substrate, such as described in US20130255702A1 to Griffith et al., the disclosure of which is incorporated herein by reference in its entirety. In some cases, a heater element can be a resistive heater element that can be present as part of a micro-heater component, such as described in US20140060554A1, the disclosure of which is incorporated herein by reference in its entirety. In some cases, a heater element is a droplet ejection type heater element such as described in U.S. Pat. No. 5,894,841, the disclosure of which is incorporated herein by reference in its entirety. In some cases, a heater element comprises an ejector in combination with a heater element electrically resistive coil or thin film or foil), such as described in US20050016550A1, the disclosure of which is incorporated herein by reference in its entirety. In some cases, a heater element comprises a wire coil comprising electrically resistive material wrapped around a wick, wherein the wick has one end within a reservoir comprising the liquid substrate, such as described in US20110094523A1, the disclosure of which is incorporated by reference in its entirety. In some cases, a heater element in an aerosol generating device as provided herein comprises a "cartomizer," wherein the heater element and the reservoir comprising the liquid substrate are configured as a single disposable cartridge or unit. The cartomizer can be a first part of a two part aerosol generating device, wherein the second part can comprise the battery, LED, and a control apparatus (e.g., air-flow switch and any associated processor). In some cases, a heater element in an aerosol generating device as provided herein comprises an improved cartomizer that comprises: (a) a tube shape having an inlet and outlet; (b) a foam substrate for receiving a liquid formulation, the foam substrate defining an aerosol generation region; (c) a fiberglass member disposed within the aerosol generation region and in contact with the foam substrate to draw the liquid formulation into the region; and (d) a heater element disposed within the aerosol generation region and about the fiberglass member to vaporize the liquid formulation in the aerosol generation region, such as described in US20120199146A1, the disclosure of which is incorporated by reference in its entirety. In some cases, a heater element in an aerosol generating device as provided herein comprises an electrically resistive heater element (e.g., wire coil) with a liquid formulation permeating component (e.g., wicking element) directly sleeved thereon with the liquid permeating component in direct contact with a liquid containing reservoir that surrounds the heater element such as described in US20120111347A1 and US20120279512A1, the disclosure of each of which is incorporated by reference in its entirety. In some cases, a heater element in an aerosol generating device as provided herein comprises a porous wicking component surrounding a heating rod with an electrically resistive wire coil wrapped thereon, such as described in US20110209717A1, US20130125906A1, U.S. Pat. No. 7,832,410, U.S. Pat. No. 8,156,944, U.S. Pat. No. 8,393,331, or a wire coil wrapped around a fibrous wicking component such as described in U.S. Pat. No. 8,375,957, the disclosure of each of which is incorporated by reference in its entirety. In some cases, a heater element in an aerosol generating device as provided herein comprises an electrically resistive heater element within an atomization and spray device, such as described in US20110005535A1, the disclosure of which is incorporated by reference in its entirety. In some cases, a heater element comprises an atomizer, wherein the atomizer comprises an atomizer cover, a rubber sleeve, an atomizer sleeve, fibrous storage component infused with a liquid formulation (e.g., nicotine solution). two wires, a heating wire, a rubber pad, a threaded sleeve, a propping pin, a first fiber pipe, wicking element and a second fiber pipe, such as described in US20120145169A1, the disclosure of which is incorporated by reference in its entirety. In some cases, an aerosol generating device as provided herein comprises a vaporization nozzle. The vaporization nozzle can be located within an air flow channel in the aerosol generating device. The vaporization nozzle can be composed of any of the high-temperature resistant with low thermal conductivity materials provided herein. For example, the vaporization nozzle can be made of conventional ceramics or be made of aluminum silicate ceramics, titanium oxide, zirconium oxide, yttrium oxide ceramics, molten silicon, silicon dioxide, molten aluminum oxide. The vaporization nozzle can be made in the shape of a straight line or spiral, and can also be made from polytetrafluoethylene, carbon fiber, glass fiber, or other materials with similar properties. The vaporization nozzle can be a tubule comprising a heater element within the nozzle or on the outside of the nozzle, or can comprise no heater element and the tubule can be directly applied with heating current, such as described in U.S. Pat. No. 8,511,318, US20060196518A1, and US20120090630A1, the disclosure of each of which is incorporated herein by reference in its entirety. The heater element arranged within the vaporization nozzle can be made of wires of nickel chromium alloy, iron chromium aluminum alloy, stainless steel, gold, platinum, tungsten molybdenum alloy, etc., and can be in the shape of straight line, single spiral, double spiral, cluster or spiral cluster. The heating function of the heater element in the vaporization nozzle can be achieved by applying a heating coating on the inner wall of the tube, and the coating can be made from electro-thermal ceramic materials, semiconductor materials, or corrosion-resistant metal films, such as gold, nickel, chromium, platinum and molybdenum. In some cases, the heater element comprises a heat-conductive substrate having an outer surface, a film of a pharmaceutically active agent (e.g., nicotine) formed on the substrate surface, and a heat source for heating the substrate to a temperature effective to vaporize the agent, such as described in U.S. Pat. No. 7,913,688, the disclosure of which is incorporated by reference in its entirety. The heat source can be, for example, an electrical source for producing resistive heating of the substrate, or a chemical heat source for producing substrate heating by initiation of an exothermic reaction. In this manner, the aerosol forming substrate in an aerosol generating device as provided herein can be a solid substrate (e.g., a film or coated solid layer). The heat-conductive substrate can be actuated by a control apparatus as provided herein at a flow-rate around the substrate that is less than 3 LPM. The flow-rate can be less than 1 LPM. The flow-rate can be up to 0.5 LPM. The flow-rate can be about 0.15 LPM.

In some cases, the heater element can comprise a rod comprising electrically resistive material. The rod can be a wire. The wire can be made of any of the electrically resistive/conductive materials described herein. The rod can be a pliable rod. A heater element comprising a rod as provided herein can comprise a coil and a wick element around which the coil can be wrapped. The wick element can be capable of being heated. The wick element can be connected to the rod. The wick element can be independent of the rod. In some cases, the wick element is capable of being heated, and wherein the wick element is connected to the rod. The coil can be a wire coil. The rod can comprise a coil along the entire length of the wick element. The wick element can be capable of wicking or holding a liquid substrate comprising an agent as provided herein. The wick element can be a capillary (a self-wicking tube). The liquid formulation comprising an agent as provided herein can be in fluid communication with a source of the liquid formulation. The source of the liquid formulation can be any source as provided herein, including but not limited to, a reservoir. The liquid formulation comprising an agent as provided herein can be delivered to the wick element by any method known in the art. The delivery can be through capillary action or through the use of a pump. In some cases, the rod comprises a capillary wherein the capillary is in fluid communication with a reservoir, wherein the reservoir comprises a liquid substrate comprising a pharmaceutically active agent (e.g. nicotine), and wherein the capillary is capable of holding the liquid substrate comprising a pharmaceutically active agent (e.g. nicotine). The wick element can be made of any material known in the art capable of wicking or holding a liquid substrate comprising an agent as provided herein. In some cases, the coil connects to a source of electricity. The coil can connect to the source of electricity through one or more leads protruding from both ends of the coil. The source of electricity can be a battery or a charged capacitor. The battery can be rechargeable.

Figure 3:
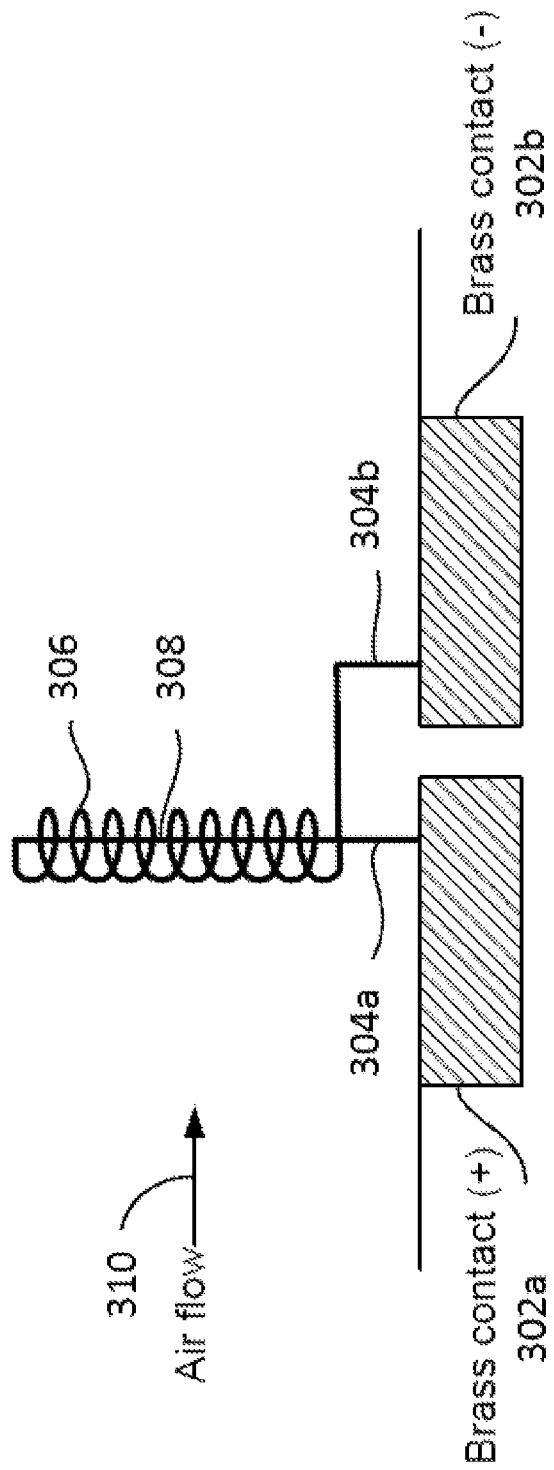
FIG. 3 illustrates an embodiment of a heater element for an aerosol generating device as provided herein.

FIG. 3 illustrates an embodiment of a heater element comprising a pliable rod and a heatable wick element both comprising electrically resistive material as described herein. In this embodiment, a first (302a; +) and a second (302b; −) brass contact or terminal are located adjacent to each other. The brass contacts can be embedded within or placed proximal to a wall of a housing or channel of a device for generating an aerosol as provided herein. The heater element can be a rod comprising electrically resistive material, wherein a first end or lead (304a) is connected to one brass contact (302a; +), while a second end or lead (304b) is connected to another, separate brass contact (302b; As illustrated in FIG. 3, a portion or segment of the rod between the leads is configured into a coil (306). In addition, a separate portion or segment (308) of the rod passes through the interior of the coil (306). Supplying current to the rod through the brass contacts (302a,b) can serve to heat both the coil (306) as well as the segment (308) of the rod that passes through the interior of the coil (306). In some cases, the segment of the rod that runs through the center of the coil is capable of holding a liquid substrate comprising an agent (i.e. nicotine) as provided herein. The liquid substrate can wick or be delivered by any of dosing mechanisms provided herein onto the segment of the rod that runs through the center of the coil from a source of the liquid substrate (e.g., a reservoir). In some cases, supplying current to the rod through the brass contacts (302a,b) serves to heat both the coil (306) as well as the segment (308) of the rod that passes through the interior of the coil (306), wherein a liquid substrate that wicks or is delivered by any of dosing mechanisms provided herein onto the segment of the rod running through the coil is vaporized. In FIG. 3, the coil is oriented perpendicular to the flow of a carrier gas (e.g. air flow) (310). In some cases, the coil is oriented parallel to the flow of a carrier gas (e.g. air flow) in a device for generating an aerosol as described herein.

In some cases a heater element in an aerosol generating device (e.g., electronic cigarette) comprises a foil. A foil of a heater element on an aerosol generating device (e.g., electronic cigarette) can have a thickness of about, more than, less than, or at least 0.0001, 0.00015, 0.0002, 0.00025, 0.0003, 0.00035, 0.0004, 0.00045, 0.0005, 0.00055, 0.0006, 0.00065, 0.0007, 0.00075, 0.0008, 0.00085, 0.0009, 0.00095, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, or 0.99 cm.

Examples of other suitable heater elements for use in the aerosol generating devices provided herein are provided in, e.g., US20120186594A1, US20120285475A1, US20100200008A1, US20110011396A1, US20130087160A1, and US20070074734A1, each of which are incorporated by reference in their entirety.

Control Apparatus

In some cases, an aerosol generating device (e.g., electronic cigarette) as provided herein comprises a control apparatus for regulating activation of a heater element. The heater element can be any heater element as provided herein. The control apparatus can activate the heater element at a trip point or activation trip point as described herein. The control apparatus can comprise a switch. The switch can be configured for detecting air flow or inhalation from the device by a user. In some cases, the switch is constructed to activate the heater element prior to the air-flow rate in an aerosol generation region of an aerosol generating device as provided herein reaching a desired or predetermined rate. Timing of activation is such that the heater element begins vaporization of a substrate (e.g., liquid nicotine solution) at about the time or after the air-flow through the aerosol generation region reaches the desired air-flow rate. In some cases, the heater element is activated when the air-flow rate through the aerosol generation region reaches the desired air-flow rate. In some cases, the heater element is activated at a selected time after the desired flow rate has been reached in the aerosol generation region. The desired rate can be detected in the aerosol generation region. The desired rate can be any rate as provided herein. The desired rate can be any trip point or activation trip point as provided herein. The desired rate can be less than 3 LPM. The desired rate can be less than 1 LPM. The desired rate can be up to 0.5 LPM. The desired rate can be about 0.15 LPM. The switch in the device can be configured for activating the heater element in relation to airflow through the aerosol generation region, such that the heater element produces an aerosol when the air flow rate through the aerosol generation region is sufficient for producing desired-size aerosol particles. The desired-size aerosol particles can comprise a desired diameter. The desired diameter can be from about 1 μm to about 5 μm. The desired diameter can be from about 1 μm to about 3 μm. The desired diameter can be an MMAD or a VMD. The desired-size aerosol particles can be condensation aerosol particles. In some cases, the switch is controlled by airflow through the aerosol generation region, such that the heater element is activated when (or just prior to, or after) the rate of airflow in the device reaches its desired rate. Alternatively, the switch can be user activated, allowing the user to initiate aerosol formation as air is being drawn into the device. In this manner, the device can provide a signal, such as an audible tone, to the user, when the desired rate of airflow through the aerosol generation region is reached.

In some cases, the control apparatus comprises a processor or microprocessor. In some cases, the control apparatus comprises a switch and a processor, wherein the switch detects an air flow rate (or pressure change) due to inhalation by a user and the processor serves to activate the heater element based on data from the sensor. A user inhaling from an outlet of a passageway in an aerosol generating device as provided herein can generate a low pressure region inside the outlet (e.g., mouthpiece). The low pressure region can cause carrier gas (e.g., air) to flow into the passageway through an inlet of the passageway, since the inlet and the outlet form the passageway. The carrier gas (e.g., air) that flows through the passageway can cause instantaneous relative movement or distortion of a detection member of a control apparatus in the device. The detection member can be a sensor as provided herein (e.g., air-flow sensor). This instantaneous relative movement or distortion, or variation in movement or distortion, of the sensor can be transformed into data representing airflow rate (and/or direction) when interpreted by a microprocessor of the control apparatus. When the detected airflow rate reaches a predetermined or desired rate, the microprocessor can activate the battery to operate the heater element of the device to cause vaporization of a substrate (e.g., liquid nicotine solution) inside an aerosol generation region of the passageway and generated aerosol particles can pass from the outlet (e.g., mouth piece) to the user. The desired rate can be detected in the aerosol generation region. The desired rate can be any rate as provided herein. The desired rate can be any trip point or activation trip point as provided herein. The desired rate can be less than 3 LPM. The desired rate can be less than 1 LPM. The desired rate can be up to 0.5 LPM. The desired rate can be about 0.15 LPM. The generated aerosol particles can comprise a diameter of from about 1 µm to about 5 µm. The generated aerosol particles can comprise a diameter of from about 1 µm to about 3 µm. The diameter can be an MMAD or a VMD. The desired-size aerosol particles can be condensation aerosol particles.

In some cases, a control apparatus as provided herein comprises a switch, wherein the switch comprises a puff or breath actuated sensor. The breath actuated sensor can be referred to as an air-flow sensor. The air-flow sensor can be a pressure sensor or an optical sensor. A breath actuated sensor can be a semiconductor force-sensitive chip capacitance sensor or an inductance sensor. The breath actuated or air-flow switch can be sensitive either to pressure changes or air flow changes as the user draws on the device. A control apparatus can include one or more control components responsive to a user drawing on the article (i.e., puff-actuated heating). Other suitable current actuation/deactuation mechanisms can include a temperature actuated on/off switch or a lip pressure actuated switch. An exemplary mechanism that can provide such breath-actuation capability includes a Model 163PC01D36 silicon sensor, manufactured by the MicroSwitch division of Honeywell, Inc., Freeport, Ill. In such a sensor, the heater element (e.g., resistive heater element) can be activated rapidly by a change in pressure when the user draws on the article. In addition, flow sensing devices, such as those using hot-wire anemometry principles, can be used to cause the energizing of the heater element (e.g., resistive heater element) sufficiently rapidly after sensing a change in air flow. A further breath actuated switch that can be used is a pressure differential switch, such as Model No. MPL-502-V, range A, from Micro Pneumatic Logic, Inc., Ft. Lauderdale, Fla. Another suitable breath actuated mechanism can be a sensitive pressure transducer (e.g., equipped with an amplifier or gain stage) which is in turn coupled with a comparator for detecting a predetermined threshold pressure. Yet another suitable breath actuated mechanism is a vane which is deflected by airflow, the motion of which vane is detected by a movement sensing device. Yet another suitable actuation mechanism can be a piezoelectric switch. Also useful is a suitably connected Honeywell MicroSwitch Microbridge Airflow Sensor, Part No. AWM 2100V from MicroSwitch Division of Honeywell, Inc., Freeport, Ill. Further examples of demand-operated electrical switches that can be employed in a heater element in a device as provided herein are described in U.S. Pat. No. 4,735,217, which is incorporated herein by reference in its entirety. Other suitable differential switches, analog pressure sensors, flow rate sensors, or the like, will be apparent to one skilled in the art. A pressure-sensing tube or other passage providing fluid connection between the breath actuated switch and an air flow channel (or passageway) within a device as provided herein can be included so that pressure changes during draw are readily identified by the switch. Further description of current regulating circuits and other control components, including microcontrollers that can be useful in the devices provided herein are provided in U.S. Pat. Nos. 4,922,901, 4,947,874, and 4,947,875, U.S. Pat. No. 5,372,148, U.S. Pat. No. 6,040,560, and U.S. Pat. No. 7,040,314, all of which are incorporated herein by reference in their entireties. In some cases, the control apparatus is in electrical communication with the heater element. The electrical communication can be direct or indirect. In some cases, the control apparatus is a valve or flap as provided herein, wherein the valve or flap comprises an electrical component that serves to control activation of the heater element. The valve or flap can be a gas-control valve or flap.

In some cases, a control apparatus in an aerosol generating device as provided herein comprises a switch that comprises a diaphragm. The switch can be an air-flow switch. The diaphragm can be a component of a pressure sensor in the air-flow switch. In some cases, a diaphragm in a switch is configured to be responsive to a flow rate of a carrier gas (e.g., air) that generates aerosol particles with a selected size. The diaphragm can be composed of materials comprising a modulus of elasticity that is responsive to the flow rate of a carrier gas (e.g., air) that generates aerosol particles with a selected size. The select flow rate can be any flow rate for a carrier gas (e.g., air) as provided herein. In some cases, the flow rate is less than 3 LPM. The flow rate is less than 1 LPM. The flow rate can be up to 0.5 LPM. The flow rate can be about 0.15 LPM. The generated aerosol particles can comprise a diameter of from about 1 µm to about 5 µm. The generated aerosol particles can comprise a diameter of from about 1 µm to about 3 µm. The diameter can be an MMAD or a VMD. The desired-size aerosol particles can be condensation aerosol particles. The diaphragm can comprise electrical contacts. In some cases, a switch in a control apparatus in an aerosol generating device as provided herein comprises a diaphragm and a first and a second electrical contact such that the first electrical contact is located on the diaphragm while the second electrical contact is located on a fixed point some distance away from the first electrical contact. The distance between the first and second electrical contacts can be such that the flow rate or vacuum pressure associated with the flow rate of a carrier gas (e.g., air) needed to bring the first and the second electrical contacts in contact with each other via movement of the diaphragm is the flow rate or vacuum pressure associated with the flow rate of a carrier gas (e.g., air) required to generate aerosol particles of a select size. The flow rate or vacuum pressure associated with the flow rate of a carrier gas (e.g., air) detected by the switch can be in the aerosol generation region of a device as provided herein. The flow rate or vacuum pressure associated with the flow rate of a carrier gas (e.g., air) detected by the switch can be in region upstream or downstream of the aerosol generation region of a device as provided herein. In some cases, a diameter of a diaphragm in a switch in a control apparatus of an aerosol generating device as provided herein is greater than the diameter of the diaphragm in the switch (e.g., air-flow switch) of a conventional electronic cigarette. In some cases, a distance between electrical contacts separated by a diaphragm in a switch in a control apparatus of an aerosol generating device as provided herein is shorter than the distance between electrical contacts separated by the diaphragm in the switch (e.g., air-flow switch) of a conventional electronic cigarette. The conventional electronic cigarette can be a N Joy King Bold or Finiti e-cigarette.

Trip Point

In some cases, aerosol generating device comprises a control apparatus, wherein the control apparatus governs a trip point. In some cases, the aerosol generating device is an electronic cigarette. In some cases, the control apparatus of the aerosol generating device is breath actuated such that the control apparatus is configured to activate the heater element at a set flow rate of a carrier gas (e.g., air) or vacuum applied to the device that results in the flow rate of the carrier gas (e.g., air). The set flow rate of a carrier gas (e.g., air) or vacuum applied to the device that results in the flow rate of the carrier gas (e.g., air) can be the trip point. An aerosol can be produced (triggered) by the control apparatus of an aerosol generating device (e.g., electronic cigarette) at an activation trip point. The control apparatus can be in electrical communication with the heater element. A trip point can be a flow rate (or vacuum applied to the mouthpiece that can result in a flow rate) which causes an electrical current to be applied to a heater element, which activates (heats) the heater element and results in generation of an aerosol from a substrate in contact with the heater element. The flow rate (or vacuum applied to the mouthpiece that can result in a flow rate) can be detected by the control apparatus, wherein the control apparatus can subsequently activate the heater element. In some cases, a flow rate that is detected by the control apparatus and causes the control apparatus to activate a heater element of an aerosol generating device is the flow rate at which an aerosol comprising a desired diameter is generated following vaporization of a substrate in contact with the activated heater element. The desired diameter can be from about 1 μm to about 5 μm. The diameter can be an MMAD. The diameter can be a VMD. An aerosol generating device (e.g., electronic cigarette) can have an activation trip point of about, more than, less than, or at least 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 liters per minute (LPM). In some cases, a trip point is less than 3 LPM. In some cases, a trip point is less than 1 LPM. In some cases, a trip point is up to 0.5 LPM. In some cases, a trip point is about 0 to about 0.5 LPM, about 0.01 to about 0.5 LPM, about 0.05 to about 0.5 LPM, about 0.1 to about 0.2 LPM, or about 0.075 to about 0.175 LPM.

An aerosol generating device (e.g., electronic cigarette) can have an activation trip point at a vacuum of about, more than, less than, or at least 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 1, 1.1, 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 11.5, or 12 inches of $H_2O$ (0.127, 0.254, 0.381, 0.508, 0.635, 0.762, 0.889, 1.016, 1.143, 1.27, 1.397, 1.524, 1.651, 1.778, 1.905, 2.032, 2.159, 2.286, 2.54, 2.794, 3.048, 3.302, 3.556, 3.81, 4.064, 4.318, 4.572, 4.862, 5.08, 6.35, 7.62, 8.89, 10.16, 11.43, 12.7, 13.97, 15.24, 16.51, 17.78, 19.05, 20.32, 21.59, 22.86, 24.13, 25.4, 26.67, 27.94, 29.21, or 30.48 cm). In some cases, an aerosol generating (e.g., electronic cigarette) has an activation trip point at a vacuum of about 0.1 to about 1 inches of $H_2O$ (about 0.254 to about 2.54 cm of $H_2O$), about 0.1 to about 0.75 inches of $H_2O$ (about 0.254 to about 1.905 cm of $H_2O$), about 0.5 to about 1.5 inches of $H_2O$ (about 1.27 to about 3.81 cm of $H_2O$), about 0.05 to about 0.5 inches of $H_2O$ (about 0.127 to about 1.27 cm of $H_2O$), about 0.1 to about 0.5 inches of $H_2O$ (about 0.254 to about 1.27 cm of $H_2O$), about 0.25 to about 0.75 inches of $H_2O$ (about 0.635 to about 1.905 cm of $H_2O$), about 1 to about 1.5 inches of $H_2O$ (about 2.54 to about 3.81 cm of $H_2O$), about 0.9 to about 1.1 inches of $H_2O$ (about 2.286 to about 2.794 cm of $H_2O$), about 0.8 to about 1.2 inches of $H_2O$ (about 2.159 to about 3.048 cm of $H_2O$), about 0.7 to about 1.3 inches of $H_2O$ (about 2.032 to about 3.302 cm of $H_2O$), about 0.9 to about 1.2 inches of $H_2O$ (about 2.286 to about 3.048 cm of $H_2O$), about 0.9 to about 1.3 inches of $H_2O$ (about 2.286 to about 3.302 cm of $H_2O$), about 1.5 to about 2 inches of water (about 3.81 to about 5.08 cm of water), about 2 to about 2.5 inches of water (about 5.08 to about 6.35 cm of water), about 2.5 to about 3 inches of water (about 6.35 to about 7.62 cm of water), about 3 to about 3.5 inches of water (about 7.62 to about 8.89 cm of water), about 3.5 to about 4 inches of water (about 8.89 to about 10.16 cm of water), about 4 to about 4.5 inches of water (about 10.16 to about 11.43 cm of water), about 4.5 to about 5 inches of water (about 11.43 to about 12.7 cm of water), about 5 to about 5.5 inches of water (about 12.7 to about 13.97 cm of water), about 5.5 to about 6 inches of water (about 13.97 to about 15.24 cm of water), about 6 to about 6.5 inches of water (about 15.24 to about 16.51 cm of water), about 6.5 to about 7 inches of water (about 16.51 to about 17.78 cm of water), about 7 to about 7.5 inches of water (about 17.78 to about 19.05 cm of water), about 7.5 to about 8 inches of water (about 19.05 to about 20.32 cm of water), about 8 to about 8.5 inches of water (about 20.32 to about 21.59 cm of water), about 8.5 to about 9 inches of water (about 21.59 to about 22.86 cm of water), about 9 to about 9.5 inches of water (about 22.86 to about 24.13 cm of water), about 9.5 to about 10 inches of water (about 24.13 to about 25.4 cm of water), about 10 to about 10.5 inches of water (about 25.4 to about 26.67 cm of water), about 10.5 to about 11 inches of water (about 26.67 to about 27.94 cm of water), about 11 to about 11.5 inches of water (about 27.94 to about 29.21 cm of water), about 11.5 to about 12 inches of water (about 29.21 to about 30.48 cm of water), about 0.25 to about 5 inches of water (about 0.635 to about 12.7 cm of water), about 1 to about 5 inches of water (about 2.54 to about 12.7 cm of water), or about 0.5 to about 4 inches of water (or about 1.27 to about 10.16 cm of water).

An aerosol generating device (e.g., electronic cigarette) as provided herein can be activated automatically or manually. Automatic aerosol generating devices (e.g., electronic cigarettes) can be activated by inhalation, which can lead to the vaporization of a substrate (e.g., nicotine solution). Activation can comprise heating of a heater element in an aerosol generating devices (e.g., electronic cigarettes) as described herein. Users of a manual aerosol generating device (e.g., electronic cigarette) can depress, e.g., a button to activate the aerosol generating device (e.g., electronic cigarette), and can inhale to transfer a vaporized solution to the lung. In some cases, a manual aerosol generating device (e.g., electronic cigarette) is activated by moving a switch. In some cases, an aerosol generating device (e.g., electronic cigarette) as provided herein is activated remotely. In some cases, an aerosol generating device (e.g., electronic cigarette) as provided herein comprises a lockout mechanism. The lockout mechanism can deactivate the device.

Figure 4:
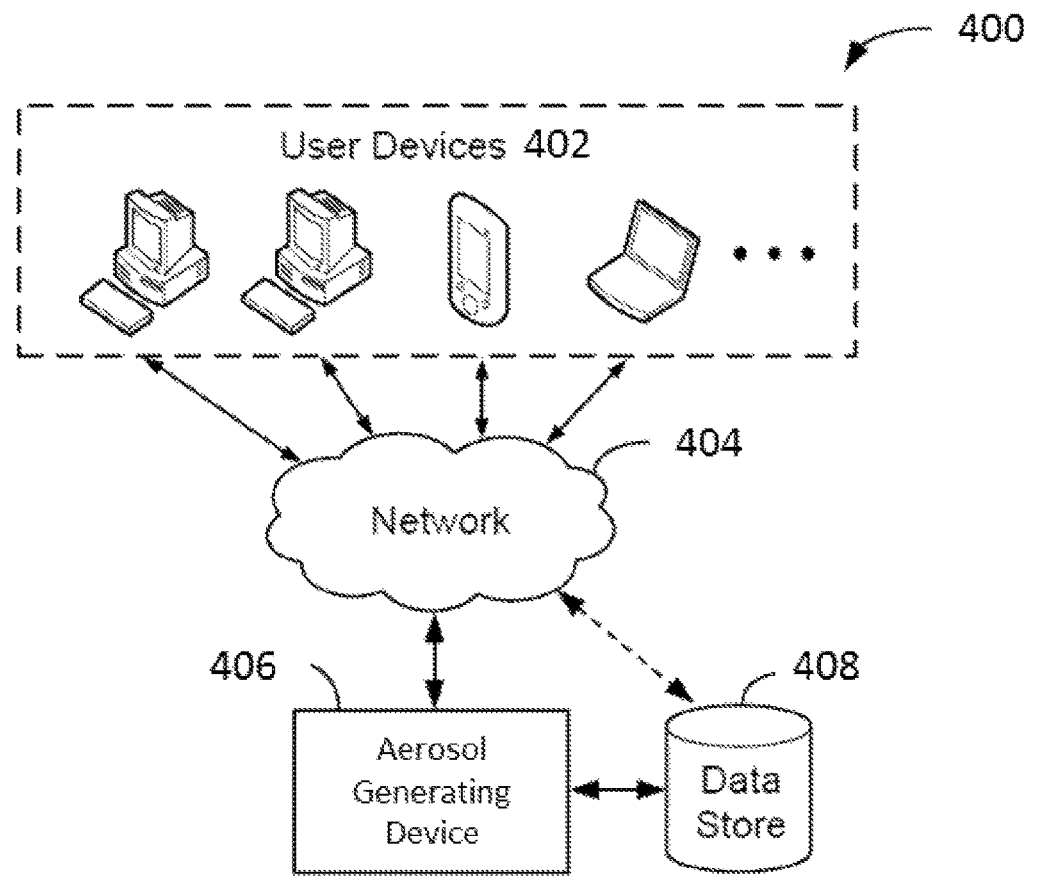

FIG. 4 illustrates an example environment 400 for implementing devices and methods described herein in accordance with an embodiment. As illustrated, one or more user devices 402 connect via a network 404 to an aerosol generating device 406 as provided herein which can be configured to produce an aerosol (e.g., condensation aerosol) comprising a pharmaceutically active agent (e.g., nicotine) as provided herein. The device 406 can comprise a controller, which can be programmable, as provided herein and the device 406 can be connected to the network 404 through the programmable controller. In some cases, the aerosol comprising the pharmaceutically active agent (e.g., nicotine) is produced from a liquid formulation comprising the pharmaceutically active agent (e.g., nicotine) as provided herein. In various embodiments, the user devices 402 can include any device capable of communicating with the network 404, such as personal computers, workstations, laptops, smartphones, mobile phones, tablet computing devices, smart TVs, game consoles, internet-connected set up boxes, and the like. In some embodiments, the user devices 402 can include applications such as web browsers and/or applications (e.g., mobile apps) that are capable of communicating with the device 406 and/or a system that uses the device 406. In some cases, the user devices 402 communicate with the device 406 via the controller as provided herein. The user can be a patient, and/or a healthcare provider (e.g., physician, physician's assistant, nurse, nurse practitioner, pharmacist or other medical professional). In some cases, a first user uses the device, while a second user uses the other user devices 402. In some cases, a first user uses the device and the other user devices 402, while the second user also uses the user devices 402.

In some embodiments, an aerosol generating device 406 can communicate with a data store 408 in order to perform functionalities such as track device usage, adjust dose, frequency of administration, delivery schedule, customize feedback, administer challenge doses, etc. For example, the data store 408 can be used to store historical (e.g. user use history, dosage history, delivery schedule history, frequency of administration history, etc.), evaluation rules, and the like.

In some embodiments, the data store 408, or any other data stores discussed herein, can include one or more data files, databases, (e.g., SQL database), data storage devices (e.g., tape, hard disk, solid-state drive), data storage servers, or the like. The data store 408 can be connected to the aerosol generating device 406 locally or remotely via a network. In some embodiments, data store 408, or any other data stores discussed herein, can comprise one or more storage services provisioned from a "cloud storage" provider, for example, Amazon Simple Storage Service ("Amazon S3"), provided by Amazon.com, Inc. of Seattle, Wash., Google Cloud Storage, provided by Google, Inc. of Mountain View, Calif., and the like.

In various embodiments, the network 404 can include the Internet, a local area network ("LAN"), a wide area network ("WAN"), a cellular network, wireless network or any other public or private data and/or telecommunication network.

An aerosol generating device as provided herein can comprise a combination of features that are configured to generate an aerosol from a substrate such that the aerosol comprises particles of a selected size. The aerosol can be a condensation aerosol. The substrate can be a solid substrate. The substrate can be a liquid formulation. The substrate can comprise a pharmaceutically active agent (e.g., nicotine). In some cases, an aerosol generating device as provided herein comprises a liquid formulation comprising nicotine. The selected size can be a selected diameter. The selected diameter can be a diameter from about 1 μm to about 5 μm. The selected diameter can be a diameter from about 1 μm to about 3 μm. The selected diameter can be an MMAD. The selected diameter can be a VMD. In some cases, an aerosol generating device comprises a control apparatus for activating a heater element at a select air flow rate in an aerosol generation region of the device such that the aerosol generating device comprises a set of additional features as shown in each row of Table 1. The aerosol generating devices as outlined in Table 1 can comprise a housing such that each of the features including the control apparatus are contained within the housing. The housing can be elongated. The housing can be cylindrical. The housing can be an elongated cylinder. The select air flow rate can be less than 3 LPM. The select air flow rate can be less than 1 LPM. The select air flow rate can be up to 0.5 LPM. The select air flow rate can be about 0.15 LPM. In Table 1, the wicking element can be a fibrous material. In Table 1, the wicking can be in the shape of a rod, cylinder, or planar surface. In Table 1, the wicking element can be a plurality of wicking elements arranged in a bundle. Each of the aerosol generating devices depicted in the rows of Table 1 can be configured to have an inhalation resistance (i.e., resistance to draw) of no greater than that of a combustible, tobacco cigarette. Each of the aerosol generating devices depicted in the rows of Table 1 can be configured to have an inhalation resistance (i.e., resistance to draw) of from about 1 (cm $H_2O)^{1/2}$/LPM to about 2.5 (cm $H_2O)^{1/2}$/LPM. Each of the aerosol generating devices depicted in the rows of Table 1 can be configured to have an inhalation resistance (i.e., resistance to draw) of less than about 1 (cm $H_2O)^{1/2}$/LPM. Each of the aerosol generating devices depicted the rows of Table 1 can be configured to have an inhalation resistance (i.e., resistance to draw) of no greater than about 0.15 (cm $H_2O)^{1/2}$/LPM.

TABLE 1

Exemplary combinations of features in an aerosol generating device comprising a control apparatus.

| Substrate Type | Heating or Aerosolization Mechanism | Flow regulation | Fluid delivery mechanism |
|---|---|---|---|
| liquid formulation^ | Electrically resistive coil surrounding a wicking element* | Second inlets configured to allow entry of entrainment carrier gas (e.g., air), wherein the second inlets are located between aerosol generation region and an outlet of an airflow channel | Wicking element is in direct contact with liquid formulation |
| liquid formulation^ | Electrically resistive coil surrounding a wicking element* | Second inlets configured to allow entry of entrainment carrier gas (e.g., air), wherein the second inlets are located between aerosol generation region and an outlet of an airflow channel | Pump configured to deposit liquid formulation onto heater element |
| liquid formulation^ | Electrically resistive coil surrounding a wicking element* | One or more bypass flow channels configured to route entrainment carrier gas (e.g., air) that enters from an inlet upstream of aerosol an generation region around aerosol generation region | Wicking element is in direct contact with liquid formulation |
| liquid formulation^ | Electrically resistive coil surrounding a wicking element* | One or more bypass flow channels configured to route entrainment carrier gas (e.g., air) that enters from an inlet upstream of an aerosol generation region around aerosol generation region | Pump configured to deposit liquid formulation onto heater element |
| liquid formulation^ | Electrically resistive coil surrounded by wicking element | Second inlets configured to allow entry of entrainment carrier gas (e.g., air), wherein the second inlets are located between aerosol generation region and an outlet of an airflow channel | Wicking element is in direct contact with liquid formulation |
| liquid formulation^ | Electrically resistive coil surrounded by wicking element | Second inlets configured to allow entry of entrainment carrier gas (e.g., air), wherein the second inlets are located between aerosol generation region and an outlet of an airflow channel | Pump configured to deposit liquid formulation onto heater element |
| liquid formulation^ | Electrically resistive coil surrounded by wicking element | One or more bypass flow channels configured to route entrainment carrier gas (e.g., air) that enters from an inlet upstream of an aerosol generation region around aerosol generation region | Wicking element is in direct contact with liquid formulation |
| liquid formulation^ | Electrically resistive coil surrounded by wicking element | One or more bypass flow channels configured to route entrainment carrier gas (e.g., air) that enters from an inlet upstream of an aerosol generation region around aerosol generation region | Pump configured to deposit liquid formulation onto heater element |
| liquid formulation^ | Vaporization nozzle surrounded by electrically resistive coil | Second inlets configured to allow entry of entrainment carrier gas (e.g., air), wherein the second inlets are located between aerosol generation region and an outlet of an airflow channel | Wicking element is in direct contact with liquid formulation |
| liquid formulation^ | Vaporization nozzle surrounded by electrically resistive coil | Second inlets configured to allow entry of entrainment carrier gas (e.g., air), wherein the second inlets are located between aerosol generation region and an outlet of an airflow channel | Pump configured to deposit liquid formulation onto heater element |

TABLE 1-continued

Exemplary combinations of features in an aerosol generating device comprising a control apparatus.

| Substrate Type | Heating or Aerosolization Mechanism | Flow regulation | Fluid delivery mechanism |
| --- | --- | --- | --- |
| liquid formulation^ | Vaporization nozzle surrounded by electrically resistive coil | One or more bypass flow channels configured to route entrainment carrier gas (e.g., air) that enters from an inlet upstream of an aerosol generation region around aerosol generation region | Wicking element is in direct contact with liquid formulation |
| liquid formulation^ | Vaporization nozzle surrounded by electrically resistive coil | One or more bypass flow channels configured to route entrainment carrier gas (e.g., air) that enters from an inlet upstream of an aerosol generation region around aerosol generation region | Pump configured to deposit liquid formulation onto heater element |
| liquid formulation^ | Vaporization nozzle with electrically resistive coil within the nozzle | Second inlets configured to allow entry of entrainment carrier gas (e.g., air), wherein the second inlets are located between aerosol generation region and an outlet of an airflow channel | Wicking element is in direct contact with liquid formulation |
| liquid formulation^ | Vaporization nozzle with electrically resistive coil within the nozzle | Second inlets configured to allow entry of entrainment carrier gas (e.g., air), wherein the second inlets are located between aerosol generation region and an outlet of an airflow channel | Pump configured to deposit liquid formulation onto heater element |
| liquid formulation^ | Vaporization nozzle with electrically resistive coil within the nozzle | One or more bypass flow channels configured to route entrainment carrier gas (e.g., air) that enters from an inlet upstream of an aerosol generation region around aerosol generation region | Wicking element is in direct contact with liquid formulation |
| liquid formulation^ | Vaporization nozzle with electrically resistive coil within the nozzle | One or more bypass flow channels configured to route entrainment carrier gas (e.g., air) that enters from an inlet upstream of an aerosol generation region around aerosol generation region | Pump configured to deposit liquid formulation onto heater element |
| liquid formulation^ | Vaporization nozzle comprising electrically resistive material | Second inlets configured to allow entry of entrainment carrier gas (e.g., air), wherein the second inlets are located between aerosol generation region and an outlet of an airflow channel | Wicking element is in direct contact with liquid formulation |
| liquid formulation^ | Vaporization nozzle comprising electrically resistive material | Second inlets configured to allow entry of entrainment carrier gas (e.g., air), wherein the second inlets are located between aerosol generation region and an outlet of an airflow channel | Pump configured to deposit liquid formulation onto heater element |
| liquid formulation^ | Vaporization nozzle comprising electrically resistive material | One or more bypass flow channels configured to route entrainment carrier gas (e.g., air) that enters from an inlet upstream of an aerosol generation region around aerosol generation region | Wicking element is in direct contact with liquid formulation |
| liquid formulation^ | Vaporization nozzle comprising electrically resistive material | One or more bypass flow channels configured to route entrainment carrier gas (e.g., air) that enters from an inlet upstream of an aerosol generation region around aerosol generation region | Pump configured to deposit liquid formulation onto heater element |

TABLE 1-continued

Exemplary combinations of features in an aerosol generating device comprising a control apparatus.

| Substrate Type | Heating or Aerosolization Mechanism | Flow regulation | Fluid delivery mechanism |
|---|---|---|---|
| liquid formulation^ | Droplet ejection device | Second inlets configured to allow entry of entrainment carrier gas (e.g., air), wherein the second inlets are located between aerosol generation region and an outlet of an airflow channel | Wicking element is in direct contact with liquid formulation |
| liquid formulation^ | Droplet ejection device | Second inlets configured to allow entry of entrainment carrier gas (e.g., air), wherein the second inlets are located between aerosol generation region and an outlet of an airflow channel | Pump configured to deposit liquid formulation onto heater element |
| liquid formulation^ | Droplet ejection device | One or more bypass flow channels configured to route entrainment carrier gas (e.g., air) that enters from an inlet upstream of an aerosol generation region around aerosol generation region | Wicking element is in direct contact with liquid formulation |
| liquid formulation^ | Droplet ejection device | One or more bypass flow channels configured to route entrainment carrier gas (e.g., air) that enters from an inlet upstream of an aerosol generation region around aerosol generation region | Pump configured to deposit liquid formulation onto heater element |
| liquid formulation^ | Droplet ejection device and a heater element | Second inlets configured to allow entry of entrainment carrier gas (e.g., air), wherein the second inlets are located between aerosol generation region and an outlet of an airflow channel | Wicking element is in direct contact with liquid formulation |
| liquid formulation^ | Droplet ejection device and a heater element | Second inlets configured to allow entry of entrainment carrier gas (e.g., air), wherein the second inlets are located between aerosol generation region and an outlet of an airflow channel | Pump configured to deposit liquid formulation onto heater element |
| liquid formulation^ | Droplet ejection device and a heater element | One or more bypass flow channels configured to route entrainment carrier gas (e.g., air) that enters from an inlet upstream of an aerosol generation region around aerosol generation region | Wicking element is in direct contact with liquid formulation |
| liquid formulation^ | Droplet ejection device and a heater element | One or more bypass flow channels configured to route entrainment carrier gas (e.g., air) that enters from an inlet upstream of an aerosol generation region around aerosol generation region | Pump configured to deposit liquid formulation onto heater element |
| Solid substrate | Heat conductive substrate coated with agent (e.g., nicotine) | Second inlets configured to allow entry of entrainment carrier gas (e.g., air), wherein the second inlets are located between aerosol generation region and an outlet of an airflow channel | Wicking element is in direct contact with liquid formulation |
| Solid substrate | Heat conductive substrate coated with agent (e.g., nicotine) | Second inlets configured to allow entry of entrainment carrier gas (e.g., air), wherein the second inlets are located between aerosol generation region and an outlet of an airflow channel | Pump configured to deposit liquid formulation onto heater element |

TABLE 1-continued

Exemplary combinations of features in an aerosol generating device comprising a control apparatus.

| Substrate Type | Heating or Aerosolization Mechanism | Flow regulation | Fluid delivery mechanism |
|---|---|---|---|
| Solid substrate | Heat conductive substrate coated with agent (e.g., nicotine) | One or more bypass flow channels configured to route entrainment carrier gas (e.g., air) that enters from an inlet upstream of an aerosol generation region around aerosol generation region | Wicking element is in direct contact with liquid formulation |
| Solid substrate | Heat conductive substrate coated with agent (e.g., nicotine) | One or more bypass flow channels configured to route entrainment carrier gas (e.g., air) that enters from an inlet upstream of an aerosol generation region around aerosol generation region | Pump configured to deposit liquid formulation onto heater element |

^Liquid formulation can be housed in reservoir (e.g., collapsible bag).
*The wicking element and wire coil can be made from a single pliable rod.

In some cases, an aerosol generating device comprises an aerosol generation region with a cross-sectional area configured to generate aerosol particles with a selected size at a selected flow rate through the aerosol generation region such that the aerosol generating device comprises a set of additional features as shown in each row of Table 2. The aerosol generating devices as outlined in Table 2 can comprise a housing such that each of the features are contained within the housing. The housing can be elongated. The housing can be cylindrical. The housing can be an elongated cylinder. The selected air flow rate can be about 1.0 to about 2.0 LPM. The select size can be a selected diameter. The selected diameter can be a diameter from about 1 μm to about 5 μm. The selected diameter can be a diameter from about 1 μm to about 3 μm. The selected diameter can be an MMAD. The selected diameter can be a VMD. In Table 2, the wicking element can be a fibrous material. In Table 2, the wicking can be in the shape of a rod, cylinder, or planar surface. In Table 2, the wicking element can be a plurality of wicking elements arranged in a bundle. Each of the aerosol generating devices depicted in the rows of Table 2 can be configured to have an inhalation resistance (i.e., resistance to draw) of no greater than that of a combustible, tobacco cigarette. Each of the aerosol generating devices depicted in the rows of Table 2 can be configured to have an inhalation resistance (i.e., resistance to draw) of from about 1 (cm $H_2O)^{1/2}$/LPM to about 2.5 (cm $H_2O)^{1/2}$/LPM. Each of the aerosol generating devices depicted in the rows of Table 2 can be configured to have an inhalation resistance (i.e., resistance to draw) of less than about 1 (cm $H_2O)^{1/2}$/LPM. Each of the aerosol generating devices depicted the rows of Table 2 can be configured to have an inhalation resistance (i.e., resistance to draw) of no greater than about 0.15 (cm $H_2O)^{1/2}$/LPM.

TABLE 2

Exemplary combinations of features in an aerosol generating device comprising an aerosol generation region with a cross-sectional area configured to generate select particle sizes.

| Substrate Type | Heating or Aerosolization Mechanism | Flow regulation | Fluid delivery mechanism |
|---|---|---|---|
| liquid formulation^ | Electrically resistive coil surrounding a wicking element* | Second inlets configured to allow entry of entrainment carrier gas (e.g., air), wherein the second inlets are located between aerosol generation region and an outlet of an airflow channel | Wicking element is in direct contact with liquid formulation |
| liquid formulation^ | Electrically resistive coil surrounding a wicking element* | Second inlets configured to allow entry of entrainment carrier gas (e.g., air), wherein the second inlets are located between aerosol generation region and an outlet of an airflow channel | Pump configured to deposit liquid formulation onto heater element |
| liquid formulation^ | Electrically resistive coil surrounding a wicking element* | One or more bypass flow channels configured to route entrainment carrier gas (e.g., air) that enters from an inlet upstream of an aerosol generation region around aerosol generation region | Wicking element is in direct contact with liquid formulation |

TABLE 2-continued

Exemplary combinations of features in an aerosol generating device comprising an aerosol generation region with a cross-sectional area configured to generate select particle sizes.

| Substrate Type | Heating or Aerosolization Mechanism | Flow regulation | Fluid delivery mechanism |
|---|---|---|---|
| liquid formulation^ | Electrically resistive coil surrounding a wicking element* | One or more bypass flow channels configured to route entrainment carrier gas (e.g., air) that enters from an inlet upstream of an aerosol generation region around aerosol generation region | Pump configured to deposit liquid formulation onto heater element |
| liquid formulation^ | Electrically resistive coil surrounded by wicking element | Second inlets configured to allow entry of entrainment carrier gas (e.g., air), wherein the second inlets are located between aerosol generation region and an outlet of an airflow channel | Wicking element is in direct contact with liquid formulation |
| liquid formulation^ | Electrically resistive coil surrounded by wicking element | Second inlets configured to allow entry of entrainment carrier gas (e.g., air), wherein the second inlets are located between aerosol generation region and an outlet of an airflow channel | Pump configured to deposit liquid formulation onto heater element |
| liquid formulation^ | Electrically resistive coil surrounded by wicking element | One or more bypass flow channels configured to route entrainment carrier gas (e.g., air) that enters from an inlet upstream of an aerosol generation region around aerosol generation region | Wicking element is in direct contact with liquid formulation |
| liquid formulation^ | Electrically resistive coil surrounded by wicking element | One or more bypass flow channels configured to route entrainment carrier gas (e.g., air) that enters from an inlet upstream of an aerosol generation region around aerosol generation region | Pump configured to deposit liquid formulation onto heater element |
| liquid formulation^ | Vaporization nozzle surrounded by electrically resistive coil | Second inlets configured to allow entry of entrainment carrier gas (e.g., air), wherein the second inlets are located between aerosol generation region and an outlet of an airflow channel | Wicking element is in direct contact with liquid formulation |
| liquid formulation^ | Vaporization nozzle surrounded by electrically resistive coil | Second inlets configured to allow entry of entrainment carrier gas (e.g., air), wherein the second inlets are located between aerosol generation region and an outlet of an airflow channel | Pump configured to deposit liquid formulation onto heater element |
| liquid formulation^ | Vaporization nozzle surrounded by electrically resistive coil | One or more bypass flow channels configured to route entrainment carrier gas (e.g., air) that enters from an inlet upstream of an aerosol generation region around aerosol generation region | Wicking element is in direct contact with liquid formulation |
| liquid formulation^ | Vaporization nozzle surrounded by electrically resistive coil | One or more bypass flow channels configured to route entrainment carrier gas (e.g., air) that enters from an inlet upstream of an aerosol generation region around aerosol generation region | Pump configured to deposit liquid formulation onto heater element |
| liquid formulation^ | Vaporization nozzle with electrically resistive coil within the nozzle | Second inlets configured to allow entry of entrainment carrier gas (e.g., air), wherein the second inlets are located between aerosol generation region and an outlet of an airflow channel | Wicking element is in direct contact with liquid formulation |

TABLE 2-continued

Exemplary combinations of features in an aerosol generating device comprising an aerosol generation region with a cross-sectional area configured to generate select particle sizes.

| Substrate Type | Heating or Aerosolization Mechanism | Flow regulation | Fluid delivery mechanism |
|---|---|---|---|
| liquid formulation^ | Vaporization nozzle with electrically resistive coil within the nozzle | Second inlets configured to allow entry of entrainment carrier gas (e.g., air), wherein the second inlets are located between aerosol generation region and an outlet of an airflow channel | Pump configured to deposit liquid formulation onto heater element |
| liquid formulation^ | Vaporization nozzle with electrically resistive coil within the nozzle | One or more bypass flow channels configured to route entrainment carrier gas (e.g., air) that enters from an inlet upstream of an aerosol generation region around aerosol generation region | Wicking element is in direct contact with liquid formulation |
| liquid formulation^ | Vaporization nozzle with electrically resistive coil within the nozzle | One or more bypass flow channels configured to route entrainment carrier gas (e.g., air) that enters from an inlet upstream of an aerosol generation region around aerosol generation region | Pump configured to deposit liquid formulation onto heater element |
| liquid formulation^ | Vaporization nozzle comprising electrically resistive material | Second inlets configured to allow entry of entrainment carrier gas (e.g., air), wherein the second inlets are located between aerosol generation region and an outlet of an airflow channel | Wicking element is in direct contact with liquid formulation |
| liquid formulation^ | Vaporization nozzle comprising electrically resistive material | Second inlets configured to allow entry of entrainment carrier gas (e.g., air), wherein the second inlets are located between aerosol generation region and an outlet of an airflow channel | Pump configured to deposit liquid formulation onto heater element |
| liquid formulation^ | Vaporization nozzle comprising electrically resistive material | One or more bypass flow channels configured to route entrainment carrier gas (e.g., air) that enters from an inlet upstream of an aerosol generation region around aerosol generation region | Wicking element is in direct contact with liquid formulation |
| liquid formulation^ | Vaporization nozzle comprising electrically resistive material | One or more bypass flow channels configured to route entrainment carrier gas (e.g., air) that enters from an inlet upstream of an aerosol generation region around aerosol generation region | Pump configured to deposit liquid formulation onto heater element |
| liquid formulation^ | Droplet ejection device | Second inlets configured to allow entry of entrainment carrier gas (e.g., air), wherein the second inlets are located between aerosol generation region and an outlet of an airflow channel | Wicking element is in direct contact with liquid formulation |
| liquid formulation^ | Droplet ejection device | Second inlets configured to allow entry of entrainment carrier gas (e.g., air), wherein the second inlets are located between aerosol generation region and an outlet of an airflow channel | Pump configured to deposit liquid formulation onto heater element |
| liquid formulation^ | Droplet ejection device | One or more bypass flow channels configured to route entrainment carrier gas (e.g., air) that enters from an inlet upstream of an aerosol generation region around aerosol generation region | Wicking element is in direct contact with liquid formulation |

TABLE 2-continued

Exemplary combinations of features in an aerosol generating device comprising an aerosol generation region with a cross-sectional area configured to generate select particle sizes.

| Substrate Type | Heating or Aerosolization Mechanism | Flow regulation | Fluid delivery mechanism |
|---|---|---|---|
| liquid formulation^ | Droplet ejection device | One or more bypass flow channels configured to route entrainment carrier gas (e.g., air) that enters from an inlet upstream of an aerosol generation region around aerosol generation region | Pump configured to deposit liquid formulation onto heater element |
| liquid formulation^ | Droplet ejection device and a heater element | Second inlets configured to allow entry of entrainment carrier gas (e.g., air), wherein the second inlets are located between aerosol generation region and an outlet of an airflow channel | Wicking element is in direct contact with liquid formulation |
| liquid formulation^ | Droplet ejection device and a heater element | Second inlets configured to allow entry of entrainment carrier gas (e.g., air), wherein the second inlets are located between aerosol generation region and an outlet of an airflow channel | Pump configured to deposit liquid formulation onto heater element |
| liquid formulation^ | Droplet ejection device and a heater element | One or more bypass flow channels configured to route entrainment carrier gas (e.g., air) that enters from an inlet upstream of an aerosol generation region around aerosol generation region | Wicking element is in direct contact with liquid formulation |
| liquid formulation^ | Droplet ejection device and a heater element | One or more bypass flow channels configured to route entrainment carrier gas (e.g., air) that enters from an inlet upstream of an aerosol generation region around aerosol generation region | Pump configured to deposit liquid formulation onto heater element |
| Solid substrate | Heat conductive substrate coated with agent (e.g., nicotine) | Second inlets configured to allow entry of entrainment carrier gas (e.g., air), wherein the second inlets are located between aerosol generation region and an outlet of an airflow channel | Wicking element is in direct contact with liquid formulation |
| Solid substrate | Heat conductive substrate coated with agent (e.g., nicotine) | Second inlets configured to allow entry of entrainment carrier gas (e.g., air), wherein the second inlets are located between aerosol generation region and an outlet of an airflow channel | Pump configured to deposit liquid formulation onto heater element |
| Solid substrate | Heat conductive substrate coated with agent (e.g., nicotine) | One or more bypass flow channels configured to route entrainment carrier gas (e.g., air) that enters from an inlet upstream of an aerosol generation region around aerosol generation region | Wicking element is in direct contact with liquid formulation |
| Solid substrate | Heat conductive substrate coated with agent (e.g., nicotine) | One or more bypass flow channels configured to route entrainment carrier gas (e.g., air) that enters from an inlet upstream of an aerosol generation region around aerosol generation region | Pump configured to deposit liquid formulation onto heater element |

^Liquid formulation can be housed in reservoir (e.g., collapsible bag).
*The wicking element and wire coil can be made from a single pliable rod.

Other Components

In some cases, an aerosol generating device as provided herein can further comprise one or more indicators. Such indicators can be lights (e.g., light emitting diodes) that can provide indication of one or more aspects of use of the device. An LED indicator can be positioned at an inlet (e.g., distal) end of a passageway as described herein to simulate color changes seen when a conventional cigarette is lit and drawn on by a user. Other indices of operation also are encompassed. For example, visual indicators also can include changes in light color or intensity to show progression of a smoking experience. Tactile indicators and sound indicators similarly are encompassed by the disclosure herein. Moreover, combinations of such indicators can also be used in a single device as provided herein.

II. Adapters

An adapter can be attached to any aerosol generating device (e.g., electronic cigarette) provided herein to permit air to be added to an aerosol generated and emitted by the aerosol generating device (e.g., electronic cigarette) and to generate a flow rate that permits delivery of the aerosol particles to the deep lung of a user. An adapter coupled to an aerosol generating device (e.g., electronic cigarette) can be configured so that it does not significantly change (increase or decrease) the size of aerosol particles generated by the aerosol generating device. In some cases, an adapter is configured to increase or decrease the size of aerosol particles generated by an aerosol generating device.

FIGS. 1A and 1B illustrate an embodiment of an adapter for coupling to an aerosol generating device (e.g., electronic cigarette) for modulating the flow rate of aerosol particles comprising an agent, e.g., nicotine, generated by the aerosol generating device (e.g., electronic cigarette) to facilitate deep lung delivery of the agent to a user of the device. FIG. 1A provides an internal sectional view of an adapter (102a), and FIG. 1B provides an external side view of an adapter (102b). The adapter (102a,b) can comprise a housing, and the housing can comprise a continuous passageway or air-flow channel with a first open end (106a,b), a second open end (110a,b) opposite the first open end, and at least one secondary inlet (108a,b) located in the wall of the housing of the adapter between the first and second open ends. The first open end can function as an outlet (106a,b) while the second open end can function as a primary inlet (110a,b). The primary inlet of the adapter can be configured to couple to an outlet end (e.g., mouthpiece) of an aerosol generating device (e.g., electronic cigarette) (104a,b). The primary and secondary inlets can allow a carrier gas (e.g., air) to enter and flow through the passageway or air-flow channel of the adapter. The at least one secondary inlet (108a,b) can be an opening within the wall of the housing and can allow a carrier gas (e.g., air) to enter the adapter and mix with the contents within the air-flow channel of the adapter. The contents within the air-flow channel can be an aerosol. The aerosol can be a condensation aerosol generated within an aerosol generating device as provided herein following vaporization of a liquid substrate or formulation comprising an agent (e.g., nicotine) by the heater element within an aerosol generation region or vaporization region of the device. The aerosol can be a stable aerosol comprising a stable concentration of aerosol particles such that the carrier gas (e.g., air) that enters through the adapter does not affect aerosol particle size upon mixing with the aerosol particles. The aerosol generating device can be an electronic cigarette or cigar.

An aerosol generating device (e.g., an electronic cigarette) (104a,b) can comprise a reservoir or container for storing an agent (e.g., nicotine), an aerosol generating mechanism (e.g., a heater element), and a control apparatus (e.g., air-flow switch). Upon inhalation by a user through the outlet end of the adapter, the aerosol generating device (e.g., electronic cigarette) (104a,b) can be activated and can generate an aerosol that can flow through the outlet end (e.g., mouthpiece) of the aerosol generating device (e.g., electronic cigarette) (104a,b) and into the second end (primary inlet) of the adapter (110a,b) where a carrier gas (e.g., air) flowing into the adapter through the at least one secondary inlet (108a,b) can entrain the aerosol. Activation of the aerosol generation device can be governed or controlled by a control apparatus as provided herein in the device. In some cases, the control apparatus is an air-flow switch. The air-flow switch can comprise an air flow sensor as provided herein. The air flow switch can further comprise a processor or microprocessor. In some cases, the air-flow switch is in electrical communication with the heater element whereby detection of air flow (e.g., due to inhalation by a user) causes actuation or activation of the heater element. The air-flow that causes the air-flow switch to trigger the heater element can be at a flow rate suitable for generating aerosol particles of an optimal size for deep lung delivery to a user of the device. An aerosol generating mechanism (e.g., heater element) in the aerosol generating device (e.g., electronic cigarette) (104a,b) can be activated at a flow rate suitable for producing aerosol particles that have a diameter of greater than 1 µm. The flow rate can be less than 3 liters per minute (LPM). The flow rate can be less than 1 LPM. The flow rate can be from about 0 to about 0.5 LPM. The flow rate can be about 0.15 LPM or less. The diameter of the aerosol particles can be from about 1 µm to about 5 µm. The diameter of the aerosol particles can be from about 1 µm to about 3 µm. The diameter can be a mass median aerodynamic diameter (MMAD). The diameter can be a volume median diameter (VMD). The entraining of the aerosol with the carrier gas (e.g., air) can produce a total flow rate of about 6 LPM to about 40 LPM exiting the outlet of the adapter coupled to the aerosol generating device (e.g., electronic cigarette) at a low enough flow resistance to allow direct to lung inhalation without the need for the user to perform a mouth breathing maneuver. The user can be a smoker. In some cases, an adapter as provided herein is an integral, non-removable piece of an aerosol generating device as provided herein. An aerosol generating device comprising a non-removable adapter can be a device as depicted in FIG. 2, and the portion of the aerosol generating device in FIG. 2 comprising the second air inlets (204), the mouthpiece (202), and the outlet (216) can be an adapter similar to that shown in FIGS. 1A and 1B coupled to the end of an aerosol generating device (e.g., electronic cigarette) as provided herein. In some cases, an adapter as provided herein is removable or replaceable, and a user of an aerosol generating device as provided herein can attach or couple the adapter to the device prior to using the device. The user can add the adapter before a use session or between uses (e.g., puffs) of the device. In some cases, a user of an aerosol generating device as provided herein is capable of modulating an inhalation resistance of the device by coupling an adapter as provided herein to the device. In this manner, a user of a device as provided herein can alter his or her smoking experience through the use of an adapter as shown in FIGS. 1A and 1B to an aerosol generating device (e.g., electronic cigarette).

An adapter can be attached to an aerosol generating device, e.g., electronic cigarette, to add air to an aerosol generated and emitted by the device and to generate a flow rate that permits delivery of the aerosol particles to the deep lung of a subject. An adapter coupled to an electronic cigarette can be configured so that it does not significantly change (increase or decrease) the size of aerosol particles generated by the electronic cigarette. The adapter can allow entry of carrier gas (e.g., air) that has a substantially laminar flow with respect to the flow of aerosol particles through the aerosol generating device after the aerosol particles have reached a stable number concentration. The aerosol particles can be carried through an outlet of the device. In some cases, an adapter is configured to increase or decrease the size of aerosol particles generated by an electronic cigarette. The adapter can allow entry of carrier gas (e.g., air) that has a substantially perpendicular or transverse flow with respect to the aerosol particles flowing through the aerosol generating device prior to the aerosol particles having reached a stable number concentration. The adapter can contribute to the formation of the aerosol particles prior to exit from an outlet of the device.

An outlet end of the aerosol generating device (e.g., electronic cigarette) can comprise a mouthpiece. In some cases, an adapter replaces or substitutes for the mouthpiece of the aerosol generating device (e.g., electronic cigarette). In some cases, the adapter couples to a mouthpiece on an aerosol generating device (e.g., electronic cigarette).

In some cases, an aerosol generating device is not an electronic cigarette.

An adapter can be made of copper, carbon, nickel, iron, chromium, graphite, tantalum, stainless steel, gold, platinum, tungsten molybdenum alloy, metal ceramic matrices, and metal alloys, such as chromium alloys, nickel alloys, aluminum alloys, iron alloys, plastics, wood, all metals, nonmetal or combination thereof. In some cases, an adapter is made of at least 1, 2, 3, 4, 5, 6, 7, 8, 9 or 10 materials.

In some cases, an adapter comprises about, more than, less than, or at least 1, 2, 3, 4, 5, 6, 7, 8, 9, or 10, pieces coupled or affixed together. In some cases, an adapter is a single integral unit.

Adapter Channel

An adapter can comprise a channel (e.g., hollow main body). In some cases, an adapter comprises one channel. In some cases, an adapter comprises more than one channel; e.g., 2, 3, 4, 5, 6, 7, 8, 9, or 10 channels. In some cases, the multiple channels are separated from each other within the adapter.

Adapter Channel Dimensions

An external diameter of an adapter channel can be about, more than, less than, at least, or at most 0.1, 0.15, 0.2, 0.25, 0.3, 0.35. 0.4, 0.45, 0.5, 0.55, 0.6, 0.65, 0.7, 0.75, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, or 6.5 cm. An external diameter of an adapter channel can be about 0.10 to about 0.2 cm, about 0.2 to about 0.3 cm, about 0.3 to about 0.4 cm, about 0.4 to about 0.5 cm, about 0.5 to about 0.6 cm, about 0.6 to about 0.7 cm, about 0.7 to about 0.8 cm, about 0.8 to about 0.9 cm, about 0.7 to about 1 cm, about 0.8 to about 1 cm, about 0.9 to about 1 cm, about 0.9 to about 1.1 cm, about 1 to about 1.25 cm, about 1.25 to about 1.5 cm, about 1.5 to about 2 cm, or about 2 cm to about 2.5 cm. In some cases, an adapter comprises an internal diameter of 0.45 inches and an exterior diameter of 0.5 inches.

An internal diameter of an adapter channel can be about, more than, less than, at least or at most 0.1, 0.15, 0.2, 0.25, 0.3, 0.35. 0.4, 0.45, 0.5, 0.55, 0.6, 0.65, 0.7, 0.75, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.1, 1.143, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, or 6.5 cm. An internal diameter of an adapter channel can be about 0.10 to about 0.2 cm, about 0.2 to about 0.3 cm, about 0.3 to about 0.4 cm, about 0.4 to about 0.5 cm, about 0.5 to about 0.6 cm, about 0.6 to about 0.7 cm, about 0.7 to about 0.8 cm, about 0.8 to about 0.9 cm, about 0.7 to about 1 cm, about 0.8 to about 1 cm, about 0.9 to about 1 cm, about 0.9 to about 1.1 cm, about 1 to about 1.25 cm, about 1.25 to about 1.5 cm, about 1.5 to about 2 cm, or about 2 cm to about 2.5 cm.

A length of an adapter, or adapter channel, can be about, more than, less than, at least or at most 1, 1.5, 2, 2.5, 3, 3.5, 4, 4.5, 5, 5.5, 6, 6.5, 7, 7.5, 8, 8.5, 9, 9.5, or 10 cm. An adapter, or adapter channel, can have a length of about 1 to about 10 cm, about 2 to about 10 cm, about 2 to about 9 cm, about 2 to about 8 cm, about 2 to about 7 cm, about 2 to about 7 cm, about 2 to about 6 cm, about 2 to about 5 cm, about 2 to about 4 cm, about 3 to about 10 cm, about 3 to about 9 cm, about 3 to about 8 cm, about 3 to about 7 cm, about 3 to about 6 cm, about 3 to about 5 cm, about 4 to about 10 cm, about 4 to about 9 cm, about 4 to about 8 cm, about 4 to about 7 cm, about 4 to about 6 cm, or about 4 to about 5 cm. In some cases, the adapter or adapter channel is about 6 cm in length.

An area of a transverse section of an adapter channel can be the same or substantially the same along the length of the channel. In some cases, an area in transverse section at the primary inlet is the same, larger, or smaller relative to an area in transverse section at the outlet. In some cases, the area in traverse section of an adapter channel at the primary inlet is substantially the same, larger, or smaller than the area in transverse section of a mouthpiece of an electronic delivery device, e.g., electronic cigarette. The channel can have the same area in transverse section at the primary inlet end and the outlet end of the adapter.

The area in transverse section of an adapter channel can vary along the length of the channel. The channel can continuously decrease in transverse sectional area from the primary inlet to the outlet. The channel can continuously increase in transverse sectional area from the primary inlet to the outlet. The channel can continuously decrease in transverse sectional area from the primary inlet to a point between the primary inlet end and the outlet, and then vary in area in transverse section from the point to the outlet. The area in transverse section can be the same from the point until the outlet or can continuously increase to the same, larger, or smaller transverse sectional area as the outlet end. The channel can continuously increase in transverse sectional area from the primary inlet to a point between the primary inlet end and the outlet, and then vary in area in transverse section from the point to the outlet end. The area in transverse section can be the same from the point until the outlet end or can continuously decrease to the same, larger, or smaller transverse sectional area as the outlet end.

An adapter channel can have a straight, curved, helical, or spiral path. A adapter channel at any distance between the primary inlet and the outlet end can be in the shape of a curve, circle, parabola, hyperbola, polygon, concave polygon, constructible polygon, convex polygon, cyclic polygon, decagon, digon, dodecagon, nonagon, equiangular polygon, equilateral polygonhenagon, hendecagon, heptagon, hexadecagon, hexagon, Lemoine hexagon, icosagon, octagon, pentagon, regular polygon, regular decagon, regular octagon, regular pentagon, star without crossing lines, star polygon, decagram, octagram, heptagram, hexagram, pentagram, triangle, acute triangle, anticomplementary triangle, equilateral triangle, excentral triangle, isosceles triangle, medial triangle, obtuse triangle, rational triangle, right triangle, 30-60-90 triangle, isosceles right triangle, Kepler triangle, scalene triangle, reuleaux triangle, penrose tile, trapezium, isosceles trapezium, undecagon, quadrilateral, cyclic quadrilateral, tetrachord, kite, parallelogram, equilateral parallelogram, rhombus, Lozenge, rhomboid, rectangle, regular quadrilateral, square, rhombus, tangential quadrilateral, trapezoid, isosceles trapezoid, polydrafter, balbis, annulus, arbelos, disc, Archimedes' twin circles, Bankoff circle, circumcircle, excircle, incircle, nine-point circle, circular sector, circular segment, crescent, ellipse, various lemniscates, lune, oval, Reuleaux polygon, rotor, lens, vesica piscis, Reuleaux triangle, salinon, semicircle, sphere, gomboc, tomoe, magatama, triquetra, Yin-Yang, Archimedean spiral, astroid, deltoid, ellipse, super ellipse, tomahawk or any geometric shape or combination thereof. Different geometries and dimensions can be used that are configured, or sized, to allow for the appropriate ratio of flow rates between that flowing through an electronic delivery device, e.g., electronic cigarette and that flowing into the adapter.

Primary Inlet

A primary inlet end of an adapter can connect, couple, or attach to an outlet end of an aerosol generating device (e.g., electronic cigarette). The outlet end can be a mouthpiece.

In some cases, an adapter can be shaped to substantially couple, attach, connect, abut, or conform to the cross sectional size and shape of an outlet end of an aerosol generating device, e.g., electronic cigarette. In some cases, an adapter is shaped to substantially couple, attach, connect, abut, or conform to the cross sectional size and shape of a mouthpiece of an electronic cigarette. In some cases, an adapter is shaped to substantially couple, attach, connect, abut, or conform to the cross sectional size and shape of an end of an aerosol generating device (e.g., electronic cigarette) from which an aerosol generated by the aerosol generating device (e.g., electronic cigarette) is released from the aerosol generating device (e.g., electronic cigarette). In some cases, an adapter is shaped to substantially couple, attach, connect, abut, or conform to the cross sectional size and shape of an outlet end of an aerosol generating device (e.g., electronic cigarette), wherein the adapter replaces or substitutes for a mouthpiece of the aerosol generating device (e.g., electronic cigarette).

In some cases, an inlet end of an adapter is threaded. In some cases, an adapter can be connected to an outlet end of an aerosol generating device, e.g., electronic cigarette, by screwing, fastening, clamping, tethering, friction coupling, suction coupling, crimping, welding, soldering, brazing, taping, gluing, cementing or any combination thereof. In some cases, the adapter can be connected to an outlet end of an aerosol generating device, e.g., electronic cigarette, by use of an adhesive, magnet, vacuum, frictional force, physical force or combinations thereof.

The primary inlet end of an adapter can have an opening with any shape, e.g., circle, polygon, polygon, constructible polygon, convex polygon, cyclic polygon, decagon, digon, dodecagon, nonagon, equiangular polygon, equilateral polygonhenagon, hendecagon, heptagon, hexadecagon, hexagon, Lemoine hexagon, icosagon, octagon, pentagon, regular polygon, regular decagon, regular octagon, regular pentagon, star without crossing lines, star polygon, decagram, octagram, heptagram, hexagram, pentagram, triangle, acute triangle, anticomplementary triangle, equilateral triangle, excentral triangle, isosceles triangle, medial triangle, obtuse triangle, rational triangle, right triangle, 30-60-90 triangle, isosceles right triangle, Kepler triangle, scalene triangle, reuleaux triangle, penrose tile, trapezium, isosceles trapezium, undecagon, quadrilateral, cyclic quadrilateral, tetrachord, kite, parallelogram, equilateral parallelogram, rhombus, Lozenge, rhomboid, rectangle, regular quadrilateral, square, rhombus, tangential quadrilateral, trapezoid, isosceles trapezoid, polydrafter, balbis, annulus, arbelos, disc, Archimedes' twin circles, Bankoff circle, circumcircle, excircle, incircle, nine-point circle, circular sector, circular segment, crescent, ellipse, various lemniscates, lune, oval, Reuleaux polygon, rotor, lens, vesica piscis, Reuleaux triangle, salinon, semicircle, sphere, gomboc, tomoe, magatama, triquetra, Yin-Yang, Archimedean spiral, astroid, deltoid, ellipse, super ellipse, tomahawk or any geometric shape or combination thereof. The primary inlet end of an adapter can have the same shape as that of an aerosol generating device, e.g., electronic cigarette. The primary inlet end of an adapter can have the same shape as a mouthpiece end of an aerosol generating device (e.g., electronic cigarette). The shape of the primary inlet end of an adapter can be configured to permit coupling to an aerosol generating device, e.g., electronic cigarette. The shape and dimensions of the primary inlet end of an adapter can be configured to permit coupling of the primary inlet end of the adapter to the mouthpiece end of an aerosol generating device, e.g., electronic cigarette.

Adapter Outlet

An outlet end of an adapter can serve as the end of the adapter through which a user inhales. The outlet of the adapter can be a mouthpiece, or can be further coupled to a mouthpiece. The outlet end of an aerosol generating device, e.g., electronic cigarette can be an end of an electronic cigarette from which an aerosol generated by the aerosol generating device, e.g., electronic cigarette is released from the aerosol generating device, e.g., electronic cigarette.

The outlet end of an adapter can have an opening with any shape, e.g., circle, polygon, polygon, constructible polygon, convex polygon, cyclic polygon, decagon, digon, dodecagon, nonagon, equiangular polygon, equilateral polygonhenagon, hendecagon, heptagon, hexadecagon, hexagon, Lemoine hexagon, icosagon, octagon, pentagon, regular polygon, regular decagon, regular octagon, regular pentagon, star without crossing lines, star polygon, decagram, octagram, heptagram, hexagram, pentagram, triangle, acute triangle, anticomplementary triangle, equilateral triangle, excentral triangle, isosceles triangle, medial triangle, obtuse triangle, rational triangle, right triangle, 30-60-90 triangle, isosceles right triangle, Kepler triangle, scalene triangle, reuleaux triangle, penrose tile, trapezium, isosceles trapezium, undecagon, quadrilateral, cyclic quadrilateral, tetrachord, kite, parallelogram, equilateral parallelogram, rhombus, Lozenge, rhomboid, rectangle, regular quadrilateral, square, rhombus, tangential quadrilateral, trapezoid, isosceles trapezoid, polydrafter, balbis, annulus, arbelos, disc, Archimedes' twin circles, Bankoff circle, circumcircle, excircle, incircle, nine-point circle, circular sector, circular segment, crescent, ellipse, various lemniscates, lune, oval, Reuleaux polygon, rotor, lens, vesica piscis, Reuleaux triangle, salinon, semicircle, sphere, gomboc, tomoe, magatama, triquetra, Yin-Yang, Archimedean spiral, astroid, deltoid, ellipse, super ellipse, tomahawk or any geometric shape or combination thereof.

The shape of the outlet end of an adapter can be configured to permit inhalation by a user as provided herein.

Orifices in an Adapter Outlet

An orifice in the outlet end can be located at the periphery of the outlet end. In some cases, the outlet end can comprise one orifice. In some cases, the outlet end can comprise at least one orifice. The outlet end can comprise a plurality of orifices. The orifices can be of substantially the same size. The orifices can be of varying transverse sectional area and which can be located at the periphery of the outlet, about the longitudinal axis of the outlet in any random or symmetrical pattern. An outlet end can have about, more than, less than, or at least 1, 2, 3, 4, 5, 6, 7, 8, 9, 10, 11, 12, 13, 14, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 orifices.

Orifices at the outlet end of an adapter can be arranged in symmetrical, mirror symmetrical, rotational symmetrical, fivefold symmetrical, six fold symmetrical, crystal symmetrical, fractal, spirals, meanders, flow, chaos, waves, dunes, bubbles, foams, tilings, cracks, spots, stripes, tiling or any additional pattern or combination thereof.

An orifice can be in the shape of a circle, polygon, polygon, constructible polygon, convex polygon, cyclic polygon, decagon, digon, dodecagon, nonagon, equiangular polygon, equilateral polygonhenagon, hendecagon, heptagon, hexadecagon, hexagon, Lemoine hexagon, icosagon, octagon, pentagon, regular polygon, regular decagon, regular octagon, regular pentagon, star without crossing lines, star polygon, decagram, octagram, heptagram, hexagram, pentagram, triangle, acute triangle, anticomplementary triangle, equilateral triangle, excentral triangle, isosceles triangle, medial triangle, obtuse triangle, rational triangle, right triangle, 30-60-90 triangle, isosceles right triangle, Kepler triangle, scalene triangle, reuleaux triangle, penrose tile, trapezium, isosceles trapezium, undecagon, quadrilateral, cyclic quadrilateral, tetrachord, kite, parallelogram, equilateral parallelogram, rhombus, Lozenge, rhomboid, rectangle, regular quadrilateral, square, rhombus, tangential quadrilateral, trapezoid, isosceles trapezoid, polydrafter, balbis, annulus, arbelos, disc, Archimedes' twin circles, Bankoff circle, circumcircle, excircle, incircle, nine-point circle, circular sector, circular segment, crescent, ellipse, various lemniscates, lune, oval, Reuleaux polygon, rotor, lens, vesica piscis, Reuleaux triangle, salinon, semicircle, sphere, gomboc, tomoe, magatama, triquetra, Yin-Yang, Archimedean spiral, astroid, deltoid, ellipse, super ellipse, tomahawk or any geometric shape or combination thereof.

An orifice in the outlet can have a diameter that can be about, more than, less than, at least or at most 0.1, 0.15, 0.2, 0.25, 0.3, 0.35. 0.4, 0.45, 0.5, 0.55, 0.6, 0.65, 0.7, 0.75, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, or 6.5 cm. An outlet diameter can be about 0.10 to about 0.2 cm, about 0.2 to about 0.3 cm, about 0.3 to about 0.4 cm, about 0.4 to about 0.5 cm, about 0.5 to about 0.6 cm, about 0.6 to about 0.7 cm, about 0.7 to about 0.8 cm, about 0.8 to about 0.9 cm, about 0.7 to about 1 cm, about 0.8 to about 1 cm, about 0.9 to about 1 cm, about 0.9 to about 1.1 cm, about 1 to about 1.25 cm, about 1.25 to about 1.5 cm, about 1.5 to about 2 cm, or about 2 cm to about 2.5 cm.

Secondary Air Inlets

The adapter can comprise one or more secondary inlets in a wall of a channel between an outlet end and primary inlet end of the adapter. The one or more secondary inlets can modulate air entry into the adapter which can result in an increase or decrease in flow rate of an aerosol exiting the adapter.

An adapter can comprise about, more than, less than, or at least 1, 2, 3, 4, 5, 6, 7, 8, 9, 10, 11, 12, 13, 14, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 330, 331, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 660, 661, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 725, 750, 775, 800, 825, 850, 875, 900, 925, 950, 975, or 1000 secondary air inlets. An adapter can comprise about 1 to about 9, about 1 to about 8, about 1 to about 7, about 1 to about 6, about 1 to about 5, about 1 to about 4, about 2 to about 8, about 2 to about 7, about 2 to about 6, about 2 to about 5, about 3 to about 8, about 3 to about 7, about 3 to about 6, about 4 to about 8, about 4 to about 7, about 4 to about 6, about 1 to about 10, about 5 to about 15, about 10 to about 20, about 15 to about 25, about 20 to about 30, about 25 to about 35, about 30 to about 40, about 35 to about 45, about 40 to about 50, about 45 to about 55, about 50 to about 60, about 55 to about 65, about 60 to about 70, about 65 to about 75, about 70 to about 80, about 75 to about 85, about 80 to about 90, about 85 to about 95, or about 90 to about 100 secondary air inlets.

A secondary inlet can be any distance between the outlet end and the primary inlet end of the adapter. In some cases, one or more secondary inlets are proximal to the primary inlet of an adapter. In some cases, one or more secondary inlets are proximal to the outlet end of an adapter. In some cases, one or more secondary inlets are equidistant from the primary inlet and the outlet end.

The one or more secondary inlets can have the shape of a curve, circle, parabola, hyperbola, polygon, concave polygon, constructible polygon, convex polygon, cyclic polygon, decagon, digon, dodecagon, nonagon, equiangular polygon, equilateral polygonhenagon, hendecagon, heptagon, hexadecagon, hexagon, Lemoine hexagon, icosagon, octagon, pentagon, regular polygon, regular decagon, regular octagon, regular pentagon, star without crossing lines, star polygon, decagram, octagram, heptagram, hexagram, pentagram, triangle, acute triangle, anticomplementary triangle, equilateral triangle, excentral triangle, isosceles triangle, medial triangle, obtuse triangle, rational triangle, right triangle, 30-60-90 triangle, isosceles right triangle, Kepler triangle, scalene triangle, reuleaux triangle, penrose tile, trapezium, isosceles trapezium, undecagon, quadrilateral, cyclic quadrilateral, tetrachord, kite, parallelogram, equilateral parallelogram, rhombus, Lozenge, rhomboid, rectangle, regular quadrilateral, square, rhombus, tangential quadrilateral, trapezoid, isosceles trapezoid, polydrafter, balbis, annulus, arbelos, disc, Archimedes' twin circles, Bankoff circle, circumcircle, excircle, incircle, nine-point circle, circular sector, circular segment, crescent, ellipse, various lemniscates, lune, oval, Reuleaux polygon, rotor, lens, vesica piscis, Reuleaux triangle, salinon, semicircle, sphere, gomboc, tomoe, magatama, triquetra, Yin-Yang, Archimedean spiral, astroid, deltoid, ellipse, super ellipse, tomahawk or any geometric shape or combination thereof.

Secondary inlets on an adapter can be of uniform or non-uniform size. Secondary inlets can be arranged in a random or structured pattern. One or more secondary inlets on an adapter can be arranged in symmetrical, mirror symmetrical, rotational symmetrical, fivefold symmetrical, six fold symmetrical, crystal symmetrical, fractal, spirals, meanders, flow, chaos, waves, dunes, bubbles, foams, tilings, cracks, spots, stripes, tiling or any additional pattern or combination thereof. In some cases, the secondary inlets are in a row.

In some cases, one or more secondary air inlets comprise a surface of semi-porous or semi-permeable material such as a filter, filter paper, screen or mesh. The filter can be a 0.2 µm filter, 0.45 µm filter, 0.7 µm filter, 1.0 µm filter, 1.2 µm filter, 1.6 µm filter, or 2.7 µm filter. The filter can comprise glass microfiber, cellulose acetate, polyvinylidene difluoride (PVDF), polyethersulfone (PES), Whatman® glass microfiber filter (grade GF/A, GF/B, GF/C, GF/D, GF/F), Whatman™ 934-AH™ glass microfiber filter. The semi-porous material can comprise metal, fiber, flexible material, or ductile material. In some cases, the mesh comprises plastic. In some cases, the plastic mesh is extruded, expanded, tubular, or oriented. Plastic can be, e.g., polypropylene, polyethylene, nylon, polyvinyl chloride (PVC), or polytetrafluoroethylene (PTFE). In some cases, the mesh comprises metal. Metal mesh can be photochemically etched or electroformed (screen filter), knitted, welded, expanded, or woven from steel or other metals. In some cases, the mesh comprises fiberglass.

The one or more secondary inlets can have a length of about, more than, less than, or at least 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.62, 7.75, 8, 8.25, 8.5, 8.75, 9, 9.25, 9.5, 9.75, 10, 10.25, 10.5, 10.75, 11, 11.25, 11.5, 11.75, 12, 12.25, 12.5, 12.75, 13, 13.5, 14, 14.5, 15, 15.5, 16, 16.5, 17, 17.5, 18, 18.5, 19, 19.5, 20, 21, 22, 23, 24, or 25 mm. The one or more secondary inlets have a length of about 0.10 to about 0.2 cm, about 0.2 to about 0.3 cm, about 0.3 to about 0.4 cm, about 0.4 to about 0.5 cm, about 0.5 to about 0.6 cm, about 0.6 to about 0.7 cm, about 0.7 to about 0.8 cm, about 0.8 to about 0.9 cm, about 0.7 to about 1 cm, about 0.8 to about 1 cm, about 0.9 to about 1 cm, about 0.9 to about 1.1 cm, about 1 to about 1.25 cm, about 1.25 to about 1.5 cm, about 1.5 to about 2 cm, or about 2 cm to about 2.5 cm.

The one or more secondary inlets can have a width of about, more than, less than, or at least 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.62, 7.75, 8, 8.25, 8.5, 8.75, 9, 9.25, 9.5, 9.75, 10, 10.25, 10.5, 10.75, 11, 11.25, 11.5, 11.75, 12, 12.25, 12.5, 12.75, 13, 13.5, 14, 14.5, 15, 15.5, 16, 16.5, 17, 17.5, 18, 18.5, 19, 19.5, 20, 21, 22, 23, 24, or 25 mm. The one or more secondary inlets have a width of about 0.05 to about 0.1 cm, about 0.10 to about 0.2 cm, about 0.2 to about 0.3 cm, about 0.3 to about 0.4 cm, about 0.4 to about 0.5 cm, about 0.5 to about 0.6 cm, about 0.6 to about 0.7 cm, about 0.7 to about 0.8 cm, about 0.8 to about 0.9 cm, about 0.7 to about 1 cm, about 0.8 to about 1 cm, about 0.9 to about 1 cm, about 0.9 to about 1.1 cm, about 1 to about 1.25 cm, about 1.25 to about 1.5 cm, about 1.5 to about 2 cm, or about 2 cm to about 2.5 cm.

When a secondary inlet is a circle, the circle can have a diameter of about, more than, less than, or at least 0.1, 0.15, 0.2, 0.25, 0.3, 0.35. 0.4, 0.45, 0.5, 0.55, 0.6, 0.65, 0.7, 0.75, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.1, 1.2, 1.3, 1.4, 1.5, 1.6, 1.7, 1.8, 1.9, or 2 cm.

An external opening of one or more secondary inlets can be at a surface of an outer wall of an adapter. In some cases, an external opening of one or more secondary inlets can be raised above a surface of an outer wall of an adapter by about, more than, less than, at least, or at most 0.1, 0.15, 0.2, 0.21, 0.22, 0.23, 0.24, 0.25, 0.26, 0.27, 0.28, 0.29, 0.3, 0.35, 0.4, 0.45, or 0.5 cm. An external opening of the one or more secondary inlets can be raised above a surface of an outer wall of an adapter by about 0.1 to about 0.2 cm, about 0.2 to about 0.25 cm, about 0.25 to about 0.3 cm, about 0.3 to about 0.35 cm, about 0.35 to about 0.4 cm, about 0.4 to about 0.45 cm, or about 0.45 to about 0.5 cm, or about 0.1 to about 0.5 cm.

An exterior opening of one or more secondary inlets can be recessed into an outer wall of an adapter by about, more than, less than, at least, or at most 0.05, 0.075, 0.1, 0.15, 0.175, 0.2, 0.21, 0.22, 0.23, 0.24, 0.25, 0.26, 0.27, 0.28, 0.29, 0.3, 0.35, 0.4, 0.45, or 0.5 cm. An exterior opening of one or more secondary inlets can be recessed into an outer wall of an adapter by about 0.1 to about 0.2 cm, about 0.2 to about 0.25 cm, about 0.25 to about 0.3 cm, about 0.3 to about 0.35 cm, about 0.35 to about 0.4 cm, about 0.4 to about 0.45 cm, about 0.45 to about 0.5 cm, or about 0.1 to about 0.5 cm.

An interior opening of one or more secondary inlets can be at a surface of an inner wall of an adapter. In some cases, an interior opening of one or more secondary inlets can be raised above a surface of an inner wall of an adapter (protrude into the adapter) by about, more than, less than, at least, or at most 0.1, 0.15, 0.2, 0.21, 0.22, 0.23, 0.24, 0.25, 0.26, 0.27, 0.28, 0.29, 0.3, 0.35, 0.4, 0.45, or 0.5 cm. An interior opening of one or more secondary inlets can be raised above a surface of an inner wall of an adapter (protrude into the adapter) by about 0.1 to about 0.2 cm, about 0.2 to about 0.25 cm, about 0.25 to about 0.3 cm, about 0.3 to about 0.35 cm, about 0.35 to about 0.4 cm, about 0.4 to about 0.45 cm, or about 0.45 to about 0.5 cm, or about 0.1 to about 0.5 cm.

An interior opening of one or more secondary inlets can be recessed into an inner wall of an adapter by exactly, about, more than, less than, at least or at most 0.05, 0.075, 0.1, 0.15, 0.175, 0.2, 0.21, 0.22, 0.23, 0.24, 0.25, 0.26, 0.27, 0.28, 0.29, 0.3, 0.35, 0.4, 0.45, or 0.5 cm. An interior opening of one or more secondary inlets can be recessed into an inner wall of an adapter by about 0.1 to about 0.2 cm, about 0.2 to about 0.25 cm, about 0.25 to about 0.3 cm, about 0.3 to about 0.35 cm, about 0.35 to about 0.4 cm, about 0.4 to about 0.45 cm, about 0.45 to about 0.5 cm, or about 0.1 to about 0.5 cm.

Positioning of the one or more secondary inlets on the adapter can be varied in order to control the performance characteristics of the adapter.

One or more secondary inlets can be separated along a main axis of the adapter by about, more than, less than, at least or at most 0.1, 0.15, 0.2, 0.21, 0.22, 0.23, 0.24, 0.25, 0.26, 0.27, 0.28, 0.29, 0.3, 0.35, 0.4, 0.45, 0.5, 0.6, 0.7, 0.8, 0.9, 1, 1.5, 2, 2.5, or 3 cm. In some cases, one or more secondary inlets are separated in any direction on a surface of an adapter by about, more than, less than, at least, or at most 0.1, 0.15, 0.2, 0.21, 0.22, 0.23, 0.24, 0.25, 0.26, 0.27, 0.28, 0.29, 0.3, 0.35, 0.4, 0.45, 0.5, 0.6, 0.7, 0.8, 0.9, 1, 2, or 3 cm.

Filters

In some cases, an adapter comprises one or more filters. An adapter can have about, more than, less than, or at least 0, 1, 2, 3, 4, 5, 6, 7, 8, 9, or 10 filters. A filter medium can be composed of any known filtering medium or combination thereof including cellulose acetate, and cotton. A filter can be placed at any distance between a primary inlet end and an outlet of an adapter.

In some cases, an adapter comprises a surface of semi-porous or semi-permeable material such as a filter, filter paper, screen or mesh between a primary inlet end and outlet of an adapter. The filter can be a 0.2 μm filter, 0.45 μm, 0.7 μm filter, 1.0 μm filter, 1.2 μm filter, 1.6 μm filter, or 2.7 μm filter. The filter can comprise glass microfiber, cellulose acetate, polyvinylidene difluoride (PVDF), polyethersulfone (PES), Whatman® glass microfiber filter (grade GF/A, GF/B, GF/C, GF/D, GF/F), Whatman™ 934-AH™ glass microfiber filter. The semi-porous material can comprise metal, fiber, flexible material, or ductile material. In some cases, the mesh comprises plastic. In some cases, the plastic mesh is extruded, expanded, tubular, or oriented. Plastic can comprise, e.g., polypropylene, polyethylene, nylon, polyvinyl chloride (PVC), or polytetrafluoroethylene (PTFE). In some cases, the mesh comprises metal. Metal mesh can be photochemically etched or electroformed (screen filter), knitted, welded, expanded, or woven from steel or other metals. In some cases, the mesh comprises fiberglass.

Flow Properties

An adapter can be configured to generate an interior air resistance (to inhalation) when coupled to an electronic delivery device, e.g., electronic cigarette, no greater than an inhalation resistance of a cigarette. The interior air resistance (to inhalation) can also be referred to as the inhalation resistance, resistance to draw, draft resistance, draw resistance, puff resistance or puffability. When coupled to an aerosol generating device (e.g., electronic cigarette) as provided herein, an adapter can be configured to generate an inhalation resistance with an associated vacuum of about, more than, less than, or at least 0.1, 0.2, 0.3, 0.4, 0.5, 0.6, 0.7, 0.8, 0.9, 1, 1.5, 2, 2.5, 2.54, 3, 3.5, 4, 4.5, 5, 5.5, 6, 6.5, 7, 7.5, 8, 8.5, 9, 9.5, 10, 10.5, 11, 11.5, or 12 inches of water at a flow rate of about, more than, less than, or at least 0.1, 0.5, 1, 5, 10, 15, 20, 25, 30, 35, 40, 45, 50, 55, 60, 65, 70, 75, or 80 liters per minute. When coupled to an aerosol generating device (e.g., electronic cigarette) as provided herein, an adapter can be configured to generate an inhalation resistance with an associated vacuum of about 0.1 to about 1 inches of water, about 1 to about 1.5 inches of water, about 1.5 to about 2 inches of water, about 2 to about 2.5 inches of water, about 2.5 to about 3 inches of water, about 3 to about 3.5 inches of water, about 3.5 to about 4 inches of water, about 4 to about 4.5 inches of water, about 4.5 to about 5 inches of water, about 5 to about 5.5 inches of water, about 5.5 to about 6 inches of water, about 6 to about 6.5 inches of water, about 6.5 to about 7 inches of water, about 7 to about 7.5 inches of water, about 7.5 to about 8 inches of water, about 8 to about 8.5 inches of water, about 8.5 to about 9 inches of water, about 9 to about 9.5 inches of water, about 9.5 to about 10 inches of water, about 10 to about 10.5 inches of water, about 10.5 to about 11 inches of water, about 11 to about 11.5 inches of water, about 11.5 to about 12 inches of water, about 0.25 to about 5 inches of water, about 1 to about 5 inches of water, or about 0.5 to about 4 inches of water at a flow rate of about, more than, less than, or at least 0.1, 0.5, 1, 5, 10, 15, 20, 25, 30, 35, 40, 45, 50, 55, 60, 65, 70, 75, or 80 liters per minute. When coupled to an aerosol generating device (e.g., electronic cigarette) as provided herein, an adapter can be configured to generate an inhalation resistance with an associated vacuum of about 1 to about 5 inches of water, about 5 to about 10 inches of water, about 1 to about 2 inches of water, about 1 to about 4 inches of water, about 1 to about 6 inches of water, about 1 to about 8 inches of water, about 1 to about 10 inches of water, or about 1 to about 12 inches of water at a flow rate of about, more than, less than, or at least 1, 5, 10, 15, 20, 25, 30, 35, 40, 45, 50, 55, 60, 65, 70, 75, or 80 liters per minute. When coupled to an aerosol generating device (e.g., electronic cigarette) as provided herein, an adapter can be configured to generate an inhalation resistance with an associated vacuum of about, more than, less than, or at least 0.254, 0.508, 0.762, 1.016, 1.27, 1.524, 1.778, 2.032, 2.286, 2.54, 3.81, 5.08, 6.35, 7.62, 8.89, 10.16, 11.43, 12.7, 13.97, 15.24, 16.51, 17.78, 19.05, 20.32, 21.59, 22.86, 24.13, 25.4, 26.67, 27.94, 29.21, or 30.48 cm of water at a flow rate of about, more than, less than, or at least 0.1, 0.5, 1, 5, 10, 15, 20, 25, 30, 35, 40, 45, 50, 55, 60, 65, 70, 75, or 80 liters per minute. When coupled to an aerosol generating device (e.g., electronic cigarette) as provided herein, an adapter can be configured to generate an inhalation resistance with an associated vacuum of about 0.254 to about 2.54 cm of water, about 2.54 to about 3.81 cm of water, about 3.81 to about 5.08 cm of water, about 5.08 to about 6.35 cm of water, about 6.35 to about 7.62 cm of water, about 7.62 to about 8.89 cm of water, about 8.89 to about 10.16 cm of water, about 10.16 to about 11.43 cm of water, about 11.43 to about 12.7 cm of water, about 12.7 to about 13.97 cm of water, about 13.97 to about 15.24 cm of water, about 15.24 to about 16.51 cm of water, about 16.51 to about 17.78 cm of water, about 17.78 to about 19.05 cm of water, about 19.05 to about 20.32 cm of water, about 20.32 to about 21.59 cm of water, about 21.59 to about 22.86 cm of water, about 22.86 to about 24.13 cm of water, about 24.13 to about 25.4 cm of water, about 25.4 to about 26.67 cm of water, about 26.67 to about 27.94 cm of water, about 27.94 to about 29.21 cm of water, about 29.21 to about 30.48 cm of water, about 0.635 to about 12.7 cm of water, about 2.54 to about 12.7 cm of water, or about 1.27 to about 10.16 cm of water at a flow rate of about, more than, less than, or at least 0.1, 0.5, 1, 5, 10, 15, 20, 25, 30, 35, 40, 45, 50, 55, 60, 65, 70, 75, or 80 liters per minute. When coupled to an aerosol generating device (e.g., electronic cigarette) as provided herein, an adapter can be configured to generate an inhalation resistance with an associated vacuum of about 2.54 to about 12.7 cm of water, about 12.7 to about 25.4 cm of water, about 2.54 to about 5.08 cm of water, about 2.54 to about 10.16 cm of water, about 2.54 to about 15.24 cm of water, about 2.54 to about 20.32 cm of water, about 2.54 to about 25.4 cm of water, or about 2.54 to about 30.48 cm of water at a flow rate of about, more than, less than, or at least 1, 5, 10, 15, 20, 25, 30, 35, 40, 45, 50, 55, 60, 65, 70, 75, or 80 liters per minute. Expressed differently, when coupled to an aerosol generating device (e.g., electronic cigarette) as provided herein, an adapter can be configured to generate an inhalation resistance no greater than 0.08 $(cm\ H_2O)^{1/2}/LPM$. When coupled to an aerosol generating device (e.g., electronic cigarette) as provided herein, an adapter can be configured to generate an inhalation resistance of about, more than, less than, or at least 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.25, 0.3, 0.4, 0.5, 0.6, 0.7, 0.8, 0.9, 1, 1.5, 2, or 2.5 $(cm\ H_2O)^{1/2}/LPM$. When coupled to an aerosol generating device (e.g., electronic cigarette) as provided herein, an adapter can be configured to generate an inhalation resistance of about 0.01 to about 0.03 $(cm\ H_2O)^{1/2}/LPM$, about 0.03 to about 0.05 $(cm\ H_2O)^{1/2}/LPM$, about 0.05 to about 0.07 $(cm\ H_2O)^{1/2}/LPM$, about 0.07 to about 0.09 $(cm\ H_2O)^{1/2}/LPM$, about 0.09 to about 0.11 $(cm\ H_2O)^{1/2}/LPM$, about 0.11 to about 0.13 $(cm\ H_2O)^{1/2}/LPM$, about 0.13 to about 0.15 $(cm\ H_2O)^{1/2}/LPM$, about 0.15 to about 0.17 $(cm\ H_2O)^{1/2}/LPM$, about 0.17 to about 0.19 $(cm\ H_2O)^{1/2}/LPM$, or about 0.19 to about 0.25 $(cm\ H_2O)^{1/2}/LPM$.

An adapter can be configured to have different geometries, dimensions, or sizes, to allow for an appropriate ratio of flow rate through the aerosol generating device (e.g., electronic cigarette) and flow rate into an attached adapter. An adapter can be configured to allow inhalation carrier gas (e.g., air) to flow into, and mix with, an aerosol exiting an aerosol generating device (e.g., electronic cigarette) coupled to the aerosol generating device (e.g., electronic cigarette) so that the total flow rate into the mouth is sufficient for inhalation of emitted aerosol particles into a deep lung.

An adapter can be configured, when coupled to an aerosol generating device (e.g., electronic cigarette), to modulate total flow rate into a mouth of a subject. The total flow rate into a mouth of a user can be about, more than, less than, at least, or at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 liters per min (LPM). The total flow rate into a mouth of a user can be about 1 to about 10 LPM, about 10 to about 20 LPM, about 20 to about 30 LPM, about 30 to about 40 LPM, about 40 to about 50 LPM, about 50 to about 60 LPM, about 60 to about 70 LPM, about 70 to about 80 LPM, about 80 to about 90 LPM, or about 90 to about 100 LPM when the user inhales through an adapter coupled to an aerosol generating device (e.g., electronic cigarette). The total flow rate into a mouth of a user can be about 5 to about 50 LPM, about 5 to about 45 LPM, about 10 to about 50 LPM, about 10 to about 40 LPM, about 20 to about 80 LPM, about 20 to about 100 LPM, or about 30 to about 50 LPM when the user inhales through an adapter coupled to an aerosol generating device (e.g., electronic cigarette). An adapter can be configured to permit inhalation into a lung of a user aerosol particles generated by an attached aerosol generating device (e.g., electronic cigarette). A flow rate at the outlet end of an aerosol generating device (e.g., electronic cigarette) can also be a total flow rate. The total flow rate can be a combination of one or more flow rates. The combination of flow rates can be a combination of a flow rate exiting an outlet end of an aerosol generating device (e.g., electronic cigarette) and one or more flow rates from one or more secondary inlets on an adapter coupled to an outlet end of the aerosol generating device (e.g., electronic cigarette). In some cases, an adapter when coupled to an aerosol generating device (e.g., electronic cigarette) increases the total flow rate of an aerosol into a mouth of a user relative to the flow rate of the aerosol at the outlet of an aerosol generating device (e.g., electronic cigarette) without the adapter. In some cases, an adapter, when coupled to an aerosol generating device (e.g., electronic cigarette) decreases the total flow rate of an aerosol into a mouth of a user relative to the flow rate of the aerosol at the outlet of the aerosol generating device (e.g., electronic cigarette) without the adapter.

In some cases, use of an adapter coupled to an aerosol generating device (e.g., electronic cigarette) does not significantly change (increase or decrease) the size of aerosol particles generated by an aerosol generating device (e.g., electronic cigarette). In some cases, an adapter can be used to increase or decrease the size of aerosol particles generated by an aerosol generating device (e.g., electronic cigarette).

In one embodiment, an adapter has an internal diameter of about 0.45 inches and has 4 secondary inlets, and each of the secondary inlets is 0.3 inches long and 0.08 inches wide. In some cases, an aerosol generating device provided herein is made up of multiple components or pieces. In some cases, the device provided herein is comprised of two pieces wherein a first piece comprises control (e.g., control apparatus) and power components (e.g. battery) and the second piece comprises a substrate (e.g., nicotine formulation) and heater element. In a further embodiment, the first piece is reusable and the second piece is replaceable. In yet another embodiment, the second piece is mated to the first piece. Mating of the second piece to the first piece can be accomplished by inserting the second piece into an interlocking channel in the second piece and engaging a locking mechanism. The locking mechanism can comprise a tab or button on the second piece which can be depressed. In one embodiment, the second piece is detachable from the first piece. In one embodiment, detachment of the second piece is accomplished by releasing the locking mechanism. In one embodiment, releasing the locking mechanism entails depressing the tab or button on the first piece. Electrical connection between the second and the first pieces can be accomplished through a set of mating electrical contacts. In one embodiment, attachment or mating of the dose cartridge to the controller establishes a functional carrier gas (e.g., air) sensor/switch. In some cases, the two piece device further comprises a third piece. The third piece can be an adaptor. The adaptor can be mated to an outlet end of the second piece. The adapter can be disposable or reusable.

IV. Systems and Kits

Provided herein are kits comprising one or more adapters and one or more aerosol generating devices. In some cases, the one or more aerosol generating devices are electronic cigarettes. The one or more aerosol generating devices can have any of the properties described herein. The one or more adapters can have any of the properties described herein. A kit can comprise one or more agents (e.g., nicotine), instructions, heater elements, replacement batteries, power supply, or flavorings. A kit can comprise one or more pieces of a multi-piece electronic cigarette (e.g., disposable units, precharged battery, solution cartridge, refill cartridge, non-disposable unit, rechargeable battery, atomizer, or replacement cartridge). A kit can comprise an airflow sensor. A kit can comprise disposable cartridges comprising an agent (e.g., nicotine).

Also provided herein are systems for delivery of an agent (e.g., nicotine) to a deep lung of a subject. The system can comprise an adapter as described herein that can be coupled to the mouth-end of an aerosol generating device (e.g., electronic cigarette). The aerosol generating device (e.g., electronic cigarette) can be configured to produce an aerosol with a particle size appropriate for deep lung delivery, and the adapter can be configured to generate a flow rate sufficient to deliver the aerosol to a lung of a subject.

EXAMPLES

Example 1: Effect of Changes in Activation Trip Points of Electronic Cigarettes on Particle Size of Aerosol Generated from the Electronic Cigarette Changes in activation trip points of commercially available electronic cigarettes can affect the particle sizes of aerosols generated from the electronic cigarettes. Two brands of electronic cigarettes, NJoy Bold and Finiti, were tested. The particle sizes of aerosols generated by the NJoy Bold and the Finiti were tested using a laser particle size detector (Malvern Spraytec). The particle size was first measured at the standard activation trip point for both brands of electronic cigarettes, which is around 1.5 to 2.0 liters per minute (LPM). At these activation trip points, the NJoy Bold produced aerosol particles with a mass median aerodynamic diameter (MMAD) of 0.4 to 0.6 microns and a geometric standard deviation (GSD) of 1.4 microns, while the Finiti produced particles with an MMAD of 0.35 microns and a GSD of 1.5. The internal air resistance of the electronic cigarettes was 2.5 (cm $H_2O)^{1/2}$/LPM for the NJoy electronic cigarette and 1.9 (cm $H_2O)^{1/2}$/LPM for the Finiti electronic cigarette.

The activation trip points for both the NJoy Bold and Finiti electronic cigarettes were changed to be 0.15 LPM. The activation trip points for both electronic cigarettes were changed by disconnecting the electrical contacts to the pressure sensors in the air flow switches in each electronic cigarette and reconnecting the electrical contacts with pressure sensors configured to be activated at 0.15 LPM. The pressure sensors configured to be activated at 0.15 LPM comprised a diaphragm with a diameter that was longer than the diameter of the diaphragm of the original air flow switches. At the 0.15 LPM activation trip point, the NJoy Bold produced particles with an MMAD of 1.3-1.4 microns, while the Finiti produced particles with an MMAD of 1.7-1.8 microns. The GSD's were 1.3 to 1.5.

Example 2: Effect of Addition of Dilution Air on Particle Size and Deep Lung Delivery of Aerosol Generated from Electronic Cigarettes Addition of dilution air to a mouthpiece of an electronic cigarette comprising an altered trip point as described in Example 1 can affect the flow rate of the aerosol particles generated by the electronic cigarettes. As shown in FIGS. 1A and 1B, an adapter (dilution adder) was coupled to the outlet end (i.e., mouthpiece) of an electronic cigarette. The adapter comprises secondary air inlets designed to permit addition of air to the aerosol after the aerosol exits the outlet end (i.e., mouthpiece) of the electronic cigarette. While the added air dilutes the particles, the size of the aerosol particles remains constant. The aerosol generated within the electronic cigarette has sufficient time to aggregate to a stable number concentration (e.g., about $10^9$ particles per cubic centimeter) before exposure to the air added through the secondary air inlets in the adapter. In this example, the adapter comprises four secondary air inlets in the shape of slits, wherein each slit measures 0.3 inches in length and 0.08 inches in width. The internal diameter of the adapter was 0.45 inches. While embodiments have been shown and described herein, it will be obvious to those skilled in the art that such embodiments are provided by way of example only. Numerous variations, changes, and substitutions will now occur to those skilled in the art without departing from the methods, devices, kits and systems provided herein. It should be understood that various alternatives to the embodiments described herein may be employed in practicing the methods, devices, kits and systems provided herein. It is intended that the following claims define the scope of the invention and that methods and structures within the scope of these claims and their equivalents be covered thereby.

What is claimed is:

1. An aerosol generating device, the device comprising an elongated housing comprising:
   a. a reservoir comprising a liquid substrate comprising nicotine and a carrier;
   b. an air flow channel comprising:
      i. a first air inlet;
      ii. a heater element, wherein the heater element comprises a coil wrapped around a wick element, wherein the coil and wick element are made of an electrically resistive material that when heated vaporizes the liquid substrate comprising nicotine and a carrier that is delivered onto the heater element;
      iii. a tube located within the air flow channel; wherein the tube is in fluid communication with the reservoir and the heater element; and
      iv. an outlet, wherein the heater element is located in an aerosol generation region of the air flow channel between the inlet and the outlet, and wherein the device is configured to emit a condensation aerosol comprising nicotine and a carrier from the outlet;
      v. a second air inlet, wherein the second air inlet is located between the aerosol generation region and the outlet;
   c. a pump connected to the tube, wherein the pump is configured to deliver the liquid substrate comprising nicotine and the carrier through the tube onto the heater element;
   d. an air flow switch, wherein the air flow switch is configured to activate the heater element at an air flow rate through the aerosol generating region of less than 1 LPM; and
   e. a power supply, wherein the power supply is in electrical communication with the heater element and the air flow switch.

2. The aerosol generating device of claim 1 wherein entrainment air enters the air flow channel through the second air inlet and entrains condensation aerosol particles having a diameter of from about 1 µm to about 5 µm at a rate effective to deliver the condensation aerosol to a deep lung of a user of the device.

3. The aerosol generating device of claim 1 wherein the entrainment air has a flow rate of about 6 liters per minute to about 40 liters per minute (LPM).

4. The aerosol generating device of claim 1 wherein the air flow channel comprises a gas-control valve located between the first inlet and the aerosol generation region, wherein the gas-control valve is configured to limit air flowing through the aerosol generation region of the air flow channel to the a flow rate that generates condensation aerosol particles having a diameter of from about 1 µm to about 5 µm.

5. The aerosol generating device of claim 4 wherein the diameter is a mass median aerodynamic diameter (MMAD).

6. An aerosol generating device comprising:
   a housing;
   a reservoir in the housing, the reservoir containing a liquid substrate including nicotine and a carrier;
   an air flow channel including a first air inlet, a second air inlet, and an outlet;
   a heater in an aerosol generation region of the air flow channel between the first air inlet and the outlet, the heater including a coil wrapped around a wick, the coil and wick comprising electrically resistive materials;
   the second air inlet located between the aerosol generation region and the outlet;
   a pump connected to a tube leading from the reservoir to the heater;
   an air flow switch configured to activate the heater at a predetermined air flow rate through the aerosol generating region; and
   a battery electrically connected to the heater and the air flow switch.

7. An aerosol generating device comprising:
   a housing;
   a reservoir in the housing containing a liquid;
   an air flow channel in the housing including a first air inlet, a second air inlet, and an outlet;
   a heater in an aerosol generation region of the air flow channel between the first air inlet and the outlet;
   the second air inlet located between the aerosol generation region and the outlet;
   a pump for pumping liquid from the reservoir through a tube to the heater;
   an air flow switch configured to activate the heater at a predetermined air flow rate through the aerosol generating region; and
   a battery electrically connectable to the heater, the air flow switch and the pump.

8. The aerosol generating device of claim 7 wherein the heater includes a coil wrapped around a wick.

9. The aerosol generating device of claim 8 wherein the coil and the wick comprise electrically resistive materials.

* * * * *